Figure 1:
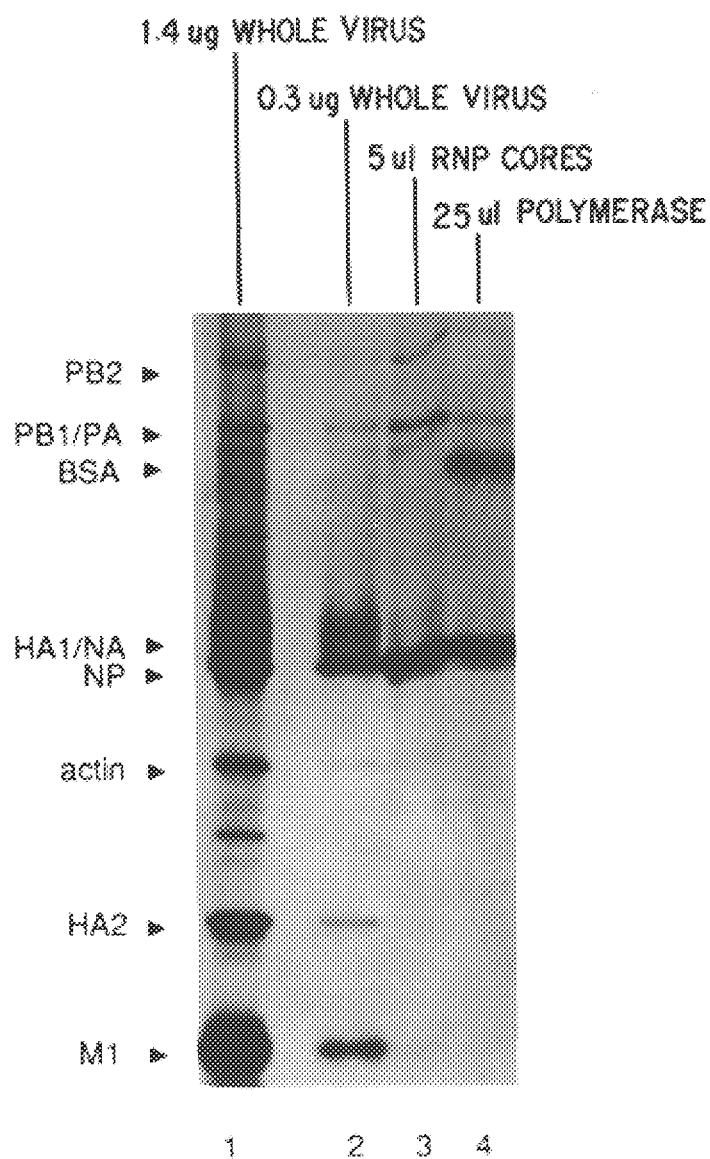

United States Patent [19]

Clarke et al.

[11] Patent Number: 5,840,520
[45] Date of Patent: *Nov. 24, 1998

[54] RECOMBINANT NEGATIVE STRAND RNA VIRUS EXPRESSION SYSTEMS

[75] Inventors: David Kirkwood Clarke, Pacifica, Calif.; Peter M. Palese, Leonia, N.J.

[73] Assignee: Aviron, Mountain View, Calif.

[ * ] Notice: The term of this patent shall not extend beyond the expiration date of Pat. No. 5,166,057.

[21] Appl. No.: 316,439

[22] Filed: Sep. 30, 1994

Related U.S. Application Data

[63] Continuation-in-part of Ser. No. 190,698, Feb. 1, 1994, abandoned, which is a continuation of Ser. No. 925,061, Aug. 4, 1992, abandoned, which is a division of Ser. No. 527,237, May 22, 1990, Pat. No. 5,166,057, which is a continuation-in-part of Ser. No. 440,053, Nov. 21, 1989, abandoned, and Ser. No. 399,728, Aug. 28, 1989, abandoned.

[51] Int. Cl.[6] .............................. C12P 21/06; C12P 19/34; A61K 39/12
[52] U.S. Cl. ........................ 435/69.1; 435/91; 435/235.1; 435/320.1; 424/199.1; 536/23.1
[58] Field of Search ....................... 435/69.1, 91, 172.3, 435/235.1, 320.1; 536/23.1; 424/199.1

[56] References Cited

U.S. PATENT DOCUMENTS

| | | | |
|---|---|---|---|
| 4,786,600 | 11/1988 | Kramer et al. | 435/235.1 |
| 5,149,650 | 9/1992 | Wertz et al. | 435/243 |
| 5,166,057 | 11/1992 | Palese et al. | 435/69.1 |

OTHER PUBLICATIONS

Polo et al, 1988, J. of Virology, pp. 2124–2133.
Garcia–Sastre, 1993, Ann. Rev. Microbiol., vol. 47:765–790.
Collins, P.L. et al. 1986, Proc. Natl. Acad. Sci. USA, vol. 83, pp. 4594–4598.
Collins, P.L. et al. 1984, Proc. Natl. Acad. Sci. USA, vol. 81 pp. 7683–7687.
Olmsted, R. et al., Proc. Natl. Acad. Sci. USA, vol. 83 pp. 7462–7466, 1986.
Pelletier, J. et al. Nature, vol. 334, pp. 320–325.
Enami, M. et al., 1991, J. Virol, vol. 65, pp. 2711–2713.
Muster, T. et al., 1991, Proc. Natl. Acad. Sci. USA, vol. 88, pp. 5177–5181.
Enami, M. et al., 1991, Virol., vol. 185, pp. 291–298.
Park, K.H. et al., 1991, Proc. Natl. Acad. Sci. USA, vol. 88, pp. 5537–5541.
Collins, P.L. et al., 1991, Proc. Natl. Acad. Sci. USA, vol. 88, pp. 9663–9667.
Elliott, R.M. et al., 1990, J. Gen. Virol., vol. 71, pp. 1413–1426.
Levis, R. et al., 1987, Proc. Natl. Acad. Sci. USA, vol. 84, pp. 4811–4815.
Chanda, P.K. et al., 1983, J. Virol., vol. 45, pp. 55–61.
Fields, S. et al., 1982, Cell, vol. 28, pp. 303–313.
Parvin et al., Dec. 1989, J. Virol., 63:5142–5152.
Luytjes et al., Dec. 1989, Cell, 59:1107–1113.
Enami et al., May 1990, Proc. Natl. Acad. Sci., 87:3802–3805.
Ballart et al., Feb. 1990, EMBO J., 9:379–384; and its retraction at 8th International Conference on Negative Strand Viruses, Etp. 1991, Abstr. 43.
Huang et al., Nov. 1990, J. Virol., 64:5669–5673.
Ballart, 1991, J. Virol., 65:3161–3166; and its retraction attached.
Emerson and Yu, 1975, J. Virol., 15:1348–1356.
Naito and Ishihama, 1976, J. Biol. Chem., 251:4307–4314.
Hay et al., 1977, Virology, 83:337–355.
Racaniello et al., 1981, Science, 214:916–919.
Lamb and Choppin, 1983, Ann. Rev. Biochem., 52:467–506.
Krug, Transcription and Replication of Influenza Viruses. In: Genetics of Influenza Viruses, Ed., Palese, P. and dKingsbury, D.W., New York, Springer–Verlag, 183, pp. 70–98.
Dreher et al., 1984, Nature, 311:171–175.
Dreher and Hall, 1988, J. Mol. Biol., 201:31–40.
Kaplan et al., 1985, Proc. Natl. Acad. Sci. USA, 82:8424–8428.
Kato et al., 1985, Virus Research, 3:115–127.
De and Banergee, 1985, Biochem. Biophys. Res. Commun., 126:40–49.
Beaton and Krug, 1986, Proc. Natl. Acad. Sci. USA, 84:8140–8144.
Levis et al., 1986, Cell, 44:137–145.
Takeuchi et al., 1987, J. Biochem., 101:837–845.
Hsu et al., 1987, Proc. Natl. Acad. Sci. USA, 84:8140–8144.
Honda et al., 1987, J. Biochem., 102:1241–1249.
Ward et al., 1988, J. Virol., 62:558–562.

(List continued on next page.)

Primary Examiner—Michael P. Woodward
Assistant Examiner—Ali R. Salimi
Attorney, Agent, or Firm—Pennie & Edmonds LLP

[57] ABSTRACT

Recombinant negative strand virus RNA templates which may be used to express heterologous gene products and/or to construct chimeric viruses are described. Influenza viral polymerase, which was prepared depleted of viral RNA, was used to copy small RNA templates prepared from plasmid-encoded sequences. Template constructions containing only the 3' end of genomic RNA were shown to be efficiently copied, indicative that the promoter lay solely within the 15 nucleotide 3' terminus. Sequences not specific for the influenza viral termini were not copied, and, surprisingly, RNAs containing termini identical to those from plus sense cRNA were copied at low levels. The specificity for recognition of the virus-sense promoter was further defined by site-specific mutagenesis. It was also found that increased level of viral protein were required in order to catalyze both the cap-endonuclease primed and primer-free RNA synthesis from these model templates as well as from genomic length RNAs. This indicated that this reconstituted system had catalytic properties very similar to those of native viral RNPs. High levels of expression of a heterologous gene was obtained using the constructs and methods described. The system was exemplified using Influenza and respiratory syncytial virus.

9 Claims, 23 Drawing Sheets

OTHER PUBLICATIONS

Mirakhur and Peluso, 1988, *Proc. Natl. Acad. Sci.*, 85:7511–7515.
Ishihama and Nagata, 1988, *CRC Crlt. Rev. Biochem.* 23:27–76.
Shapiro and Krug, 1988, *J. Virol.*, 62:2285–2290.
Honda et al., 1988, *J. Biochem.*, 104:1021–1026.
Szewczyk, et al., 1988, *Proc. Natl. Acad. Sci. USA*, 85:7907–7911.
Palese, 1977, *Cell*, 10:1–10.
Bishop et al. 1971, *J. Virol.*, 8:66–73.
Bouloy et al., 1980, *Proc. Natl. Acad. Sci. USA*, 77:3952–3956.
Ulmanen et al, 1983, *J. Virol.*, 45:27–35.
Beaton and Krug, 1984, *Proc. Natl. Acad. Sci. USA*, 81:4682–4686.
Kawakami et al., 1981, *J. Biochem.*, 89:1759–1768.
Kawakami and Isihama, 1983, *J. Biochem.*, 93:989–996.
Detjen et al., 1987, *J. Virol.*, 61:16–22.
St. Angelo et al., 1987, *J. Virol.*, 61:361–365.
Khan et al., 1987, *Nucleosides and Nucleotides*, 6:543–554.
Krystal et al., 1986, *Proc. Natl. Acad. Sci. USA*, 83:2709–2713.
Li et al., 1989, *Virus Research*, 12:97–112.
Kingsbury et al., 1987, *Virology*, 156:396–403.
Scholtissek and Becht, 1971, *J. Gen. Virol.* 10:11–16.
Rochavansky, 1976, *Virology*, 73:327–338.
Robertson et al., 1981, *J. Virol.*, 38:157–163.
Schreirer et al., 1988, *Acta. Virol.*, 32:289–295.
Mink et al., 1991, Virology, 185:615–624.
Collins et al., 1991, Proc. Natl. Acad. Sci., 88:9663–9667.
Collins et al., 1993, Virology, 195:262–256.
Gorman et al., 1982, Mol. Cell. Biol., 2:1044–1051.
Ward et al., 1983, Gen. Virol., 64:1867–1876.
Wang et al., 1989, Proc. Natl. Acad. Sci., 86:9717–9721.
McIntosh, 1990, Respiratory Syncytial Virus in Virology, 2d Ed. edited by B.N. Fields, D.M. Knipe et al., Raven Press, Ltd., New York, Chapter 38, pp. 1045–1073.
Beeler and Coelingh, 1988, J. Virol., 63:2941–2950.

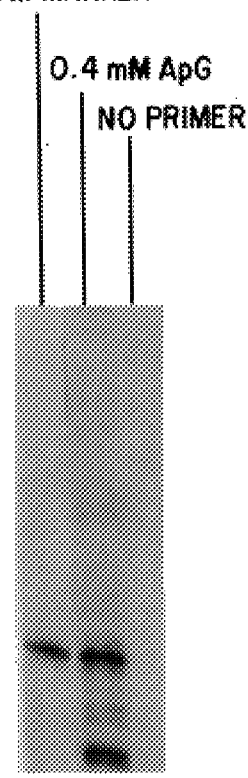
FIG. 3A
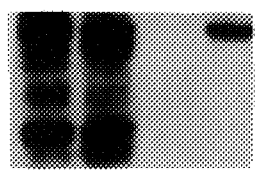
FIG. 3B
FIG. 3C

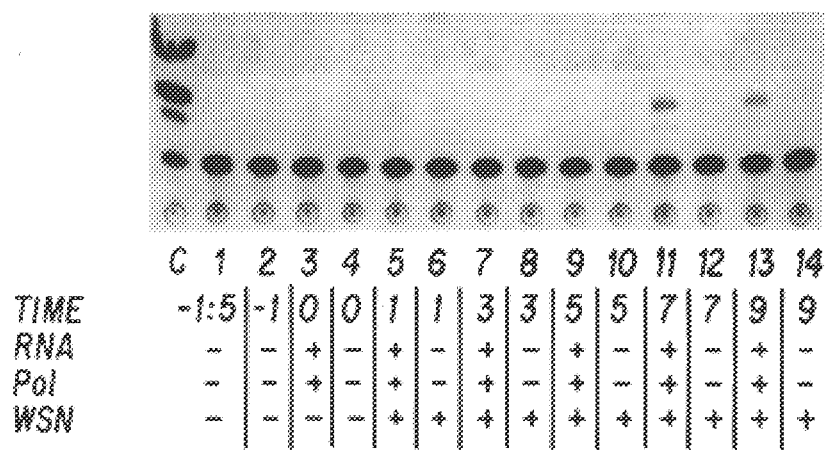
FIG.14A
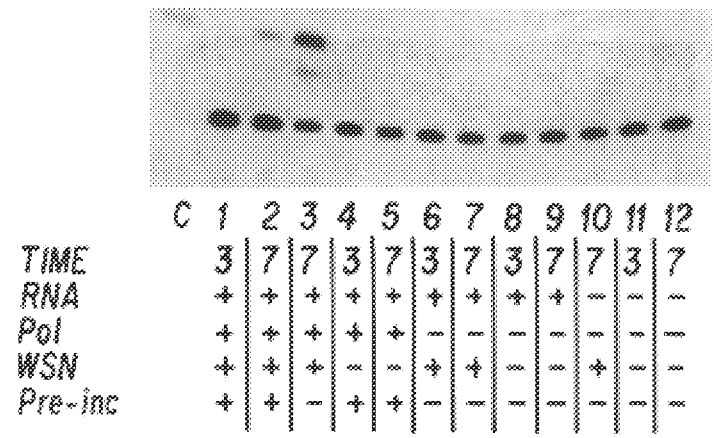
FIG.14B
FIG.14C 1    2    3        4

FIG. 19
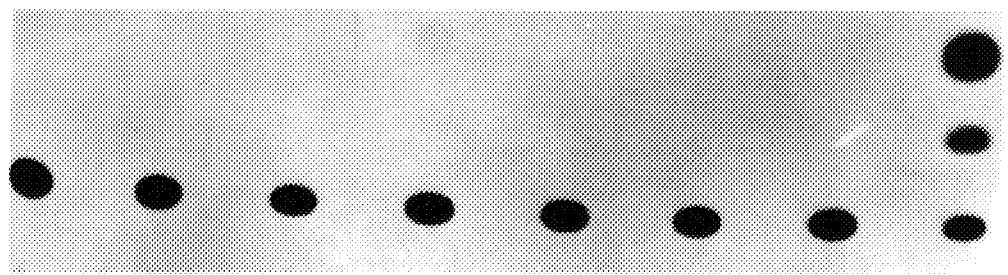
| 1 | 2 | 3 | 4 | 5 | 6 | 7 | 8 |
|---|---|---|---|---|---|---|---|
| C | NAKED RNA NO VIRUS | NO VIRUS | INF. VIRUS | PB2 | PB2 PB1 | PB2 PB1 PA | PB2 PB1 PA NP |
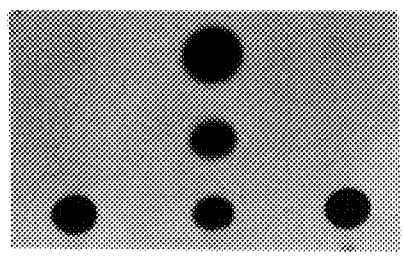
| 9 | 10 | 11 |
|---|----|----|
| PB2 PA NP | PB2 PB1 PA NP | PB1 PA NP |

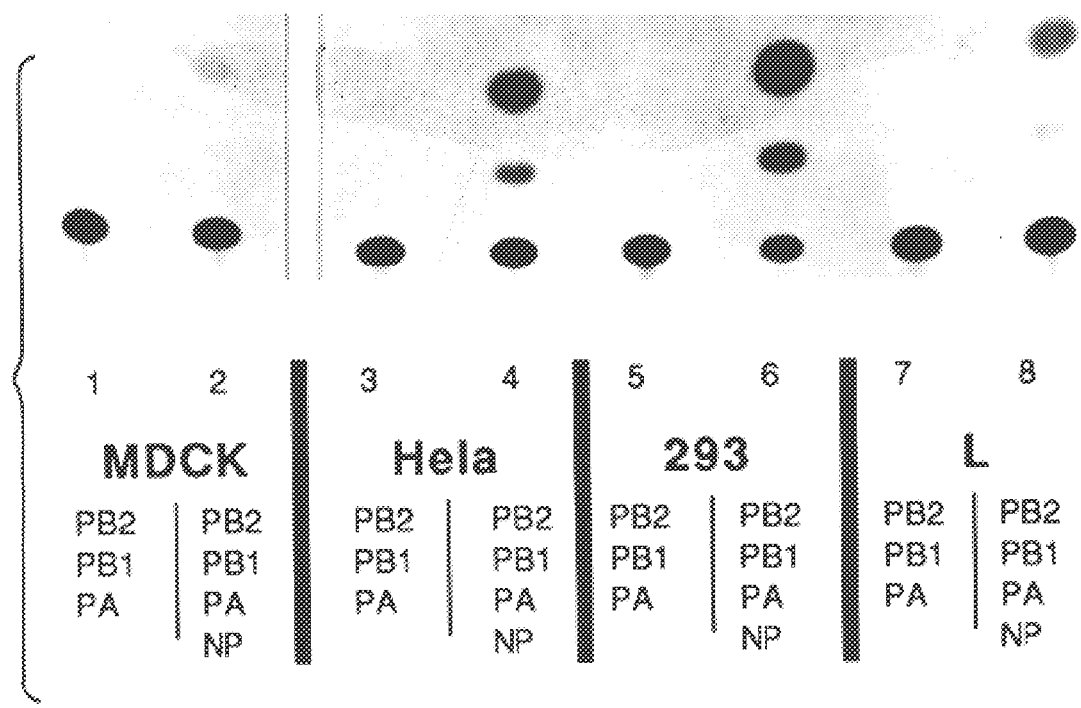
FIG.20A
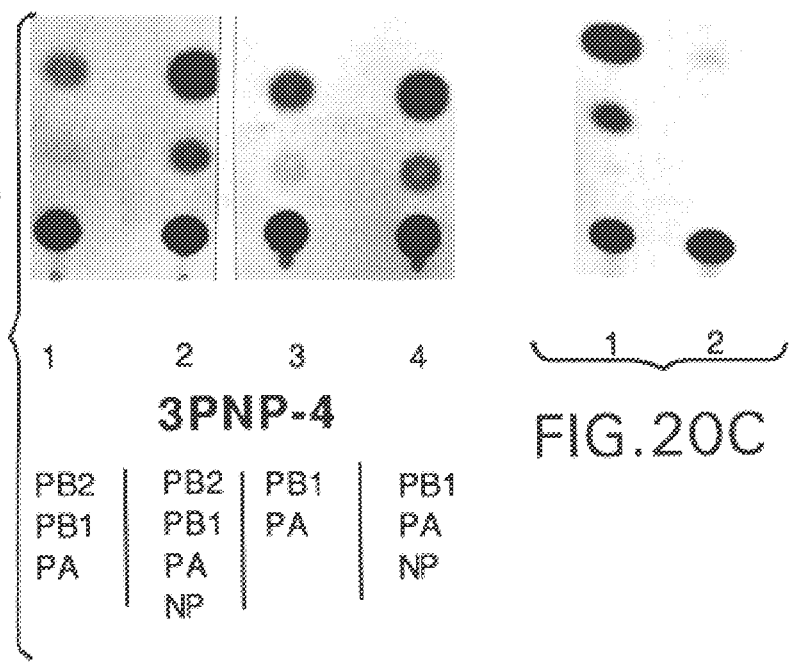
FIG.20B
FIG.20C

RECOMBINANT NEGATIVE STRAND RNA VIRUS EXPRESSION SYSTEMS

This application is a continuation-in-part of application Ser. No. 08/190,698 filed Feb. 1, 1994, now abandoned, which is a continuation of Ser. No. 07/925,061 filed Aug. 4, 1992 (now abandoned) which is a divisional of Ser. No. 07/527,237 (now U.S. Pat. No. 5,166,057), which is a continuation-in-part of Ser. No. 07/440,053 filed Nov. 21, 1989 (now abandoned) and Ser. No. 07/399,728, filed Aug. 28, 1989, (now abandoned) which are incorporated by reference herein in their entirety.

1. INTRODUCTION

The present invention relates to recombinant negative strand virus RNA templates which may be used to express heterologous gene products in appropriate host cell systems and/or to construct recombinant viruses that express, package, and/or present the heterologous gene product. The expression products and chimeric viruses may advantageously be used in vaccine formulations.

The invention is demonstrated by way of examples in which recombinant influenza virus RNA templates containing a heterologous gene coding sequences in the negative-polarity were constructed. These recombinant templates, when combined with purified viral RNA-directed RNA polymerase, were infectious, replicated in appropriate host cells, and expressed the heterologous gene product at high levels. In addition, the heterologous gene was expressed and packaged by the resulting recombinant influenza viruses. The invention is further demonstrated by way of examples in which recombinant respiratory syncytial virus RNA templates containing a heterologous gene coding sequence in the negative-polarity were constructed and used to infect and replicate in appropriate host cells.

2. BACKGROUND OF THE INVENTION

A number of DNA viruses have been genetically engineered to direct the expression of heterologous proteins in host cell systems (e.g., vaccinia virus, baculovirus, etc.). Recently, similar advances have been made with positive-strand RNA viruses (e.g., poliovirus). The expression products of these constructs, i.e., the heterologous gene product or the chimeric virus which expresses the heterologous gene product, are thought to be potentially useful in vaccine formulations (either subunit or whole virus vaccines). One drawback to the use of viruses such as vaccinia for constructing recombinant or chimeric viruses for use in vaccines is the lack of variation in its major epitopes. This lack of variability in the viral strains places strict limitations on the repeated use of chimeric vaccinia, in that multiple vaccinations will generate host-resistance to the strain so that the inoculated virus cannot infect the host. Inoculation of a resistant individual with chimeric vaccina will, therefore, not induce immune stimulation.

By contrast, influenza virus, a negative-strand RNA virus, demonstrates a wide variability of its major epitopes. Indeed, thousands of variants of influenza have been identified; each strain evolving by antigenic drift. The negative-strand viruses such as influenza would be attractive candidates for constructing chimeric viruses for use in vaccines because its genetic variability allows for the construction of a vast repertoire of vaccine formulations which will stimulate immunity without risk of developing a tolerance. However, achieving this goal has been precluded by the fact that, to date, it has not been possible to construct recombinant or chimeric negative-strand RNA particles that are infectious.

2.1. The Influenza Virus

Virus families containing enveloped single-stranded RNA of the negative-sense genome are classified into groups having non-segmented genomes (Paramyxoviridae, Rhabdoviridae) or those having segmented genomes (Orthomyxoviridae, Bunyaviridae and Arenaviridae). The Orthomyxoviridae family, described in detail below, and used in the examples herein, contains only the viruses of influenza, types A, B and C.

The influenza virions consist of an internal ribonucleoprotein core (a helical nucleocapsid) containing the single-stranded RNA genome, and an outer lipoprotein envelope lined inside by a matrix protein (M). The segmented genome of influenza A consists of eight molecules (seven for influenza C) of linear, negative polarity, single-stranded RNAs which encode ten polypeptides, including: the RNA-directed RNA polymerase proteins (PB2, PB1 and PA) and nucleoprotein (NP) which form the nucleocapsid; the matrix proteins (M1, M2); two surface glycoproteins which project from the lipoprotein envelope: hemagglutinin (HA) and neuraminidase (NA); and nonstructural proteins whose function is unknown (NS 1 and NS2). Transcription and replication of the genome takes place in the nucleus and assembly occurs via budding on the plasma membrane. The viruses can reassort genes during mixed infections.

Influenza virus adsorbs via HA to sialyloligosaccharides in cell membrane glycoproteins and glycolipids. Following endocytosis of the virion, a conformational change in the HA molecule occurs within the cellular endosome which facilitates membrane fusion, thus triggering uncoating. The nucleocapsid migrates to the nucleus where viral mRNA is transcribed as the essential initial event in infection. Viral mRNA is transcribed by a unique mechanism in which viral endonuclease cleaves the capped 5'-terminus from cellular heterologous mRNAs which then serve as primers for transcription of viral RNA templates by the viral transcriptase. Transcripts terminate at sites 15 to 22 bases from the ends of their templates, where oligo(U) sequences act as signals for the template-independent addition of poly(A) tracts. Of the eight viral mRNA molecules so produced, six are monocistronic messages that are translated directly into the proteins representing HA, NA, NP and the viral polymerase proteins, PB2, PB1 and PA. The other two transcripts undergo splicing, each yielding two mRNAs which are translated in different reading frames to produce M1, M2, NS1 and NS2. In other words, the eight viral mRNAs code for ten proteins: eight structural and two nonstructural. A summary of the genes of the influenza virus and their protein products is shown in Table I below.

TABLE I

Influenza Virus Genome RNA Segments and Coding Assignments[a]

| Segment | Length[b] (Nucleotides) | Encoded Polypeptide[c] | Length[d] (Amino Acids) | Molecules Per Virion | Comments |
|---|---|---|---|---|---|
| 1 | 2341 | PB2 | 759 | 30–60 | RNA transcriptase component; host cell RNA cap binding |
| 2 | 2341 | PB1 | 757 | 30–60 | RNA transcriptase component; initiation of transcription; endonuclease activity? |

TABLE I-continued

Influenza Virus Genome RNA Segments and Coding Assignments[a]

| Segment | Length[b] (Nucleotides) | Encoded Polypeptide[c] | Length[d] (Amino Acids) | Molecules Per Virion | Comments |
|---|---|---|---|---|---|
| 3 | 2233 | PA | 716 | 30–60 | RNA transcriptase component; elongation of mRNA chains? |
| 4 | 1778 | HA | 566 | 500 | Hemagglutinin; trimer; envelope glycoprotein; mediates attachment to cells |
| 5 | 1565 | NP | 498 | 100 | Nucleoprotein; associated with RNA; structural component of RNA transcriptase |
| 6 | 1413 | NA | 454 | 100 | Neuraminidase; tetramer; envelope glycoprotein |
| 7 | 1027 | $M_1$ | 252 | 3000 | Matrix protein; lines inside of envelope |
|   |   | $M_2$ | 96 |   | Structural protein in plasma membrane; spliced mRNA |
|   |   | ? | ?9 |   | Unidentified protein |
| 8 | 890 | $NS_1$ | 230 |   | Nonstructural protein; function unknown |
|   |   | $NS_2$ | 121 |   | Nonstructural protein; function unknown; spliced mRNA |

[a]Adapted from R. A. Lamb and P. W. Choppin (1983), Reproduced from the Annual Review of Biochemistry, Volume 52, 467–506.
[b]For A/PR/8/34 strain.
[c]Determined by biochemical and genetic approaches.
[d]Determined by nucleotide sequence analysis and protein sequencing.

Following transcription, virus genome replication is the second essential event in infection by negative-strand RNA viruses. As with other negative-strand RNA viruses, virus genome replication in influenza is mediated by virus-specified proteins. It is hypothesized that most or all of the viral proteins that transcribe influenza virus mRNA segments also carry out their replication. All viral RNA segments have common 3' and 5' termini, presumably to enable the RNA-synthesizing apparatus to recognize each segment with equal efficiency. The mechanism that regulates the alternative uses (i.e., transcription or replication) of the same complement of proteins (PB2, PB1, PA and NP) has not been clearly identified but appears to involve the abundance of free forms of one or more of the nucleocapsid proteins, in particular, the NP. The nucleus appears to be the site of virus RNA replication, just as it is the site for transcription.

The first products of replicative RNA synthesis are complementary copies (i.e., plus-polarity) of all influenza virus genome RNA segments (cRNA). These plus-stranded copies (anti-genomes) differ from the plus-strand mRNA transcripts in the structure of their termini. Unlike the MRNA transcripts, the anti-genomic cRNAs are not capped and methylated at the 5' termini, and are not truncated and polyadenylated at the 3' termini. The cRNAs are coterminal with their negative strand templates and contain all the genetic information in each genomic RNA segment in the complementary form. The cRNAs serve as templates for the synthesis of genomic negative-strand vRNAs.

The influenza virus negative strand genomes (vRNAs) and antigenomes (cRNAs) are always encapsidated by nucleocapsid proteins; the only unencapsidated RNA species are virus mRNAs. In contrast to the other enveloped RNA viruses, nucleocapsid assembly appears to take place in the nucleus rather than in the cytoplasm. The virus matures by budding from the apical surface of the cell incorporating the M protein on the cytoplasmic side or inner surface of the budding envelope. The HA and NA become glycosylated and incorporated into the lipid envelope. In permissive cells, HA is eventually cleaved, but the two resulting chains remain united by disulfide bonds.

It is not known by what mechanism one copy of each of the eight genomic viral RNAs is selected for incorporation into each new virion. Defective interfering (DI) particles are often produced, especially following infection at high multiplicity.

2.2. RNA Directed RNA Polymerase

The RNA-directed RNA polymerases of animal viruses have been extensively studied with regard to many aspects of protein structure and reaction conditions. However, the elements of the template RNA which promote optimal expression by the polymerase could only be studied by inference using existing viral RNA sequences. This promoter analysis is of interest since it is unknown how a viral polymerase recognizes specific viral RNAs from among the many host-encoded RNAs found in an infected cell.

Animal viruses containing plus-sense genome RNA can be replicated when plasmid-derived RNA is introduced into cells by transfection (for example, Racaniello et al. 1981, Science 214: 916–919; Levis, et al., 1986, Cell 44: 137–145). In the case of poliovirus, the purified polymerase will replicate a genome RNA in in vitro reactions and when this preparation is transfected into cells it is infectious (Kaplan, et al., 1985, Proc. Natl. Acad. Sci. USA 82: 8424–8428). However, the template elements which serve as transcription promoter for the poliovirus-encoded polymerase are unknown since even RNA homopolymers can be copied (Ward, et al., 1988, J. Virol. 62: 558–562). SP6 transcripts have also been used to produce model defective interfering (DI) RNAs for the Sindbis viral genome. When the RNA is introduced into infected cells, it is replicated and packaged. The RNA sequences which were responsible for both recognition by the Sindbis viral polymerase and packaging of the genome into virus particles were shown to be within 162 nucleotides (nt) of the 5' terminus and 19 nt of the 3' terminus of the genome (Levis, et al., 1986, Cell 44: 137–145). In the case of brome mosaic virus (BMV), a positive strand RNA plant virus, SP6 transcripts have been used to identify the promoter as a 134 nt tRNA-like 3' terminus (Dreher, and Hall, 1988, J. Mol. Biol. 201: 31–40). Polymerase recognition and synthesis were shown to be dependent on both sequence and secondary structural features (Dreher, et al., 1984, Nature 311: 171–175).

The negative-sense RNA viruses have been refractory to study of the sequence requirements of the replicase. The purified polymerase of vesicular stomatitis virus is only active in transcription when virus-derived ribonucleoprotein complexes (RNPs) are included as template (De and Banerjee, 1985, Biochem. Biophys. Res. Commun. 126: 40–49); Emerson and Yu, 1975, J. Virol. 15: 1348–1356; Naito, and Ishihama, 1976, J. Biol. Chem. 251: 4307–4314). RNPs have been reconstituted from naked RNA of VSV DI particles using infected cell extracts as protein source. These RNPs were then replicated when added back to infected cells (Mirakhur, and Peluso, 1988, Proc. Natl. Acad. Sci. USA 85: 7511–7515). With regard to influenza viruses, it was recently reported that naked RNA purified from virus was used to reconstitute RNPs. The viral nucleocapsid and polymerase proteins were gel-purified and renatured on the viral RNA using thioredoxin (Szewczyk, et al., 1988, Proc. Natl. Acad. Sci. USA, 85: 7907–7911). However, these authors did not show that the activity of the preparation was specific for influenza viral RNA, nor did they analyze the signals which promote transcription.

During the course of influenza virus infection the polymerase catalyzes three distinct transcription activities. These include the synthesis of (a) subgenomic mRNA, which contains a 5' cap and a 3' poly-A tail; (b) a full length plus-strand or anti-genome (cRNA) copied from the genome RNA; and (c) genomic vRNA synthesized from the full length cRNA (reviewed in Ishihama and Nagata, 1988, CRC Crit. Rev. Biochem. 23: 27–76; and Krug, Transcription and replication of influenza viruses. In: Genetics of influenza viruses, Ed., Palese, P. and Kingsbury, D. W. New York, Springer-Verlag, 1983, p. 70–98). Viral proteins PB2, PB1 and PA are thought to catalyze all influenza virus-specific RNA synthesis when in the presence of excess nucleocapsid protein (NP; see above reviews). These polymerase functions have been studied using RNP cores derived from detergent-disrupted virus, and RNPs from the nuclear extracts of infected cells. Transcription from the RNPs derived from disrupted virus occurs when primed with either dinucleotide adenylyl-(3'–5')-guanosine (ApG) or capped mRNAs. The plus sense mRNA products have terminated synthesis 17–20 nucleotides upstream of the 5' terminus of the RNA template and have been processed by the addition of poly A tails. These products cannot serve as template for the viral-sense genome since they lack terminal sequences (Hay, et al., 1977, Virology 83: 337–355). RNPs derived from nuclear extracts of infected cells also synthesize polyadenylated mRNA in the presence of capped RNA primers. However, if ApG is used under these conditions, both RNAs, polyadenylated and full length cRNA, can be obtained (Beaton and Krug, 1986, Proc. Natl. Acad. Sci. USA 83: 6282–6286; Takeuchi, et al., 1987, J. Biochem. 101: 837–845). Recently it was shown that replicative synthesis of cRNA could occur in the absence of exogenous primer if the nuclear extract was harvested at certain times post infection. In these same preparations the synthesis of negative-sense vRNA from a cRNA template was also observed (Shapiro and Krug, 1988, J. Virol. 62: 2285–2290). The synthesis of full length cRNA was shown to be dependent upon the presence of nucleocapsid protein (NP) which was free in solution (Beaton and Krug, 1986, Proc. Natl. Acad. Sci. USA 83: 6282–6286; Shapiro and Krug, 1988, J. Virol. 62: 2285–2290). These findings led to the suggestion that the regulatory control between mRNA and cRNA synthesis by the RNP complex is based on the requirement for there being an excess of soluble NP (Beaton and Krug, 1986, Proc. Natl. Acad. Sci. USA 83: 6282–6286).

Another line of investigation has focused on the preparation of polymerase-RNA complexes derived from RNPs from detergent-disrupted virus. When the RNP complex is centrifuged through a CsCl-glycerol gradient, the RNA can be found associated with the three polymerase (P) proteins at the bottom of the gradient. Near the top of the gradient, free NP protein can be found (Honda, et al., 1988, J. Biochem. 104: 1021–1026; Kato, et al., 1985, Virus Research 3, 115–127). The purified polymerase-RNA complex (bottom of gradient), is active in initiating ApG-primed synthesis of RNA, but fails to elongate to more than 12–19 nucleotides. When fractions from the top of the gradient containing the NP protein are added back to the polymerase-RNA complex, elongation can ensue (Honda, et al., 1987, J. Biochem. 102: 41–49). These data suggest that the NP protein is needed for elongation, but that initiation can occur in the absence of NP.

It has been shown that the genomic RNA of influenza viruses is in a circular conformation via base-pairing of the termini to form a panhandle of 15 to 16 nt (Honda, et al., 1988, J. Biochem. 104: 1021–1026; Hsu, et al., 1987, Proc. Natl. Acad. Sci. USA 84: 8140–8144). Since the viral polymerase was found bound to the panhandle, this led to the suggestion that a panhandle structure was required for recognition by the viral polymerase (Honda, et al., 1988, J. Biochem. 104: 1021–1026). Therefore, it was hypothesized in these two reports that the promoter for the viral RNA polymerase was the double stranded RNA in panhandle conformation.

3. SUMMARY OF THE INVENTION

Recombinant negative-strand viral RNA templates are described which may be used with purified RNA-directed RNA polymerase complex to express heterologous gene products in appropriate host cells and/or to rescue the heterologous gene in virus particles. Both influenza and respiratory syncytial viral templates are exemplified. The RNA templates are prepared by transcription of appropriate DNA sequences with a DNA-directed RNA polymerase. The resulting RNA templates are of the negative-polarity and contain appropriate terminal sequences which enable the viral RNA-synthesizing apparatus to recognize the template.

As demonstrated by the examples described herein, recombinant negative-sense influenza RNA templates may be mixed with purified viral polymerase proteins and nucleoprotein (i.e., the purified viral polymerase complex) to form infectious recombinant RNPs. These can be used to express heterologous gene products in host cells or to rescue the heterologous gene in virus particles by cotransfection of host cells with recombinant RNPs and virus. Alternatively, the recombinant RNA templates or recombinant RNPs may be used to transfect transformed cell lines that express the RNA dependent RNA-polymerase and allow for complementation. Additionally, a non-virus dependent replication system for influenza virus is also described. Vaccinia vectors expressing influenza virus polypeptides were used as the source of proteins which were able to replicate and transcribe synthetically derived RNPs. The minimum subset of influenza virus protein needed for specific replication and expression of the viral RNP was found to be the three polymerase proteins (PB2, PB1 and PA) and the nucleoprotein (NP). This suggests that the nonstructural proteins, NS1 and NS2, are not absolutely required for the replication and express of viral RNP.

The expression products and/or chimeric virions obtained may advantageously be utilized in vaccine formulations. The use of recombinant influenza for this purpose is especially attractive since influenza demonstrates tremendous strain variability allowing for the construction of a vast repertoire of vaccine formulations. The ability to select from thousands of influenza variants for constructing chimeric viruses obviates the problem of host resistance encountered when using other viruses such as vaccinia. In addition, since influenza stimulates a vigorous secretory and cytotoxic T cell response, the presentation of foreign epitopes in the influenza virus background may also provide for the induction of secretory immunity and cell-mediated immunity.

3.1. Definitions

As used herein, the following terms will have the meanings indicated:

cRNA=anti-genomic RNA
HA=hemagglutinin (envelope glycoprotein)
M=matrix protein (lines inside of envelope)
MDCK=Madin Darby canine kidney cells
MDBK=Madin Darby bovine kidney cells
moi=multiplicity of infection
NA=neuraminidase (envelope glycoprotein)
NP=nucleoprotein (associated with RNA and required for polymerase activity)
NS=nonstructural protein (function unknown)
nt=nucleotide
PA, PB1, PB2 =RNA-directed RNA polymerase components
RNP=ribonucleoprotein (RNA, PB2, PB1, PA and NP)
rRNP=recombinant RNP
vRNA=genomic virus RNA
viral polymerase complex=PA, PB1, PB2 and NP
WSN=influenza A/WSN/33 virus
WSN-HK virus: reassortment virus containing seven genes from WSN virus and the NA gene from influenza A/HK/8/68 virus

4. DESCRIPTION OF THE FIGURES

FIG. 1. Purification of the polymerase preparation. RNP cores were purified from whole virus and then subjected to CsCl-glycerol gradient centrifugation. The polymerase was purified from fractions with 1.5 to 2.0M CsCl. Samples were then analyzed by polyacrylamide gel electrophoresis on a 7–14% linear gradient gel in the presence of 0.1% sodium dodecylsulfate followed by staining with silver. Protein samples contained 1.4 µg whole virus (lane 1), 0.3 µg whole virus (lane 2), 5 µl of RNP cores (lane 3) and 25 µl RNA polymerase (lane 4). Known assignments of the proteins are indicated at the left.

Figure 2:
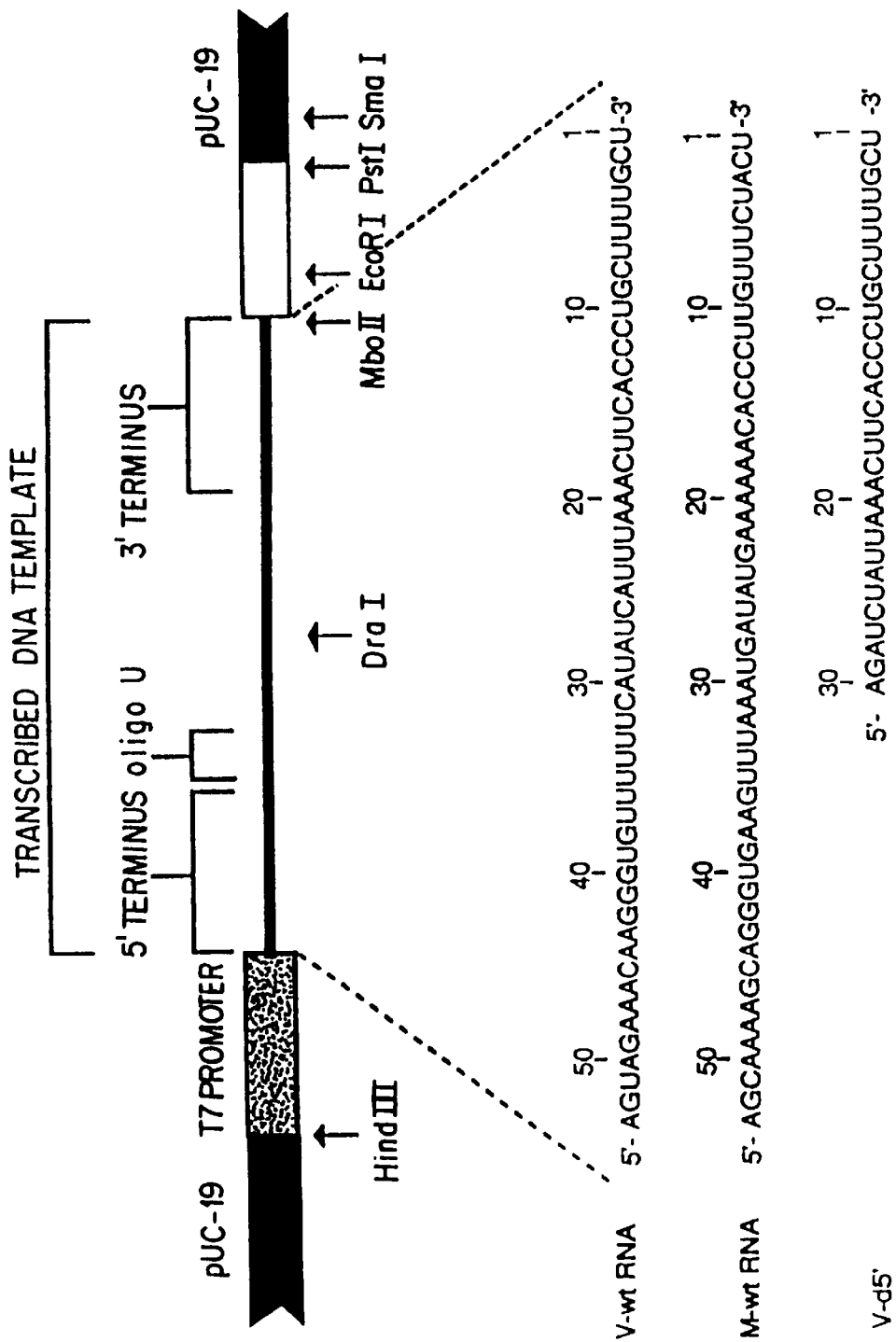

FIG. 2. Plasmid constructs used to prepare RNA templates. The plasmid design is depicted with the solid box representing pUC-19 sequences, the hatched box represents the truncated promoter specifically recognized by bacteriophage T7 RNA polymerase, the solid line represents the DNA which is transcribed from plasmids which have been digested with MboII. The white box represents sequences encoding the recognition sites for MboII, EcoRI and PstI, in that order. Sites of cleavage by restriction endonucleases are indicated. Beneath the diagram, the entire sequences of RNAs which result from synthesis by T7 RNA polymerase from MboII-digested plasmid are given. The V-wt RNA has the identical 5' and 3' termini as found in RNA segment 8 of influenza A viruses, separated by 16 "spacer" nucleotides. The RNA, M-wt, represents the exact opposite stand, or "message-sense", of V-wt. Restriction endonuclease sites for DraI EcoRI, PstI and SmaI are indicated. T7 transcripts of plasmids cleaved by these enzymes result in, respectively, 32, 58, 66 and 91 nucleotide long RNAs. The sequences of V-d5' RNA are indicated. The plasmid design is essentially the same as that used for the V-wt RNA except for the minor changes in the "spacer" sequence. The point mutants of V-d5' RNAs which were studied are indicated in Table I.

FIG. 3. Analysis of products of influenza viral polymerase. FIG. 3A: Polymerase reaction mixtures containing 0.4 mM ApG (lane 2) or no primer (lane 3) were electrophoresed on 8% polyacrylamide gels containing 7.7M urea. FIG. 3B: The nascent RNA is resistant to single-stranded specific nuclease S1. Following the standard polymerase reaction, the solutions were diluted in nuclease S1 buffer (lane 1) and enzyme was added (lane 2). As control for S1 digestion conditions, radioactively labeled single-stranded V-wt RNA was treated with nuclease S1 (lane 3) or with buffer alone (lane 4). FIG. 3C: Ribonuclease T1 analysis of gel-purified reaction products. The reaction products of the viral polymerase using the V-wt RNA template was subjected to electrophoresis on an 8% polyacrylamide gel. The 53 nt band and the smaller transcript were excised and eluted from the gel matrix. These RNAs were digested with RNAse T1 and analyzed by electrophoresis on a 20% polyacrylamide gel containing 7.7M urea. For comparison, T7 transcripts of M-wt and V-wt RNAs which had been synthesized in the presence of $\alpha$-$^{32}$P-UTP were also analyzed with RNAse T1. The predicted radiolabeled oliognucleotides of the control RNAs are indicated. Lane 1, 53 nucleotide full length (FL) product; lane 2, 40–45 nucleotide smaller (Sm) RNA product; lane 3, M-wt RNA labeled by incorporation of $^{32}$P-MP; and lane 4, V-wt RNA labeled as in lane 3.

Figures 4A, 4B, 4C:
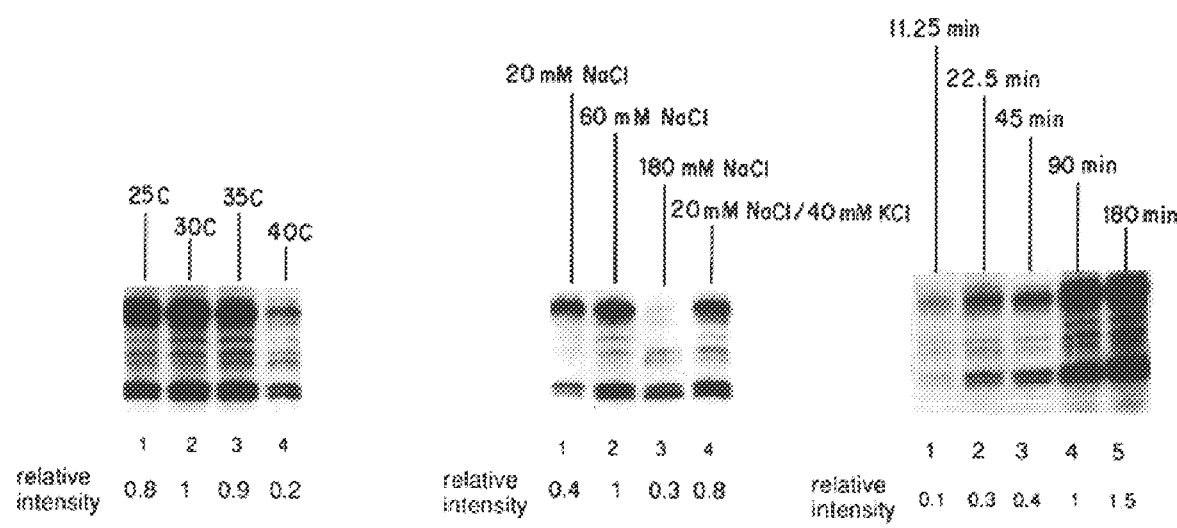

FIG. 4. Optimal reaction conditions for the viral polymerase. FIG. 4A: Reactions with V-wt template were assembled on ice and then incubated at the indicated temperatures for 90 minutes. FIG. 4B: Reactions with the V-wt template were prepared in parallel with the indicated NaCl or KCl concentrations and were incubated at 30° C. for 90 minutes. FIG. 4C: A single reaction with the V-wt template was incubated at 30° C., and at the indicated times, samples were removed and immediately processed by phenol-chloroform extraction. All gels contained 8% polyacrylamide with 7.7M urea.

Figure 5A:
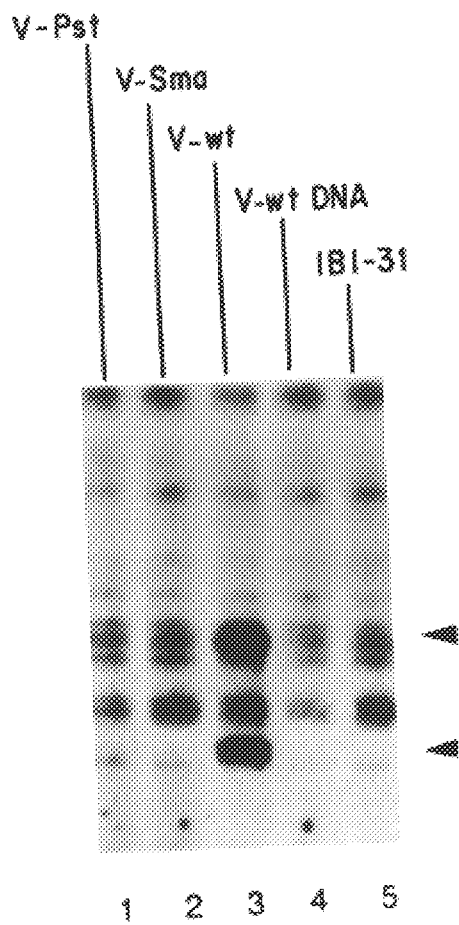
Figure 5B:
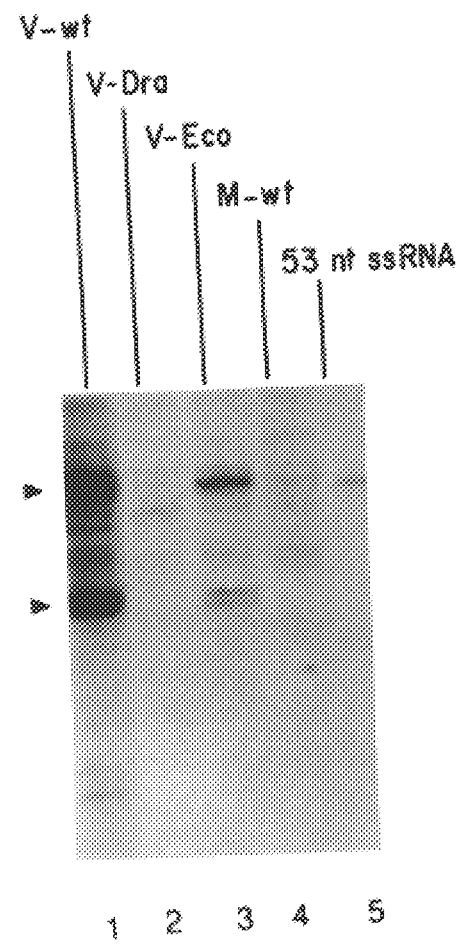

FIG. 5. Template specificity of the viral polymerase. FIG. 5A: The viral polymerase reaction requires 3' terminal promoter sequences. Different template RNAs were used in reactions under standard conditions. Lane 1, the V-Pst RNA, which is identical to V-wt except it has a 13 nt extension at the 3' end; lane 2, V-Sma RNA, which has a 38 nt extension at the 3' end; lane 3, V-wt RNA; lane 4, a DNA polynucleotide with identical sequence as the V-wt RNA; lane 5, and 80 nt RNA generated by bacteriophage T3 RNA polymerase transcription of a pIBI-31 plasmid digested with HindIII. The autoradiograph was overexposed in order to emphasize the absence of specific reaction products when these other templates were used. FIG. 5B: 10 ng of each template RNA were incubated with the viral polymerase and the products were then subjected to electrophoresis on 8% polyacrylamide gels containing 7.7M urea. Lane 1, V-wt RNA; lane 2, V-Dra RNA; lane 3, V-Eco RNA; lane 4, M-wt RNA are shown; and lane 5, a 53nt marker oligonucleotide.

For the exact sequence differences refer to FIG. 2 and Section 6.1 et seq.

Figure 6:
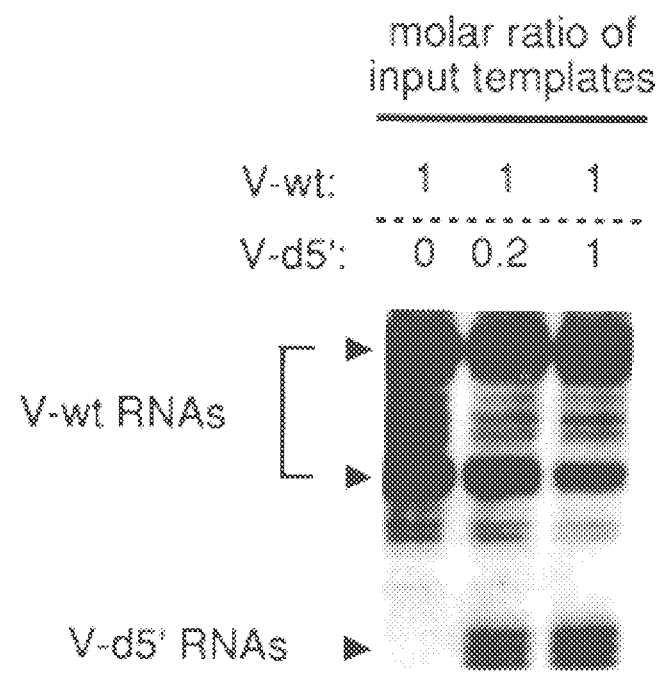

FIG. 6. The RNA promoter does not require a terminal panhandle. Polymerase reaction using two template RNAs. Each reaction contained 5 ng of V-wt RNA. As a second template the reactions contained 0 ng (lane 1), 0.6 ng (lane 2), and 3.0 ng (lane 3) of V-d5' RNA. The resulting molar ratios are as indicated in the figure. The reaction products were analyzed on an 8% polyacrylamide gel in the presence of 7.7M urea. Following densitometry analysis of autoradiographs, the relative intensity of each peak was corrected for the amount of radioactive UMP which is incorporated in each product.

Figure 7:
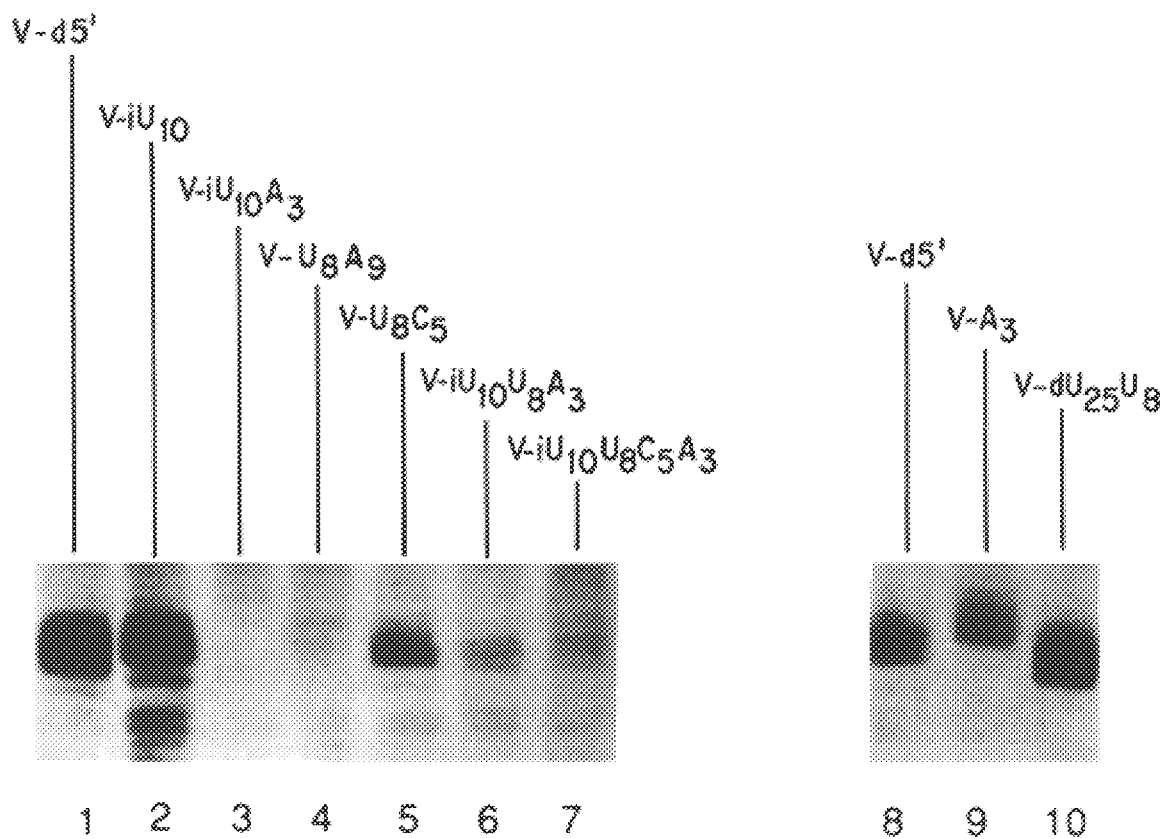

FIG. 7. Specificity of promoter sequences. RNAs which lacked the 5' terminus and contained point mutations (Table II) were compared with V-d5' RNA in standard polymerase reactions. The right panel is from a separate reaction set. Quantitative comparisons is outlined in Table II.

Figure 8A:
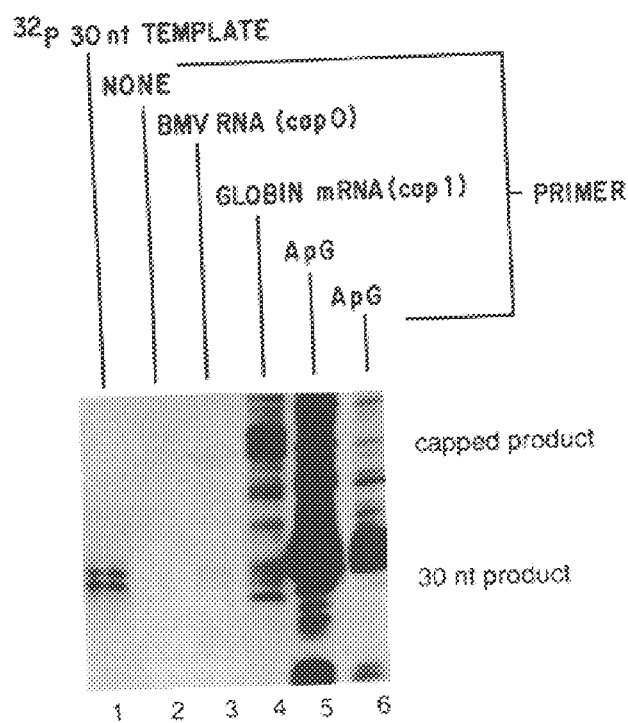
Figure 8B:
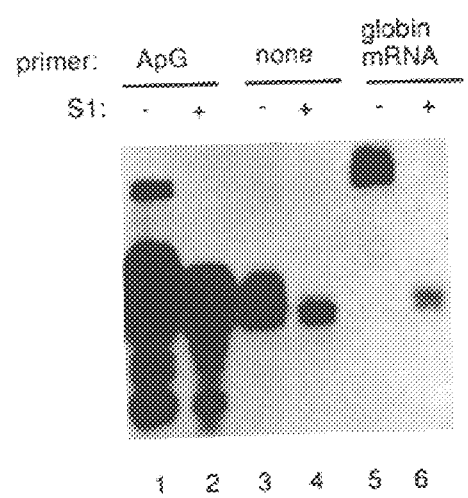

FIG. 8. High concentration polymerase preparations are active in cap-endonuclease primed and in primeness RNA synthesis reactions. FIG. 8A: Primer specificity of the high concentration enzyme. Radioactively synthesized 30 nt template is in lane 1. Reactions using 20 ng of V-d5' RNA and 5 µl of viral polymerase contained as primer: no primer (lane 2); 100 ng BMV RNA (De and Banerjee, 1985, Biochem. Biophys. Res. Commun. 6: 40–49) containing a cap 0 structure (lane 3); 100 ng rabbit globin mRNA, containing a cap 1 structure, (lane 4); and 0.4 mM ApG (lane 5). A lighter exposure of lane 5 is shown as lane 6. FIG. 8B: Nuclease S1 analysis of gel-purified RNAs. Products from reactions using as primer ApG (lanes 1 and 2); no primer (lanes 3 and 4); or globin mRNA (lanes 5 and 6) were electrophoresed in the absence of urea and the appropriate gel piece was excised and the RNA was eluted. This RNA was then digested with nuclease S1 (lanes 2, 4, and 6) and the products were denatured and analyzed on an 8% polyacrylamide gel containing 7.7M urea.

Figure 9:
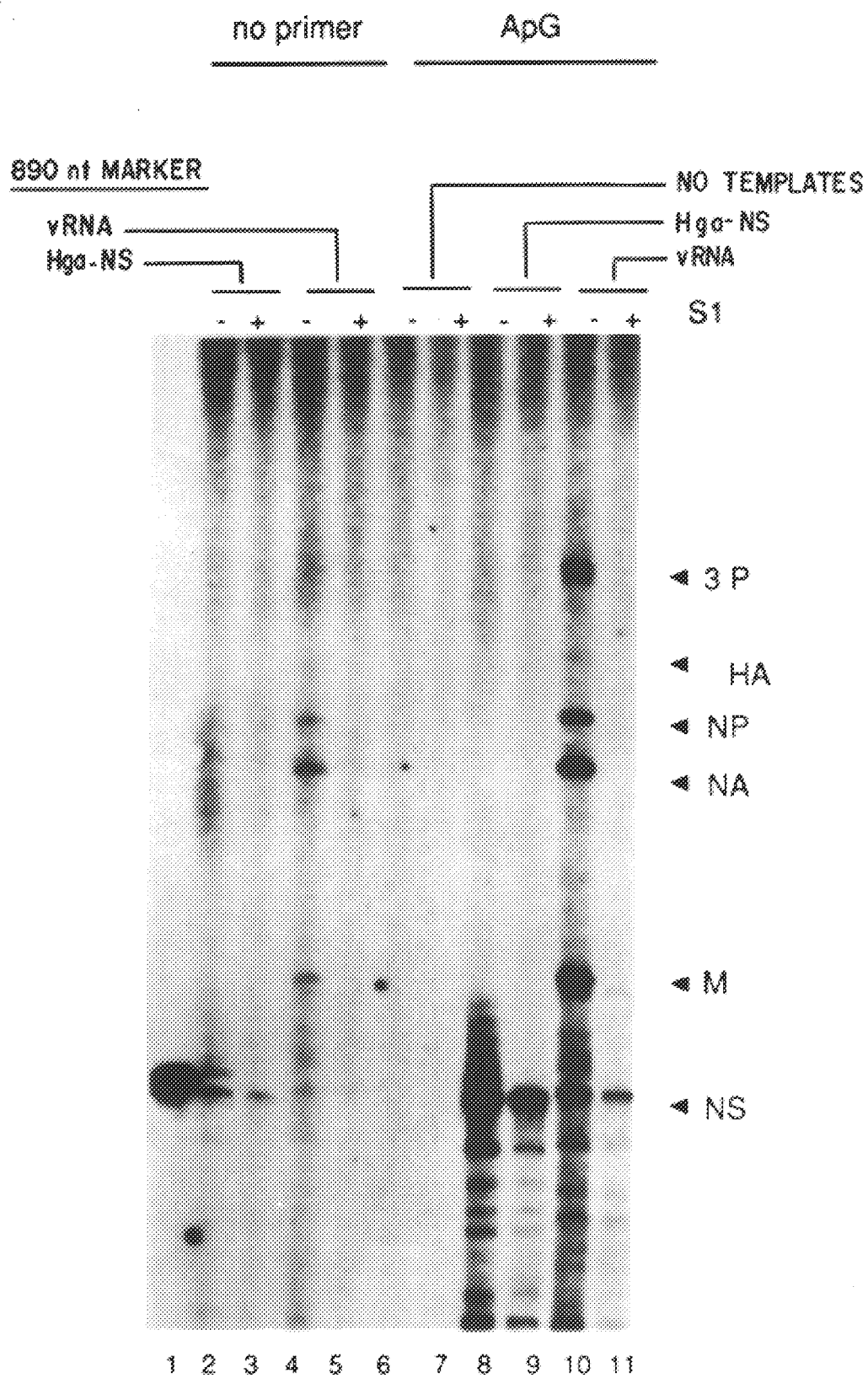

FIG. 9. Genomic length RNA synthesis from reconstituted RNPs. Reaction products using 10 µl of polymerase and as template 890 nt RNA identical to the sequence of segment 8 of virus A/WSN/33 and RNA extracted from A/PR/8/34 virus were analyzed on a 4% polyacrylamide gel containing 7.7M urea. In lane 1, the 890 nt template synthesized radioactively by T7 RNA polymerase is shown. The 890 nt plasmid-derived RNA was used as template in lanes 2, 3, 8 and 9. RNA extracted from virus was used as template in lanes 4, 5, 10 and 11. No template was used in lanes 6 and 7. No primer was used in lanes 2 to 5, and ApG was used as primer in lanes 6 to 11. Reaction products were treated with nuclease S1 in lanes 3, 5, 7, 9 and 11.

Figure 10:
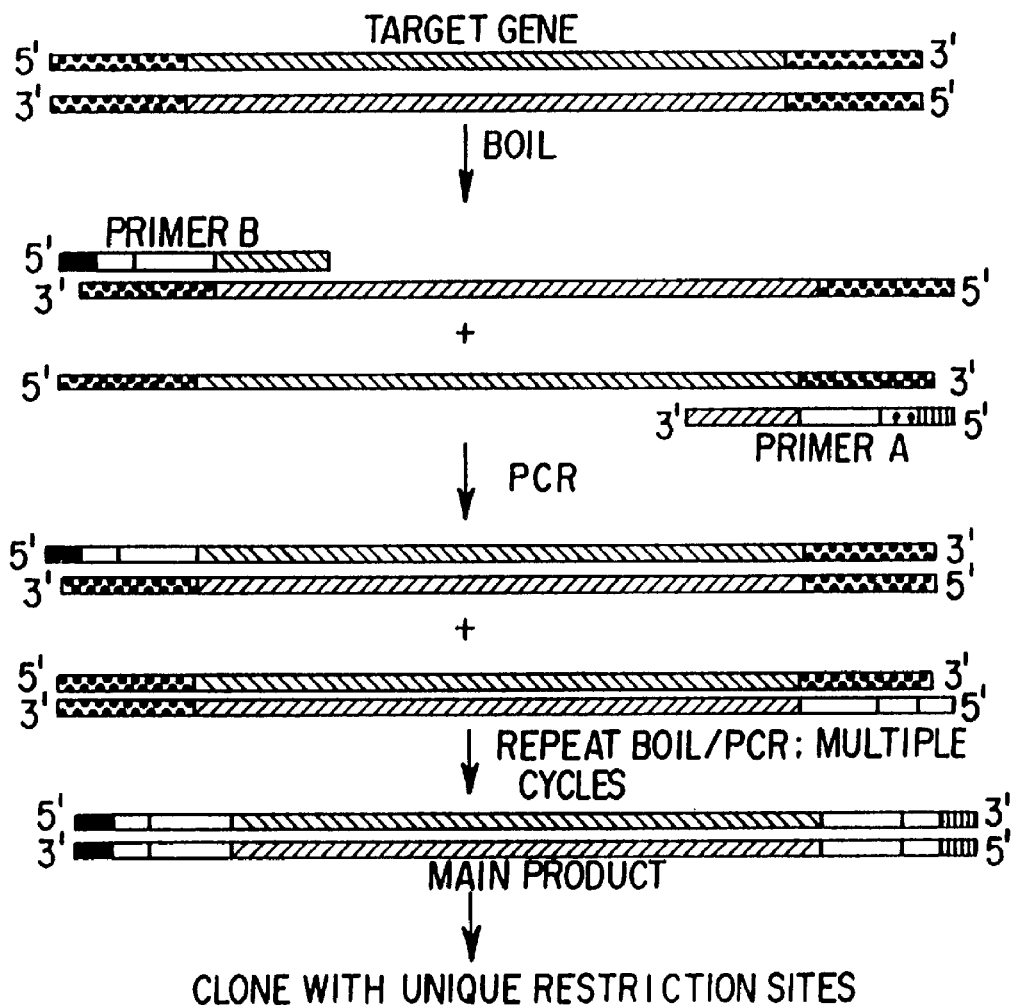

FIG. 10. Diagrammatic representation of a PCR-directed mutagenesis method which can be used to replace viral coding sequences within viral gene segments.

Figure 11:
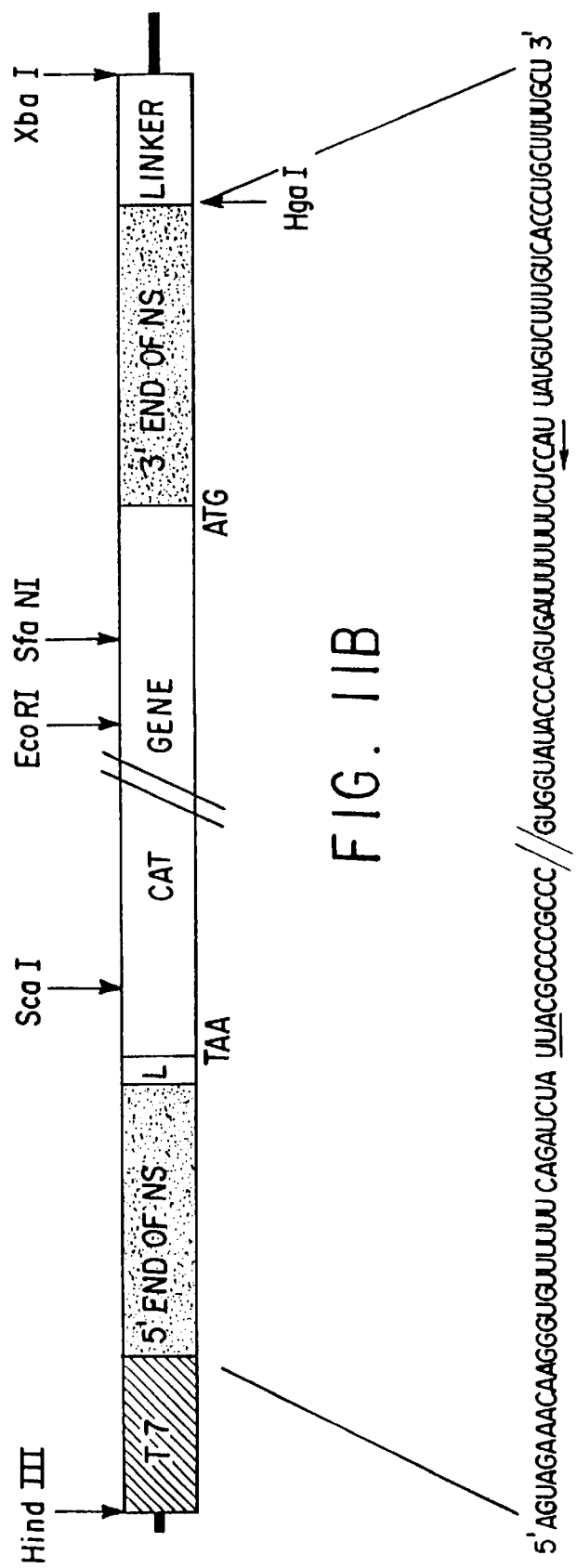

FIG. 11. (A). Diagrammatic representation of relevant portions of pIVCAT1. The various domains are labeled and are, from left to right; a truncated T7 promoter; the 5' nontranslated end of influenza A/PR/8/34 virus segment 8 (22 nucleotides); 8 nucleotides of linker sequence; the entire CAT gene coding region (660 nucleotides) the entire 3' nontranslated end of influenza A/PR/8/34 virus segment 8 (26 nucleotides); and linker sequence containing the HgaI restriction enzyme site. Relevant restriction enzyme sites and start and stop sites for the CAT gene are indicated. (B) The 716 base RNA product obtained following HgaI digestion and transcription of pIVACAT1 by T7 RNA polymerase. Influenza viral sequences are indicated by bold letters, CAT gene sequences by plain letters, and linker sequences by italics. The triplets—in antisense orientation—representing the initiation and termination codons of the CAT gene are indicated by arrow and underline, respectively.

Figure 12:
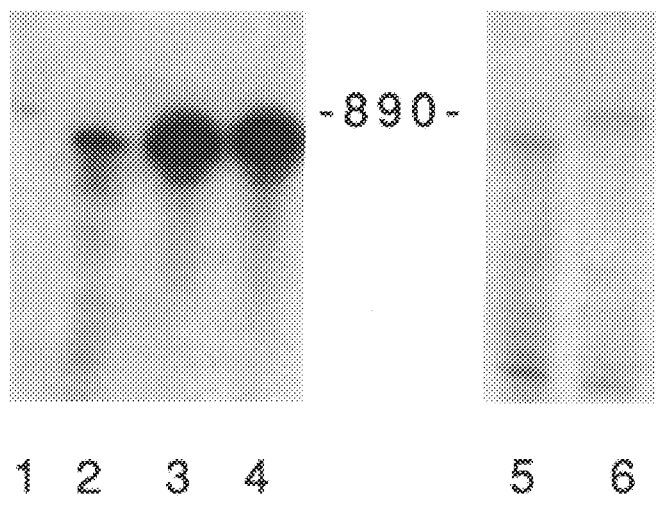

FIG. 12. RNA products of T7 polymerase transcription and in vitro influenza virus polymerase transcription. Lanes 1–4: polyacrylamide gel analysis of radiolabeled T7 polymerase transcripts from pIVACAT1, and pHgaNS. Lanes 5 and 6: Polyacrylamide gel analysis of the radiolabeled products of in vitro transcription by purified influenza A polymerase protein using unlabeled 1VACAT1 RNA and HgaNS RNA templates. Lane 1: HgaNS RNA of 80 nt. Lanes 2–4: different preparations of IVACAT1 RNA. Lane 5: viral polymerase transcript of IVACAT1 RNA. Lane 6: viral polymerase transcript of HgaNS RNA.

Figure 13:
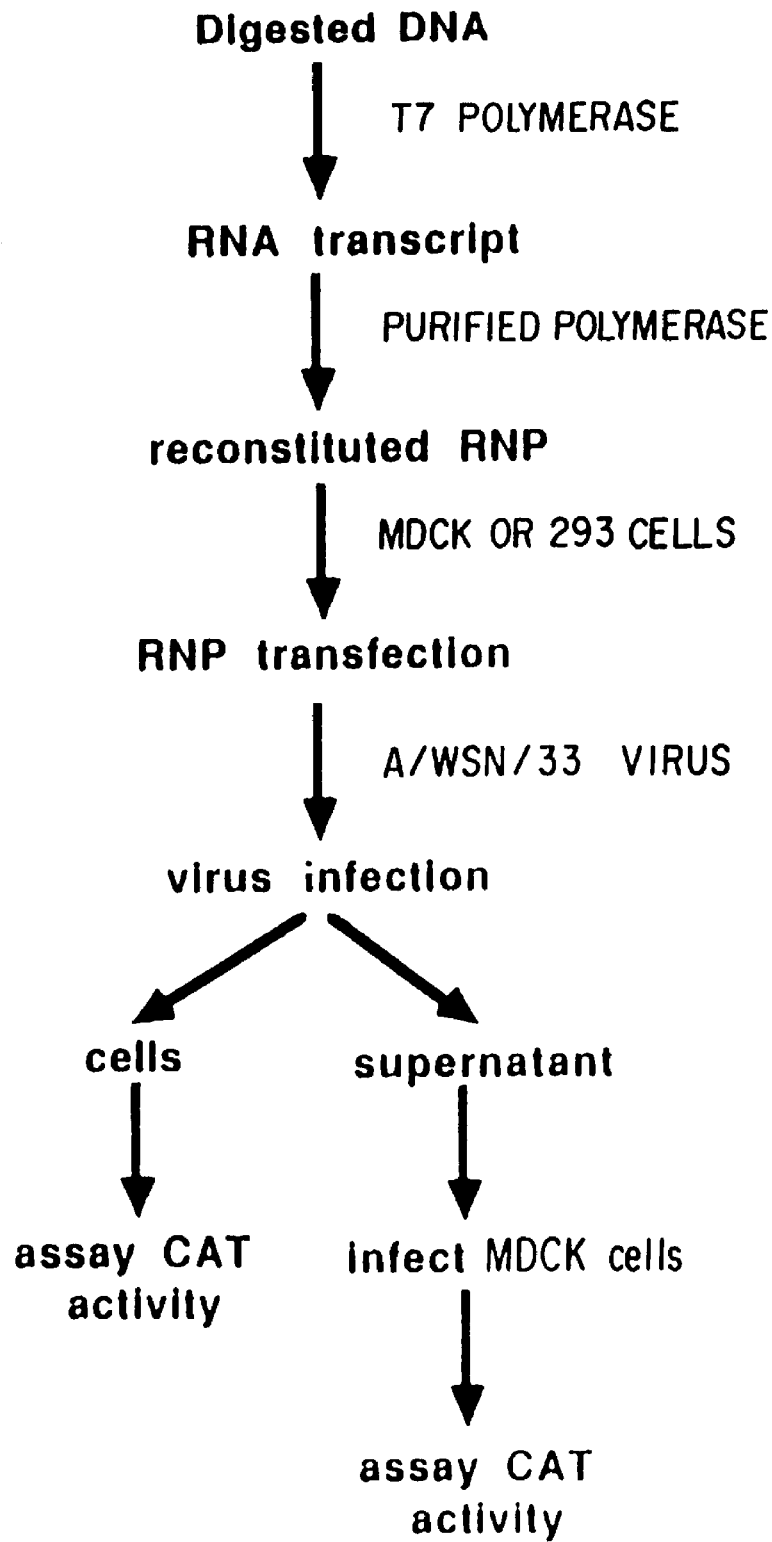

FIG. 13. Schematic of the RNP-transfection and passaging experiments.

FIG. 14. CAT assays of cells RNP-transfected with IVA-CAT1 RNA. (A) Time course of RNP-transfection in 293 cells. Cells were transfected at −1 hour with the recombinant RNP and infected with virus at 0 hour. Cells were harvested at the indicated time points and assayed for CAT activity. (B) Requirements for RNP-transfection of 293 cells Parameters of the reaction mixtures were as indicated. (C) RNP-transfection of MDCK cells. MDCK cells were transfected with IVACAT1 RNA-polymerase at either −1 hour or +2 hours relative to virus infection. Cells were harvested and CAT activity assayed at the indicated times. Components/conditions of the reaction were as indicated. "Time" indicates the time point of harvesting the cells. T=0 marks the time of addition of helper virus. "RNA" represents the IVACAT1 RNA. "Pol" is the purified influenza A/PR/8/34 polymerase protein complex. "WSN" indicates the influenza A/WSN/33 helper virus. "Pre-Inc." indicates preincubation of RNA and polymerase in transcription buffer at 30° C. for 30 min. "RNP transfection" indicates the time of RNP transfection relative to virus infection. "+/−" indicate presence or absence of the particular component/feature. "C" indicates control assays using commercially available CAT enzyme (Boehringer-Mannheim).

Figure 15:
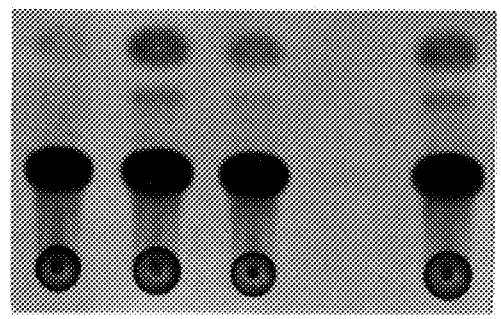

FIG. 15. CAT activity in MDCK cells infected with recombinant virus. Supernatant from RNP-transfected and helper virus-infected MDCK cells was used to infect fresh MDCK cells. The inoculum was removed 1 hour after infection, cells were harvested 11 hours later and CAT activity was assayed. Lane 1: extract of cells infected with helper virus only. Lane 2: extract of cells infected with 100 µl of supernatant from RNP-transfected and helper virus-infected MDCK cells. Lane 3: Supernatant (80 µl) of cells from lane 2. Lane 4: Same as lane 2 except that helper virus (MOI 4) was added to inoculum. In contrast to experiments shown in FIG. 4, the assays contained 20 µl of $^{14}$C chloramphenicol.

Figure 16:
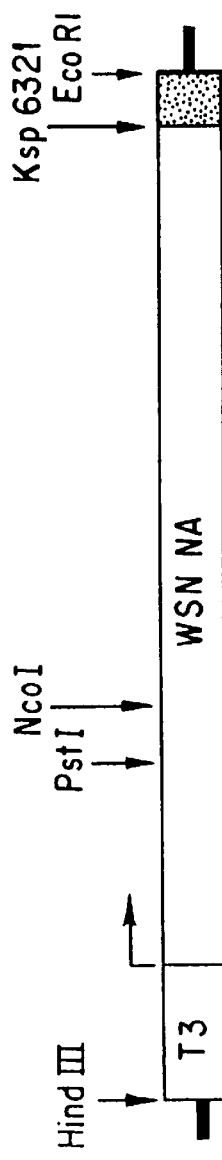

FIG. 16. Diagram of relevant portions of the neuraminidase (NA) gene contained in plasmids used for transfection experiments. The pUC19 derived plasmid pT3NAv contains the influenza A/WSN/33 virus NA gene and a truncated promoter specifically recognized by bacteriophage T3 RNA polymerase. The T3 promoter used is truncated such that the initial transcribed nucleotide (an adenine) corresponds to the 5' adenine of the WSN NA gene. At the 3' end of the cDNA copy of the NA gene, a Ksp632I restriction enzyme site was inserted such that the cleavage site occurs directly after the 3' end of the NA gene sequence. A 1409 nucleotide long transcript was obtained following Ksp632I digestion and transcription by T3 RNA polymerase of PT3NAv (as described in Section 8.1, infra). The 15 5' terminal nucleotides, the 52 nucleotides corresponding to the region between the restriction endonuclease sites NcoI and PstI and the 12 3' terminal nucleotides are shown. The transcript of pT3NAv mut 1 is identical to that of pT3NAv except for a single deletion, eleven nucleotides downstream from the 5' end of the wild type RNA. The transcript of the pT3NAv mut 2 is identical to that of pT3NAv except for 5 mutations located in the central region (indicated by underline). These five mutations do not change the amino acid sequence in the open reading frame of the gene. The serine codon UCC at position 887–889 (plus sense RNA) was replaced with the serine codon AGU in the same frame. The numbering of nucleotides follows Hiti et al., 1982, J. Virol., 41: 730–734.

Figure 17:
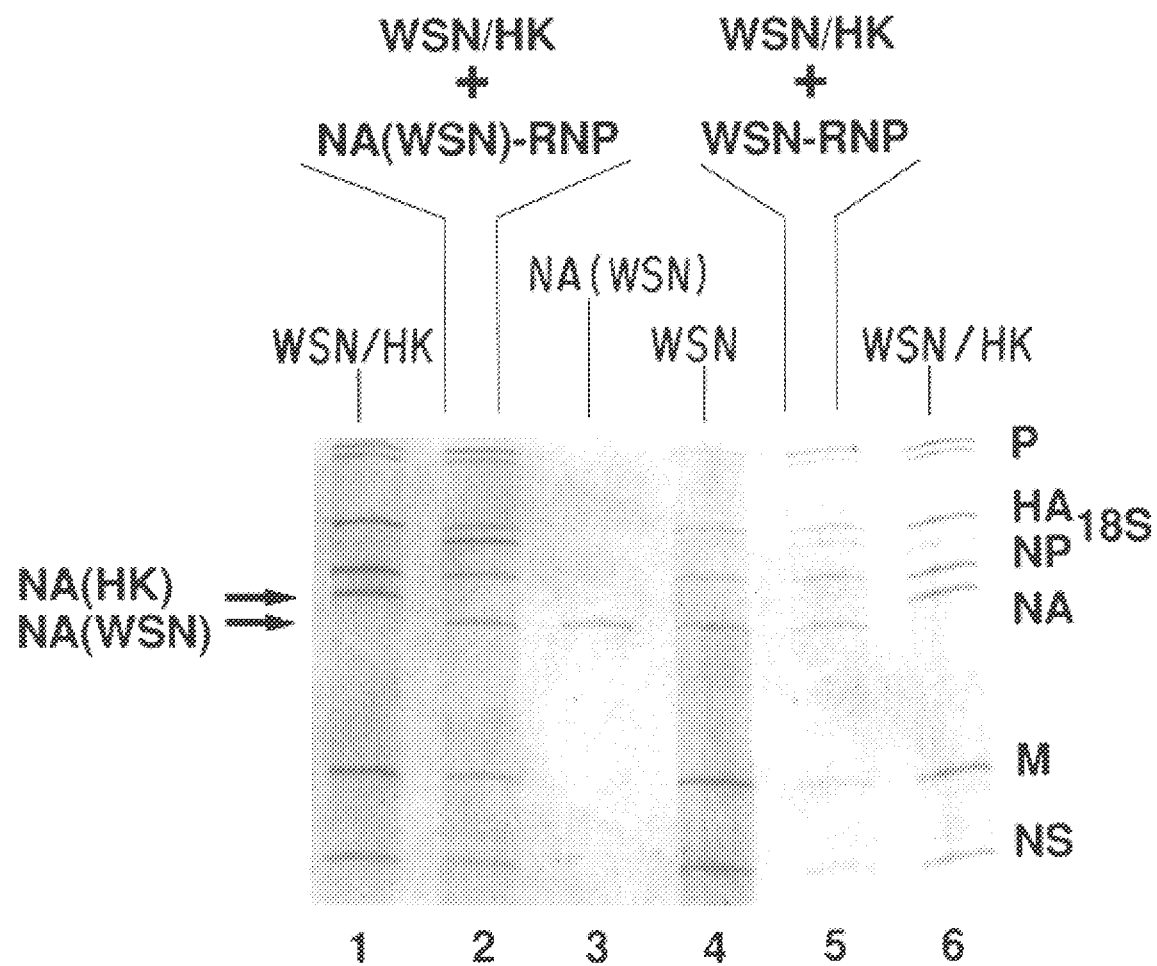

FIG. 17. Polyacrylamide gel electrophoresis of RNAs purified from rescued influenza viruses. RNA transcripts of pT3NAs (FIG. 16) of phenol-extracted RNA derived from influenza A/WSN/33 virus was mixed with purified polymerase preparations following the protocol described in Section 6.1.1, infra. These reconstituted RNPs were then transfected into MDBK cells which had been infected one hour earlier with WSN-HK helper virus. The medium, containing 28 µg/ml plasminogen, was harvested after 16 hours and virus was amplified and plaqued on MDBK cells in the absence of protease. Virus obtained from plaques was then further amplified in MDBK cells and RNA was phenol-extracted from purified virus preparations as described in Sections 6.1 et seq. and 7.1 et seq. RNAs were separated on 2.8% polyacrylamide-0.075 % bisacrylamide gels containing 7.7M urea in TBE buffer and visualized by silverstaining as described in Section 6.1 et seq. Lanes 1 and 6: WSN-HK virus RNA. Lane 2: RNA of virus which was rescued from MDBK cells following RNP-transfection with pT3NAv derived NA RNA and infection with helper virus WSN-HK. Lane 3: NA RNA transcribed in vitro from pT3NAv. Lane 4: RNA of control WSN virus. Lane 5: RNA of virus which was rescued from MDBK cells following RNP-transfection with phenol-extracted WSN virus RNA and infection with helper virus WSN-HK.

Figure 18:
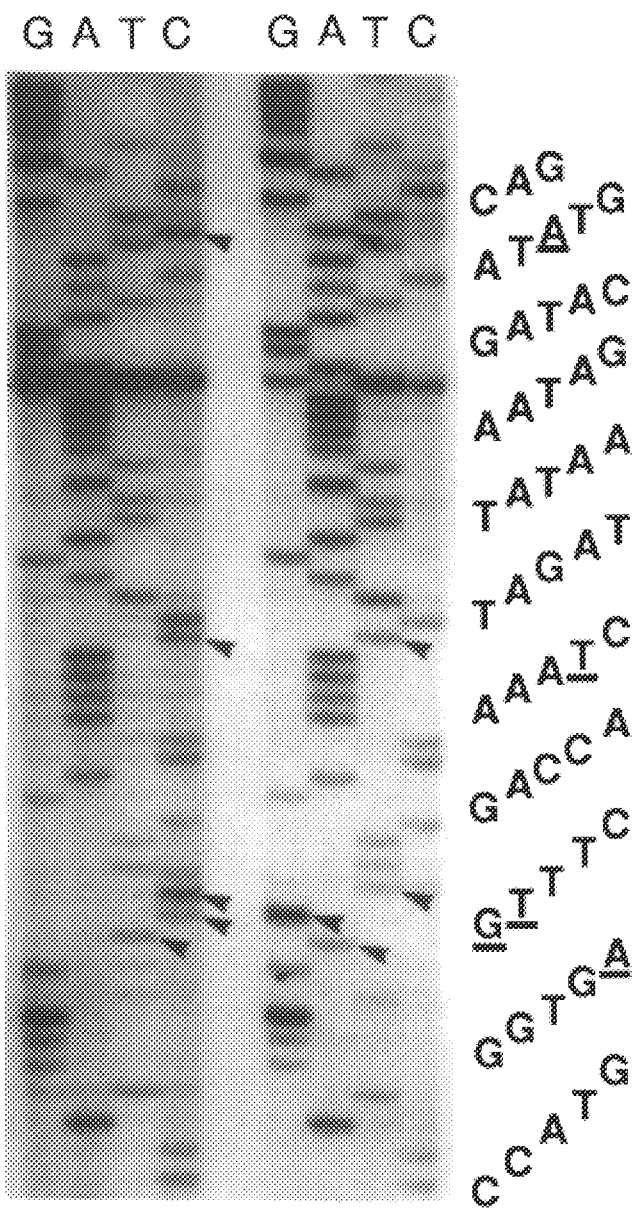

FIG. 18. Sequence analysis of RNA obtained from rescued influenza virus containing five site-specific mutations. Following infection with the WSN-HK helper virus, MDBK cells were RNP-transfected with T3NAv mut 2 RNA which was obtained by transcription from pT3NAv mut 2. Following overnight incubation in the presence of 28 µg/ml plasminogen, medium was used for propagation and plaquing on MDBK cells in the absence of protease. Virus from plaques was then amplified and RNA was obtained following phenol-extraction of purified virus. Rescue of the mutant NA gene into virus particles was verified through direct RNA sequencing using 5'-TACGAGGAAATGTTCCTGTTA-3' as primer (corresponding to position 800–819; Hiti et al., J. Virol., 41: 730–734) and reverse transcriptase (Yamashita et al., 1988, Virol. 163: 112–122). Sequences shown correspond to position 878–930 in the NA gene (Hiti et al., J. Virol. 41: 730–734). The arrows and the underlined nucleotides indicate the changes in the mutant RNA compared to the wild type RNA. Left: Control RNA obtained from influenza A/WSN/33 virus. Right: RNA of mutant virus rescued from MDBK cells which were RNP-transfected with T32NAv mut 2 RNA and infected with helper virus WSN-HK.

FIG. 19. CAT expression in vaccinia virus-infected/IVACAT-1 RNP transfected cells. Approximately $10^6$ mouse C127 cells in 35 mm dishes were infected with mixtures of recombinant vaccinia viruses (Smith et al., 1986) at an M.O.I. of approximately 10 for each vector. After 1.5 hours, synthetic IVACAT-1 RNP was transfected into the virus-infected cells as described (Lutjyes et al., 1989). Cells were incubated overnight, harvested and assayed for CAT activity according to standard procedures (Gorman et al., 1982). The assays contained 0.05 uCl [$^{14}$C] chloramphenicol, 20 ul of 40 mM acetyl-CoA (Boehringer and 50 ul of cell extracts in 0.25 M Tris buffer (pH 7.5). Incubation times were approximately 4 hours. The labels under the lane numbers indicate the treatment of cells. Lanes 1-control; 2-naked RNA transfection (no polymerase added), no helper virus infection; 3-RNP transfection, no helper virus; 4-RNP transfection, influenza virus as helper; Lanes 5–11-RNP transfection, vaccinia virus vectors as helper viruses express the indicated influenza virus proteins.

FIG. 20. Test of various cell lines. A) Cells were infected with vaccinia vectors expressing the PB2, PB1 and PA proteins (Lanes 1,3,5,7) or the PB2, PB1, PA and NP proteins (Lanes 2,4,6,8), transfected with IVACAT-1 RNP and examined for CAT activity as described. Lanes 1,2: Maden-Darby Canine Kidney (MDCK) cell; 3,4: Hela cells, 5,6: 293 cells (Graham et al., 1977 J. Gen. Virol., 36: 59–72); 7,8 L cells. B) Cell line 3 PNP-4 was used as host cell. Shown under each lane is the influenza viral proteins expressed in each sample. C) 293 cells were infected with the four required vaccinia and transfected with synthetic RNP made using IVA-CAT-I (lane 1) or IVA-CAT-2 (lane 2) RNA. After overnight incubation, cells were harvested and CAT assays were performed.

Figure 21:
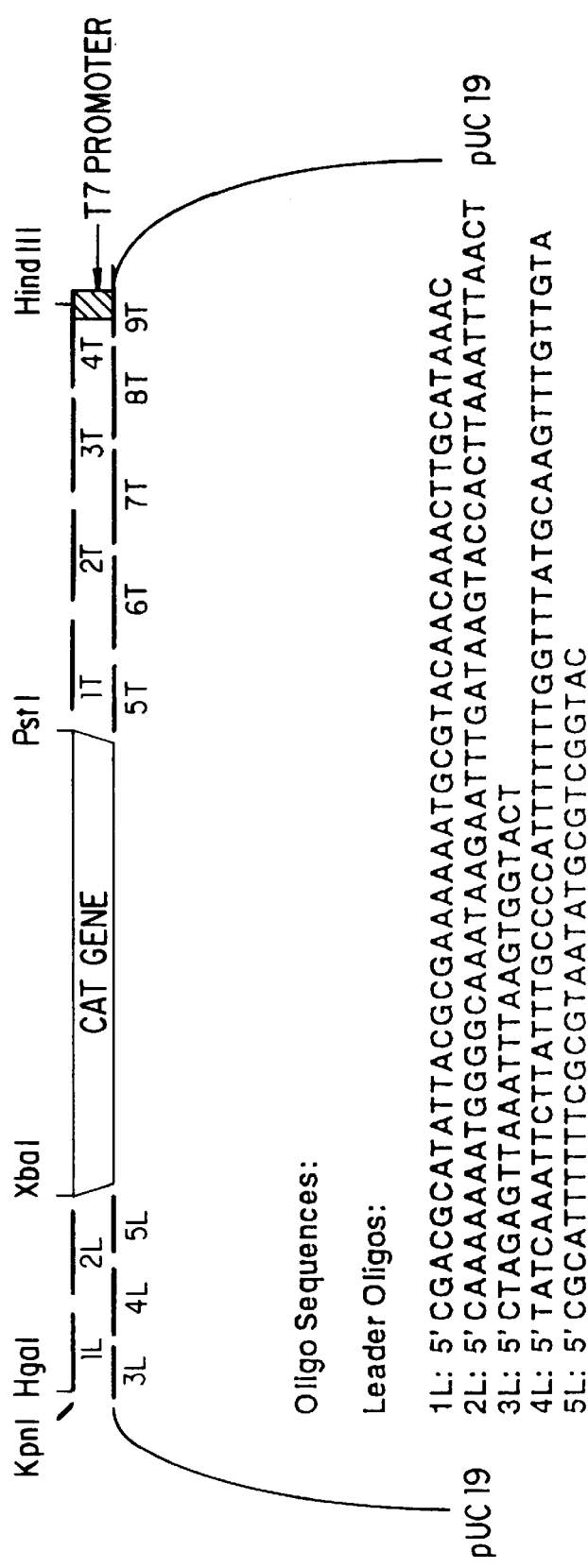

FIG. 21. Schematic representation of the RSV/CAT construct (pRSVA2CAT) used in rescue experiments. The approximate 100 nt long leader and 200 nt long trailer regions of RSV were constructed by the controlled annealing of synthetic oligonucleotides containing partial overlapping complementarity. The overlapping leader oligonucleotides are indicated by the 1L–5L shown in the construct. The overlapping trailer nucleotides are indicated by the 1T–9T shown in the construct. The nucleotide sequences of the leader and trailer oligonucleotides are shown below the construct. The fully formed leader and trailer DNAs were ligated into purified CAT gene DNA at the indicated XbaI and PstI sites respectively. This entire construct was then ligated into KpnI/HindIII digested pUC19. The inclusion of a T7 promoter sequence and a HgaI site flanking the trailer and leader sequences respectively allowed in vitro synthesis of RSV/CAT RNA transcripts containing the precise genomic sequence 3' and 5' ends.

Figure 22:
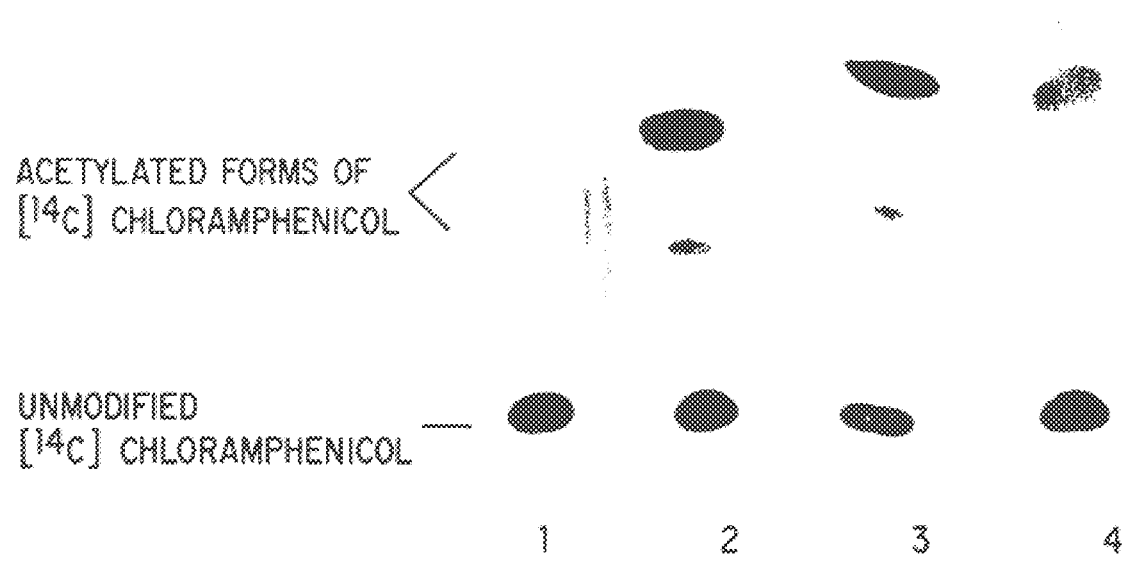

FIG. 22. Thin layer chromatogram (TLC) showing the CAT activity present in 293 cell extracts following infection and transfection with RNA transcribed from the RSV/CAT construct shown in FIG. 1. Confluent monolayers of 293 cells in 6-well plates (~$10^6$ cells) were infected with either RSV A2 or B9320 at an m.o.i. of 0.1–1.0 pfu cell$^{31\ 1}$. At 1 hour post infection the cells were transfected with 5–10 µg of CAT/RSV using the Transfectace™ protocol of Gibco BRL. AT 24 hours post infection the infected/transfected monolayers were harvested and processed for subsequent CAT assay according to Current Protocols in Molecular Biology, Vol. 1, Chapter 9.6.2; Gorman, et al., (1982) Mol. Cell. Biol. 2:1044–1051.

Lanes 1, 2, 3, and 4 show the CAT activity present in (1) uninfected 293 cells, transfected with CAT/RSV RNA, (2) RSV-A2 infected 293 cells, transfected with CAT/RSV RNA, (3) RSV-B9320 infected 293 cells transfected with CAT/RSV RNA, (4) RSV-A2 infected 293 cells, co-infected with supernatant from (2) above. The CAT activity observed in each lane was produced from ⅕ of the total cellular extract from $10^6$ cells.

FIG. 23. Schematic representation of the RSV strain A2 genome showing the relative positions of the primer pairs used for the synthesis of cDNAs comprising the entire genome. The endonuclease sites used to splice these clones together are indicated; these sites were present in the native RSV sequence and were included in the primers used for cDNA synthesis. Approximately 100 ng of viral genomic RNA was used in RT/PCR reactions for the separate synthesis of each of the seven cDNAs. The primers for the first and second strand cDNA synthesis from the genomic RNA template are also shown. For each cDNA, the primers for the first strand synthesis are nos. 1–7 and the primers for the second strand sythesis are nos. 1'–7'.

5. DESCRIPTION OF THE INVENTION

This invention relates to the construction and use of recombinant negative strand viral RNA templates which may be used with viral RNA-directed RNA polymerase to express heterologous gene products in appropriate host cells and/or to rescue the heterologous gene in virus particles. The RNA templates may be prepared by transcription of appropriate DNA sequences using a DNA-directed RNA polymerase such as bacteriophage T7, T3 or the Sp6 polymerase. Using influenza, for example, the DNA is constructed to encode the message- sense of the heterologous gene sequence flanked upstream of the ATG by the complement of the viral polymerase binding site/promoter of influenza, i.e., the complement of the 3'-terminus of a genome segment of influenza. For rescue in virus particles, it may be preferred to flank the heterologous coding sequence with the complement of both the 3'-terminus and the 5'-terminus of a genome segment of influenza. After transcription with a DNA-directed RNA polymerase, the resulting RNA template will encode the negative polarity of the heterologous gene sequence and will contain the vRNA terminal sequences that enable the viral RNA-directed RNA polymerase to recognize the template.

The recombinant negative sense RNA templates may be mixed with purified viral polymerase complex comprising viral RNA-directed RNA polymerase proteins (the P proteins) and nucleoprotein (NP) which may be isolated from RNP cores prepared from whole virus to form "recombinant RNPs" (rRNPs). These rRNPs are infectious and may be used to express the heterologous gene product in appropriate host cells or to rescue the heterologous gene in virus particles by cotransfection of host cells with the rRNPs and virus. Alternatively, the recombinant RNA templates may be used to transfect transformed cell lines that express the RNA-directed RNA polymerase proteins allowing for complementation.

The invention is demonstrated by way of working examples in which RNA transcripts of cloned DNA containing the coding region—in negative sense orientation—of the chloramphenicol acetyltransferase (CAT) gene flanked by the 22 5' terminal and the 26 3' terminal nucleotides of the influenza A/PR/8/34 virus NS RNA were mixed with isolated influenza A virus polymerase proteins. This reconstituted ribonucleoprotein (RNP) complex was transfected into MDCK (or 293) cells, which were infected with influenza virus. CAT activity was negligible before and soon after virus infection, but was demonstrable by seven hours post virus infection. When cell supernatant containing budded virus from this "rescue" experiment was used to infect a new monolayer of MDCK cells, CAT activity was also detected, suggesting that the RNA containing the recombinant CAT gene had been packaged into virus particles. These results demonstrate the successful use of recombinant negative strand viral RNA templates and purified RNA-dependent RNA polymerase to reconstitute recombinant influenza virus RNP. Furthermore, the data suggest that the 22 5' terminal and the 26 3' terminal sequences of the influenza A virus RNA are sufficient to provide the signals for RNA transcription, A replication and for packaging of RNA into influenza virus particles.

Using this methodology we also demonstrated the rescue of synthetic RNAs, derived from appropriate recombinant plasmid DNAs, into stable and infectious influenza viruses. In particular, RNA corresponding to the neuraminidase (NA) gene of influenza A/WSN/33 virus (WSN) was transcribed in vitro from plasmid DNA and, following the addition of purified influenza virus polymerase complex, was transfected into MDBK cells. Superinfection with helper virus lacking the WSN NA gene resulted in the release of virus containing the WSN NA gene. We then introduced five point mutations into the WSN NA gene by cassette mutagenesis of the plasmid DNA. Sequence analysis of the rescued virus revealed that the genome contained all five mutations present in the mutated plasmid. This technology can be used to create viruses with site-specific mutations so that influenza viruses with defined biological properties may be engineered.

The ability to reconstitute RNPs in vitro allows the design of novel chimeric influenza viruses which express foreign genes. One way to achieve this goal involves modifying existing influenza virus genes. For example, the HA gene may be modified to contain foreign sequences in its external domains. Where the heterologous sequence are epitopes or antigens of pathogens, these chimeric viruses may be used to induce a protective immune response against the disease agent from which these determinants are derived. In addition to modifying genes coding for surface proteins, genes coding for nonsurface proteins may be altered. The latter genes have been shown to be associated with most of he important cellular immune responses in the influenza virus system (Townsend et al., 1985, Cell 42: 475–482). Thus, the inclusion of a foreign determinant in the NP or the NS gene of an influenza virus may—following infection—induce an effective cellular immune response against this determinant. Such an approach may be particularly helpful in situations in which protective immunity heavily depends on the induction of cellular immune responses (e.g., malaria, etc.).

Another approach which would permit the expression of foreign proteins (or domains of such proteins) via chimeric influenza viruses concerns the introduction of complete heterologous genes into the virus. Influenza virus preparations with more than eight RNA segments have previously been described (Nayak, D. et al. in Genetics of Influenza Virus, P. Palese and D. W. Kingsbury, eds., Springer-Verlag, Vienna, pp. 255–279). Thus, chimeric influenza viruses with nine or more RNA segments may be viable, and correct packaging of such chimeric viruses may readily occur.

The invention may be divided into the following stages solely for the purpose of description and not by way of limitation: (a) construction of recombinant RNA templates; b) expression of heterologous gene products using the recombinant RNA templates; and (c) rescue of the heterologous gene in recombinant virus particles. For clarity of discussion, the invention is described in the subsections below using influenza. Any strain of influenza (e.g., A, B, C) may be utilized. However, the principles may be analogously applied to construct other negative strand RNA virus templates and chimeric viruses including, but not limited to paramyxoviruses, such as parainfluenza viruses, measles viruses, respiratory syncytial virus; bunyaviruses; arena viruses; etc. Section 9 describes and exemplifies the application of these principles to the construction of respiratory syncytial virus templates and chimeric respiratory syncytial viruses. A particularly interesting virus system that can be used in accordance with the invention are the orthomyxo-like insect virus called Dhori (Fuler, 1987, Virology 160: 81–87).

5.1. Construction of the Recombinant RNA Templates

Heterologous gene coding sequences flanked by the complement of the viral polymerase binding site/promoter, e,g, the complement of 3'-influenza virus terminus, or the complements of both the 3'-and 5'-influenza virus termini may be constructed using techniques known in the art. Recombinant DNA molecules containing these hybrid sequences can be cloned and transcribed by a DNA-directed RNA polymerase, such as bacteriophage T7, T3 or the Sp6 polymerase and the like, to produce the recombinant RNA templates which possess the appropriate viral sequences that allow for viral polymerase recognition and activity.

One approach for constructing these hybrid molecules is to insert the heterologous coding sequence into a DNA complement of an influenza virus genomic segment so that the heterologous sequence is flanked by the viral sequences required for viral polymerase activity; i.e., the viral polymerase binding site/promoter, hereinafter referred to as the viral polymerase binding site. In an alternative approach, oligonucleotides encoding the viral polymerase binding site, e.g., the complement of the 3'-terminus or both termini of the virus genomic segments can be ligated to the heterologous coding sequence to construct the hybrid molecule. The placement of a foreign gene or segment of a foreign gene within a target sequence was formerly dictated by the presence of appropriate restriction enzyme sites within the target sequence. However, recent advances in molecular biology have lessened this problem greatly. Restriction enzyme sites can readily be placed anywhere within a target sequence through the use of site-directed mutagenesis (e.g., see, for example, the techniques described by Kunkel, 1985, Proc. Natl. Acad. Sci. U.S.A. 82;488). Variations in polymerase chain reaction (PCR) technology, described infra, also allow for the specific insertion of sequences (i.e., restriction enzyme sites) and allow for the facile construction of hybrid molecules. Alternatively, PCR reactions could be used to prepare recombinant templates without the need of cloning. For example, PCR reactions could be used to prepare double-stranded DNA molecules containing a DNA-directed RNA polymerase promoter (e.g., bacteriophage T3, T7 or Sp6) and the hybrid sequence containing the heterologous gene and the influenza viral polymerase binding site. RNA templates could then be transcribed directly from this recombinant DNA. In yet another embodiment, the recombinant RNA templates may be prepared by ligating RNAs specifying the negative polarity of the heterologous gene and the vital polymerase binding site using an RNA ligase. Sequence requirements for viral polymerase activity and constructs which may be used in accordance with the invention are described in the subsections below.

5.1.1. The Viral 3'-Terminus is Required for Polymerase Activity

The experiments described in Section 6 et seq., infra, are the first to define promoter sequences for a polymerase of a negative-sense RNA virus, and it was found that the specificity lies in the 3' terminal 15 nucleotides. These viral polymerase binding site sequences, as well as functionally equivalent sequences may be used in accordance with the invention. For example, functionally equivalent sequences containing substitutions, insertions, deletions, additions or inversions which exhibit similar activity may be utilized. The RNA synthesis by the viral polymerase described infra is a model for specific recognition and elongation by the influenza viral polymerase for the following reasons: (a) the polymerase has high activity when primed with ApG, a feature unique to influenza viral polymerase; (b) it has optimal activity at temperature and ionic conditions previously shown to be effective for the viral RNPs; (c) the polymerase is specific for influenza viral sequences on the model RNA templates; (d) the polymerase is active in the cap-endonuclease primed RNA synthesis which is the hallmark of the influenza viral polymerase; (e) recognition of cap donor RNA is specific to cap 1 structures; and (f) genomic RNA segments are specifically copied.

5.1.2. Terminal Panhandle is not Required for Optimal Recognition and Synthesis by the Viral Polymerase We had previously shown that the influenza vital segment RNAs base-pair at their termini to form panhandle structures. This was achieved by two methods. A cross-linking reagent derivative of psoralen covalently bound the termini of each segment in intact virus or in RNPs from infected cells (Hsu et al., 1987, Proc. Natl. Acad. Sci. USA 84: 8140–8144). The treated RNA was seen by electron microscopy to be circular, by virtue of the cross-linked termini. Similarly, the RNA termini in RNPs were found to be sensitive to ribonuclease V1, which recognizes and cleaves double-stranded RNA, and the viral polymerase was found to be bound to both termini in the panhandle conformation (Honda, et al., 1988, J. Biochem. 104: 1021–1026). In these studies the panhandle structure of the genomic RNA was shown to exist, and it was inferred to play a role in polymerase recognition. Although the template RNAs used in the examples described, were originally prepared to reveal panhandle-specific protein binding, it was found that the terminal panhandle had no obvious role in the polymerase reactions studied herein.

5.1.3. The RNA Polymerase Preparation Specifically Copies Negative Sense Templates The viral polymerase was shown to synthesize RNA with optimal efficiency if the template had the "wild-type" negative sense 3' terminus. It was shown that RNAs of unrelated sequence were not copied, and that those with extra polylinker sequences on the 3' end were much less efficiently copied. A DNA of the correct sequence was similarly unsuitable as a template. The reaction was highly specific since the M-wt template was replicated only at very low levels. Even though our source of polymerase was intact virus, this finding was very surprising since it had never been suggested that the polymerase which recognizes the viral sense RNA would not efficiently copy the plus sense strand. Studies are underway to examine the specificity of the polymerase purified from infected cells at times post infection when the complementary RNA is copied into genomic templates. The present data support a model whereby the viral polymerase which copies vRNA is functionally different from that which synthesizes vRNA from cRNA by virtue of their promoter recognition. It is possible that by regulated modification of the polymerase in infected cells it then becomes capable of recognizing the 3' terminus of plus sense RNA. By analyzing promoter mutants we investigated the fine specificity of the reaction and found that the only single mutation which generated a significantly lower level of synthesis was that of V-$A_3$ RNA. Furthermore, combinations of two or more point changes in positions 3, 5, 8 and 10 greatly lowered synthesis levels.

5.1.4. Insertion of the Heterologous Gene Sequence into the PB2 PB1 PA or NP Gene Segments The gene segments coding for the PB2, PB1, PA and NP proteins contain a single open reading frame with 24–45 untranslated nucleotides at their 5'-end, and 22–57 untranslated nucleotides at their 3'-end. Insertion of a foreign gene sequence into any of these segments could be accomplished by either a complete replacement of the viral coding region with the foreign gene or by a partial replacement. Complete replacement would probably best be accomplished through the use of PCR-directed mutagenesis. The principle of this mutagenesis method is illustrated in FIG. 10. Briefly, PCR-primer A would contain, from 5' to 3', a unique restriction enzyme site, such as a class IIS restriction enzyme site (i.e., a "shifter" enzyme; that recognizes a specific sequence but cleaves the DNA either upstream or downstream of that sequence); the entire 3' untranslated region of the influenza gene segment; and a stretch of nucleotides complementary to the carboxy-terminus coding portion of the foreign gene product. PCR-primer B would contain from the 5' to 3' end: a unique restriction enzyme site; a truncated but active phage polymerase sequence; the complement of the entire 5' untranslated region of the influenza gene segment (with respect to the negative sense vRNA); and a stretch of nucleotides corresponding to the 5' coding portion of the foreign gene. After a PCR reaction using these primers with a cloned copy of the foreign gene, the product may be excised and cloned using the unique restriction sites. Digestion with the class IIS enzyme and transcription with the purified phage polymerase would generate an RNA molecule containing the exact untranslated ends of the influenza viral gene segment with a foreign gene insertion. Such a construction is described for the chloramphenicol acetyltransferase (CAT) gene used in the examples described in Section 7 infra. In an alternate embodiment, PCR-primed reactions could be used to prepare double-stranded DNA containing the bacteriophage promoter sequence, and the hybrid gene sequence so that RNA templates an be transcribed directly without cloning.

Depending on the integrity of the foreign gene product and the purpose of the construction, it may be desirable to construct hybrid sequences that will direct the expression of fusion proteins. For example, the four influenza virus proteins, PB2, PB1, PA or NP are polymerase proteins which are directed to the nucleus of the infected cell through specific sequences present in the protein. For the NP this amino acid sequence has been found to be (single letter code) QLVWMACNSAAFEDLRVLS (Davey et al., 1985, Cell 40: 667–675). Therefore, if it is desired to direct the foreign gene product to the nucleus (if by itself it would not ordinarily do so) the hybrid protein should be engineered to contain a domain which directs it there. This domain could be of influenza viral origin, but not necessarily so. Hybrid proteins can also be made from non-viral sources, as long as they contain the necessary sequences for replication by influenza virus (3' untranslated region, etc.). As another example, certain antigenic regions of the viral gene products may be substituted with foreign sequences. Townsend et al., (1985, Cell 42: 475–482), identified an epitope within the NP molecule which is able to elicit a vigorous CTL (cytotoxic T cell) response. This epitope spans residues 147–161 of the NP protein and consists of the amino acids TYQRTRQLVRLTGMDP. Substituting a short foreign epitope in place of this NP sequence may elicit a strong cellular immune response against the intact foreign antigen. Conversely, expression of a foreign gene product containing this 15 amino acid region may also help induce a strong cellular immune response against the foreign protein.

5.1.5. Insertion of the Heterologous Gene Sequence into the HA or NA Gene Segments The HA and NA proteins, coded for by separate gene segments, are the major surface glycoproteins of the virus. Consequently, these proteins are the major targets for the humoral immune response after infection. They have been the most widely-studied of all the influenza viral proteins as the three-dimensional structures of both these proteins have been solved.

The three-dimensional structure of the H3 hemagglutinin along with sequence information on large numbers of variants has allowed for the elucidation of the antigenic sites on the HA molecule (Webster et al., 1983, In Genetics Of Influenza Virus, P. Palese and D. W. Kingsbury, eds., Springer-Verlag, Vienna, pp. 127–160). These sites fall into four discrete non-overlapping regions on the surface of the HA. These regions are highly variable and have also been shown to be able to accept insertions and deletions. Therefore, substitution of these sites within HA (e.g., site A; amino acids 122–147 of the A/HK/68 HA) with a portion of a foreign protein may provide for a vigorous humoral response against this foreign peptide. In a different approach, the foreign peptide sequence may be inserted within the antigenic site without deleting any viral sequences. Expression products of such constructs may be useful in vaccines against the foreign antigen, and may indeed circumvent a problem discussed earlier, that of propagation of the recombinant virus in the vaccinated host. An intact HA molecule with a substitution only in antigenic sites may allow for HA function and thus allow for the construction of a viable virus. Therefore, this virus can be grown without the need for additional helper functions. Of course, the virus should be attenuated in other ways to avoid any danger of accidental escape.

Other hybrid constructions may be made to express proteins on the cell surface or enable them to be released from the cell. As a surface glycoprotein, the HA has an amino-terminal cleavable signal sequence necessary for transport to the cell surface, and a carboxy-terminal sequence necessary for membrane anchoring. In order to express an intact foreign protein on the cell surface it may be necessary to use these HA signals to create a hybrid protein. Alternatively, if only the transport signals are present and the membrane anchoring domain is absent, the protein may be excreted out of the cell.

In the case of the NA protein, the three-dimensional structure is known but the antigenic sites are spread out over the surface of the molecule and are overlapping. This indicates that if a sequence is inserted within the NA molecule and it is expressed on the outside surface of the NA it will be immunogenic. Additionally, as a surface glycoprotein, the NA exhibits two striking differences from the HA protein. Firstly, the NA does not contain a cleavable signal sequence; in fact, the amino-terminal signal sequence acts as a membrane anchoring domain. The consequence of this, and the second difference between the NA and HA, is that the NA is orientated with the amino-terminus in the membrane while the HA is orientated with the carboxy-terminus in the membrane. Therefore it may be advantageous in some cases to construct a hybrid NA protein, since the fusion protein will be orientated opposite of a HA-fusion hybrid.

5.1.6. Insertion of the Heterologous Gene into the NS and M Gene Segments

The unique property of the NS and M segments as compared to the other six gene segments of influenza virus is that these segments code for at least two protein products. In each case, one protein is coded for by an mRNA which is co-linear with genomic RNA while the other protein is coded for by a spliced message. However, since the splice donor site occurs within the coding region for the co-linear transcript, the NS1 and NS2 proteins have an identical 10 amino acid amino terminus while MI and M2 have an identical 14 amino acid amino terminus.

As a result of this unique structure, recombinant viruses may be constructed so as to replace one gene product within the segment while leaving the second product intact. For instance, replacement of the bulk of the NS2 or M2 coding region with a foreign gene product (keeping the splice acceptor site) could result in the expression of an intact NS1 or M1 protein and a fusion protein instead of NS2 or M2. Alternatively, a foreign gene may be inserted within the NS gene segment without affecting either NS1 or NS2 expression. Although most NS genes contain a substantial overlap of NS1 and NS2 reading frames, certain natural NS genes do not. We have analyzed the NS gene segment from A/Ty/Or/71 virus (Norton et al., 1987, Virology 156: 204–213) and found that in this particular gene, the NS1 protein terminates at nucleotide position 409 of the NS gene segment while the splice acceptor site for the NS2 is at nucleotide position 528. Therefore, a foreign gene could be placed between the termination codon of the NS1 coding region and the splice acceptor site of the NS2 coding region without affecting either protein. It may be necessary to include a splice acceptor site at the 5' end of the foreign gene sequence to ensure protein production (this would encode a hybrid protein containing the amino-terminus of NS1). In this way, the recombinant virus should not be defective and should be able to be propagated without need of helper functions.

Although the influenza virus genome consists of eight functional gene segments it is unknown how many actual segments a virus packages. It has been suggested that influenza can package more than eight segments, and possibly up to 12 (Lamb and Choppin, 1983, Ann. Rev. Biochem. 52: 467–506). This would allow for easier propagation of recombinant virus in that "ninth" gene segment could be designed to express the foreign gene product. Although this "ninth" segment may be incorporated into some viruses, it would soon be lost during virus growth unless some selection is supplied. This can be accomplished by "uncoupling" the NS or M gene segment. The NS2 coding portion could be removed from the NS gene segment and placed on the gene segment coding for the foreign protein (along with appropriate splicing signals). Alternatively, a bicistronic mRNA could be constructed to permit internal initiation to "unsplice" these viral sequences; for example, using the sequences described by Pelletier et al., 1988, Nature 334: 320–325. The resulting recombinant virus with the "uncoupled" NS or M gene would be able to propagate on its own and also would necessarily have to package the "ninth" gene segment, thus ensuring expression of the foreign gene.

5.2. Expression of Heterologous Gene Products Using Recombinant RNA Template The recombinant templates prepared as described above can be used in a variety of ways to express the heterologous gene products in appropriate host cells or to create chimeric viruses that express the heterologous gene products. In one embodiment, the recombinant template can be combined with viral polymerase complex purified as described in Section 6, infra, to produce rRNPs which are infectious. Alternatively, the recombinant template may be mixed with viral polymerase complex prepared using recombinant DNA methods (e.g., see Kingsbury et al., 1987, Virology 156: 396–403). Such rRNPs, when used to transfect appropriate host cells, may direct the expression of the heterologous gene product at high levels. Host cell systems which provide for high levels of expression include continuous cell lines that supply viral functions such as cell lines superinfected with influenza, cell lines engineered to complement influenza viral functions, etc.

In an alternate embodiment of the invention, the recombinant templates or the rRNPs may be used to transfect cell lines that express the viral polymerase proteins in order to achieve expression of the heterologous gene product. To this end, transformed cell lines that express all three polymerase proteins such as 3P-38 and 3P-133 (Krystal et al., 1986, Proc. Natl. Acad. Sci. U.S.A. 83: 2709–2713) may be utilized as appropriate host cells. Host cells may be similarly engineered to provide other viral functions or additional functions such as NP.

5.2.1. Purification of the Viral Polymerase

The viral polymerase proteins used to produce the rRNPs may be purified from dissociated RNP cores isolated from whole virus. In general, RNP cores may be prepared using standard methods (Plotch et al., 1981, Cell 23: 847–858; Rochavansky, 1976, Virology 73: 327–338). The pooled RNP cores may then be centrifuged on a second gradient of CsCl (1.5–3.0M) and glycerol (30%–45%) as described by Honda et al., 1988, J. Biochem. 104: 1021–1026. The active viral polymerase fractions may be isolated from top of the gradient, i.e., in the region of the gradient correlating with 1.5 to 2.0M CsCl and corresponding to the fraction Honda et al. identified as "NP". Surprisingly, this fraction contains all the viral polymerase proteins required for the active complex. Moreover, the P proteins which may be recovered from the bottom of the gradient are not required, and indeed do not provide for the transcription of full length viral RNA. Thus, it appears that the so-called "NP" fraction contains, in addition to NP, the active forms of the PB2, PB1, and PA proteins.

5.2.2. High Concentrations of Polymerase are Required for Cap-Primed RNA Synthesis High concentrations of viral polymerase complex are able to catalyze this virus-specific cap-endonuclease primed transcription. Under the conditions specified in Section 6 infra, about 50 ng NP with 200 pg of the three P proteins were found to react optimally with 5 to 10 ng RNA reaction. The observation has been that although the NP selectively encapsidates influenza vRNA or cRNA in vivo, the NP will bind to RNA nonspecifically in vitro (Kingsbury, et al., 1987, Virology 156: 396–403; Scholtissek and Becht, 1971, J. Gen. Virol. 10: 11–16). Presumably, in order for the viral polymerase to recognize the viral template RNAs in our in vitro reaction, they have to be encapsidated by the NP. Therefore, the addition of a capped mRNA primer would essentially compete with the template RNA for binding of NP. Since the dinucleotide ApG would not be expected to bind NP, the low concentration polymerase was able to use only the short templates with ApG. Supporting this hypothesis is the observation that the higher concentration polymerase preparation is inhibited through the addition of progressively higher amounts of either template RNA or any non-specific RNA. It should also be noted that the unusual specificity for the m7GpppXm cap 1 structure previously shown with viral RNPs was also found with the reconstituted RNPs.

5.2.3. Genomic Length RNA Templates are Efficiently Copied

Plasmid-derived RNA identical to segment 8 of the A/WSN/33 virus was specifically copied by the polymerase (using the PCR method described in FIG. 10). In reactions using RNA extracted from virus, all eight segments were copied, although the HA gene was copied at a lower level. The background in these reactions was decreased in comparison to the 30 to 53 nt templates, probably since the contaminating RNAs in the polymerase preparation were predominantly defective RNAs of small size. Recombinant templates encoding foreign genes transcribed in this system may be used to rescue the engineered gene in a virus particle.

5.3. Preparation of Chimeric Negative Strand RNA Virus

In order to prepare chimeric virus, reconstituted RNPs containing modified influenza virus RNAs or RNA coding for foreign proteins may be used to transfect cells which are also infected with a "parent" influenza virus. Alternatively, the reconstituted RNP preparations may be mixed with the RNPs of wild type parent virus and used for transfection directly. Following reassortment, the novel viruses may be isolated and their genomes be identified through hybridization analysis. In additional approaches described herein for the production of infectious chimeric virus, rRNPs may be replicated in host cell systems that express the influenza viral polymerase proteins (e.g., in virus/host cell expression systems; transformed cell lines engineered to express the polymerase proteins, etc.), so that infectious chimeric virus are rescued; in this instance, helper virus need not be utilized since this function is provided by the viral polymerase proteins expressed. In a particularly desirable approach, cells infected with rRNPs engineered for all eight influenza virus segments may result in the production of infectious chimeric virus which contain the desired genotype; thus eliminating the need for a selection system.

Theoretically, one can replace any one of the eight gene segments, or part of any one of the eight segments with the foreign sequence. However, a necessary part of this equation is the ability to propagate the defective virus (defective because a normal viral gene product is missing or altered). A number of possible approaches exist to circumvent this problem. We have shown that mutants of influenza virus defective in the PB2 and NP proteins can be grown to substantially higher titers in cell lines which were constructed to constitutively express the polymerase and NP proteins (Krystal et al., 1986 Proc. Natl. Acad. Sci. U.S.A. 83: 2709–2813). Similar techniques may be used to construct transformed cell lines that constitutively express any of the influenza genes. These cell lines which are made to express the viral protein may be used to complement the defect in the recombinant virus and thereby propagate it. Alternatively, certain natural host range systems may be available to propagate recombinant virus. An example of this approach concerns the natural influenza isolate CR43-3. This virus will grow normally when passaged in primary chick kidney cells (PCK) but will not grow in Madin-Darby canine kidney cells (MDCK), a natural host for influenza (Maassab & DeBorde, 1983, Virology 130: 342–350). When we analyzed this virus we found that it codes for a defective NS1 protein caused by a deletion of 12 amino acids. The PCK cells contain some activity which either complements the defective NS1 protein or can completely substitute for the defective protein.

A third approach to propagating the recombinant virus may involve co-cultivation with wild-type virus. This could be done by simply taking recombinant virus and co-infecting cells with this and another wild-type virus (preferably a vaccine strain). The wild-type virus should complement for the defective virus gene product and allow growth of both the wild-type and recombinant virus. This would be an analogous situation to the propagation of defective-interfering particles of influenza virus (Nayak et al., 1983, In: Genetics of Influenza Viruses, P. Palese and D. W. Kingsbury, eds., Springer-Verlag, Vienna, pp. 255–279). In the case of defective-interfering viruses, conditions can be modified such that the majority of the propagated virus is the defective particle rather than the wild-type virus. Therefore this approach may be useful in generating high titer stocks of recombinant virus. However, these stocks would necessarily contain some wild-type virus.

Alternatively, synthetic RNPs may be replicated in cells co-infected with recombinant viruses that express the influenza virus polymerase proteins. In fact, this method may be used to rescue recombinant infectious virus in accordance with the invention. To this end, the influenza virus polymerase proteins may be expressed in any expression vector/ host cell system, including but not limited to viral expression vectors (e.g., vaccinia virus, adenovirus, baculovirus, etc.) or cell lines that express the polymerase proteins (e.g., see Krystal et al., 1986, Proc. Natl. Acad. Sci. USA 83: 2709–2713). Moreover, infection of host cells with rRNPs encoding all eight influenza virus proteins may result in the production of infectious chimeric virus particles. This system would eliminate the need for a selection system, as all recombinant virus produced would be of the desired genotype. In the examples herein, we describe a completely synthetic replication system where, rather than infecting cells with influenza virus, synthetic RNP's are replicated in cells through the action of influenza virus proteins expressed by recombinant vaccinia vectors. In this way we show that the only influenza virus proteins essential for transcription and replication of RNP are the three polymerase proteins and the nucleoprotein.

It should be noted that it may be possible to construct a recombinant virus without altering virus viability. These altered viruses would then be growth competent and would not need helper functions to replicate. For example, alterations in the hemagglutinin gene segment and the NS gene segment discussed, supra, may be used to construct such viable chimeric viruses.

In the examples infra, the construction of a recombinant plasmid is described that, following transcription by T7 polymerase, yielded an RNA template which was recognized and transcribed by the influenza virus polymerase in vitro. This RNA template corresponds to the NS RNA of an influenza virus except that the viral coding sequences are replaced by those of a CAT gene. This recombinant negative strand viral RNA template was then mixed with purified influenza virus polymerase to reconstitute an RNP complex. The recombinant RNP complex was transfected into cells which were then infected with influenza virus, leading to expression of CAT activity.

A number of factors indicate that this system represents a biologically active recombinant RNP complex which is under tight control of the signals for transcription, replication and packaging of influenza virus RNAs. First, the CAT gene is of negative polarity in the recombinant viral RNA used for RNP transfection. Thus, the incoming RNA cannot be translated directly in the cell and must first be transcribed by the influenza virus polymerase to permit translation and expression of the CAT gene. Secondly, neither transfected naked recombinant RNA alone in the presence of infecting helper virus, nor recombinant RNP complex in the absence of infecting helper virus is successful in inducing CAT activity. This suggests that influenza viral proteins provided by the incoming RNP, as well as by the infecting helper virus, are necessary for the amplification of the recombinant RNA template. Finally, after RNP-transfection and infection by helper virus, virus particles emerge which apparently contain the recombinant RNA, since these particles again induce CAT activity in freshly infected cells. These results suggest that the 26 3' terminal and the 22 5' terminal nucleotides corresponding to the terminal nucleotides in the influenza A virus NS RNA are sufficient to provide the signals for polymerase transcription and replication, as well as for packaging of the RNA into particles.

The foregoing results, which defined the cis acting sequences required for transcription, replication and packaging of influenza virus RNAs, were extended by additional working examples, described infra, which demonstrate that recombinant DNA techniques can be used to introduce site-specific mutations into the genomes of infectious influenza viruses.

Synthetic RNAs, derived by transcription of plasmid RNA in vitro were used in RNP-transfection experiments to rescue infectious influenza virus. To enable selection of this virus, we chose a system that required the presence of a WSN-like neuraminidase gene in the rescued virus. Viruses containing this gene can grow in MDBK cells in the absence of protease in the medium (Schulman et al., 1977, J. Virol. 24: 170–176). The helper virus WSN-HK does not grow under these circumstances. Clearly, alternative selection systems exist. For example, antibody screens or conditionally lethal mutants could be used to isolate rescued viruses containing RNAs derived from plasmid DNAs. In the experiments viruses described infra, viruses which were WSN virus-like were recovered. The WSN NA gene was derived from plasmid DNAs or from purified WSN virion RNA (FIG. 17, lanes 2 and 5). In the latter case, using whole virion RNA for the RNP-transfection, we do not know whether other genes were also transferred to the rescued virus, since the helper virus shares the remaining seven genes with WSN virus. The rescued viruses had the expected RNA patterns (FIG. 17) and grew to titers in MDBK or MDCK cells which were indistinguishable from those of the wild type WSN virus. It should be noted that rescue of an NA RNA containing a single nucleotide deletion in the 5' nontranslated region was not possible. This again illustrates the importance of regulatory sequences present in the nontranslated regions of influenza virus RNAs. We also rescued virus using RNA that was engineered to contain 5 nucleotide changes in a 39 nucleotide long region (FIG. 16). We verified the presence of these mutations in the rescued mutant virus by direct sequencing of the RNA (FIG. 18). These mutations did not result in any amino acid change in the neuraminidase protein and thus were not expected to change the biological property of the virus. Although this virus was not extensively studied, its plaquing behavior and its growth characteristics were indistinguishable from that of wild type WSN virus. Using such technology, mutations may be introduced that will change the biological characteristics of influenza viruses. These studies will help in distinguishing the precise functions of all the viral proteins, including those of the nonstructural proteins. In addition, the nontranslated regions of the genome can be studied by mutagenesis, which should lead to a better understanding of the regulatory signals present in viral RNAs. An additional area of great interest concerns the development of the influenza virus system as a vaccine vector.

5.4. Vaccine Formulations Using the Chimeric Viruses

Virtually any heterologous gene sequence may be constructed into the chimeric viruses of the invention for use in vaccines. Preferably, epitopes that induce a protective immune response to any of a variety of pathogens, or antigens that bind neutralizing antibodies may be expressed by or as part of the chimeric viruses. For example, heterologous gene sequences that can be constructed into the chimeric viruses of the invention for use in vaccines include but are not limited to epitopes of human immunodeficiency virus (HIV) such as gp120; hepatitis B virus surface antigen (HBsAg); the glycoproteins of herpes virus (e.g., gD, gE); VP1 of poliovirus; antigenic determinants of non-viral pathogens such as bacteria and parasites, to name but a few. In another embodiment, all or portions of immunoglobulin genes may be expressed. For example, variable regions of anti-idiotypic immunoglobulins that mimic such epitopes may be constructed into the chimeric viruses of the invention.

Either a live recombinant viral vaccine or an inactivated recombinant viral vaccine can be formulated. A live vaccine may be preferred because multiplication in the host leads to a prolonged stimulus of similar kind and magnitude to that occurring in natural infections, and therefore, confers substantial, long-lasting immunity. Production of such live recombinant virus vaccine formulations may be accomplished using conventional methods involving propagation of the virus in cell culture or in the allantois of the chick embryo followed by purification.

In this regard, the use of genetically engineered influenza virus (vectors) for vaccine purposes may require the presence of attenuation characteristics in these strains. Current live virus vaccine candidates for use in humans are either cold adapted, temperature sensitive, or passaged so that they derive several (six) genes from avian viruses, which results in attenuation. The introduction of appropriate mutations (e.g., deletions) into the templates used for transfection may produce the novel viruses with attenuation characteristics. For example, specific missense mutations which are associated with temperature sensitivity or cold adaptation can be made into deletion mutations. These mutations should be more stable than the point mutations associated with cold or temperature sensitive mutants and reversion frequencies should be extremely low.

Alternatively, chimeric viruses with "suicide" characteristics may be constructed. Such viruses would go through only one or a few rounds of replication in the host. For example, cleavage of the HA is necessary to allow for reinitiation of replication. Therefore, changes in the HA cleavage site may provide a virus that replicates in an appropriate cell system but not in the human host. When used as a vaccine, the recombinant virus would go through a single replication cycle and induce a sufficient level of immune response but it would not go further in the human host and cause disease. Recombinant viruses lacking one or more of the essential influenza virus genes would not be able to undergo successive rounds of replication. Such defective viruses can be produced by co-transfecting reconstituted RNPs lacking a specific gene(s) into cell lines which permanently express this gene(s). Viruses lacking an essential gene(s) will be replicated in these cell lines but when administered to the human host will not be able to complete a round of replication. Such preparations may transcribe and translate—in this abortive cycle—a sufficient number of genes to induce an immune response. Alternatively, larger quantities of the strains could be administered, so that these preparations serve as inactivated (killed) virus vaccines. For inactivated vaccines, it is preferred that the heterologous gene product be expressed as a viral component, so that the gene product is associated with the virion. The advantage of such preparations is that they contain native proteins and do not undergo inactivation by treatment with formalin or other agents used in the manufacturing of killed virus vaccines.

In another embodiment of this aspect of the invention, inactivated vaccine formulations may be prepared using conventional techniques to "kill" the chimeric viruses. Inactivated vaccines are "dead" in the sense that their infectivity has been destroyed. Ideally, the infectivity of the virus is destroyed without affecting its immunogenicity. In order to prepare inactivated vaccines, the chimeric virus may be grown in cell culture or in the allantois of the chick embryo, purified by zonal ultracentrifugation, inactivated by formaldehyde or β-propiolactone, and pooled. The resulting vaccine is usually inoculated intramuscularly.

Inactivated viruses may be formulated with a suitable adjuvant in order to enhance the immunological response. Such adjuvants may include but are not limited to mineral gels, e.g., aluminum hydroxide; surface active substances such as lysolecithin, pluronic polyols, polyanions; peptides; oil emulsions; and potentially useful human adjuvants such as BCG and Corynebacterium parvum.

Many methods may be used to introduce the vaccine formulations described above. These include but are not limited to oral, intradermal, intramuscular, intraperitoneal, intravenous, subcutaneous, and intranasal routes. It may be preferable to introduce the chimeric virus vaccine formulation via the natural route of infection of the pathogen for which the vaccine is designed. Where a live chimeric virus vaccine preparation is used, it may be preferable to introduce the formulation via the natural route of infection for influenza virus. The ability of influenza virus to induce a vigorous secretory and cellular immune response can be used advantageously. For example, infection of the respiratory tract by chimeric influenza viruses may induce a strong secretory immune response, for example in the urogenital system, with concomitant protection against a particular disease causing agent.

6. EXAMPLE: PROMOTER ANALYSIS OF THE INFLUENZA VIRAL RNA POLYMERASE

In the examples described below, polymerase which is depleted of genomic RNA was prepared from the upper fractions of the CsCl-glycerol gradient centrifugation. This polymerase is able to copy short model templates which are derived from transcription of appropriate plasmic DNA with bacteriophage T7 RNA polymerase in a sequence-specific manner. The termini of this model RNA are identical to the 3' 15 and 5' 22 nucleotides conserved in segment 8 from all influenza A viral RNAs. By manipulating the plasmid in order to prepare different RNAs to serve as template, we demonstrated that recognition of and synthesis from this model RNA was specific for the promoter at the 3' terminal sequence and did not require the panhandle. In addition, site specific mutagenesis identified nucleotide positions responsible for the viral polymerase favoring synthesis from genomic sense templates over complementary sense RNA. Conditions were also found in which cap-endonuclease primed RNA synthesis could be observed using model RNAs. In addition, the reconstituted system permitted virus-specific synthesis from genomic length RNAs, derived either from plasmids or from RNA purified from virus through phenol extraction.

6.1. Materials and Methods

6.1.1. Purification of the Viral RNA Polymerase

RNP cores were prepared from whole virus using standard methods (Plotch, et al., 1981, Cell 23: 847–858; Rochavansky, 1976, Virology 73: 327–338). Two to three milligrams of virus were disrupted by incubating in 1.5% Triton N-101, 10 mg/ml lysolecithin, 100 mM tris-HCl, pH 8.0, 100 mM KCl, 5 mM $MgCl_2$, 5% glycerol and 1.5 mM dithiothreitol. The sample was fractionated by centrifugation on a 30–70% glycerol (w/v) step gradient in the presence of 50 mM tris-HCl, pH 7.8 and 150 mM NaCl. The core preparation was centrifuged at 45,000 rpm in an SW50.1 rotor for 4 hours at 4° C. Fractions enriched in RNP were identified by SDS-polyacrylamide gel electrophoresis of protein samples from each fraction and staining with silver. The core fractions were then subjected to a second gradient centrifugation as was described in Honda et al. 1988, J. Biochem. 104: 1021–1026. This second gradient had steps of 0.5 ml 3.0M CsCl and 45% (w/v) glycerol, 1.75 ml 2.5 M CsCl and 40% glycerol, 1.25 ml 2.0M CsCl and 35% glycerol, and 1.0 ml of 1.5 M CsCl and 30% glycerol. All steps were buffered with 50 mM tris-HCl, pH 7.6 and 100 mM NaCl. 0.5 ml of RNP cores were layered on top and the sample was centrifuged at 45,000 rpm in an SW50.1 rotor for 25 hours at 4° C. Polymerase fractions were again identified by SDS-polyacrylamide electrophoresis of the protein samples and silver staining. Active polymerase fractions were generally found in the region of the gradient correlating with 1.5 to 2.0 M CsCl. These fractions were pooled and then dialyzed against 50 mM tri-HCl, pH 7.6, 100 mM NaCl and 10 mM $MgCl_2$, and concentrated in centricon-10 tubes (Amicon) or fractions were dialyzed in bags against 50 mM tris-HCl, pH 7.6, 100 mM NaCl, 10 mM $MgCl_2$, 2 mM dithiothreitol, and 50% glycerol.

6.1.2. Preparation of Plasmid

The plasmid design is indicated in FIG. 2. Insert DNA for the pV-wt plasmid was prepared using an Applied Biosystems DNA synthesizer. The "top" strand was 5'- GAAGCTTAATACGACTCACTATAAGTAGAAACAAGGGTG
TTTTTTCATATCATTTAAACTTCACCCTGCTTTTGCTGAA
TTCATTCTTCTGCAGG-3'.

The "bottom" strand was synthesized by primer-extension with

5'- CCTGCAGAAGAATGA-3' as primer. The 95 bp DNA was digested with HindIII and PstI and purified by extraction with phenol/chloroform, ethanol precipitation, and passage over a NACS-prepack ion Exchange column (Bethesda Research Laboratories). This DNA was ligated into pUC-19 which had been digested with HindIII and PstI and then used to transform E. coli strain DH5-α which had been made competent using standard protocols. Bacteria were spread on agar plates containing X-gal and IPTG, and blue colonies were found to have the plasmid containing the predicted insert since the small insert conserved the lacZ reading frame and did not contain a termination codon. The pM-wt plasmid was prepared by a similar strategy except that both strands were chemically synthesized with the upper strand having the sequence 5'- GAAGCTTAATACGACTCACTATAAGCAAAAGCAGGGTGA
AGTTTAAATGATAT — GAAAAAACACCCTTGTTTCTACTG
AATTCATTCTTCTGCAGG-3'.

The pV-d5' plasmid (FIG. 2) was prepared using the oligonucleotides

5'- AGCTTAATACGACTCACTATAAGATCTATTAAACT — T
CACCCTGCTTTTGCTGAATTCATTCTTCTGA-3'  and

5'- GAAGAATGAAT — TCAGCAAAAGCAGGGTGAAGTTTAA
TAGATCTTATAGTGAGTCGTATTA-3'.

The DNAs were annealed and ligated into the HindIII/PstI digested pUC-19 and white colonies were found to contain the correct plasmid because this insert resulted in a frame-shift in the lacZ gene. The point mutants were isolated following digestion of pV-d5' with BglII and PstI and ligation of the linearized plasmid with a single stranded oligonucleotide of mixed composition. Since BglII laves a 5' extension and PstI a 3' extension, a single oligonucleotide was all that was necessary for ligation of insert. The host cell was then able to repair gaps caused by the lack of a complementary oligonucleotide. Oligonucleotides were designed to repair the frameshift in the lacZ gene so that bacteria which contained mutant plasmids were selected by their blue color.

Plasmid pHgaNS, which was used to prepare an RNA identical to segment 8 of A/WSN/33, was prepared using the primers 5'- CCGAATTCTTAATACGACTCACTATAAGTAGAAACAAGG GTG-3' and

5'- CCTCTAGACGCTCGAGAGCAAAAGCAGGTG-3' in a polymerase chain reaction off of a cDNA clone. The product was then cloned into the XbaI/EcoRI window of pUC19.

6.1.3. Preparation of RNA Templates

Plasmid DNAs were digested with MboII or other appropriate endonucleases (see FIG. 2), and the linearized DNA was transcribed using the bacteriophage T7 RNA polymerase. Run-off RNA transcripts were treated with RNAse-free DNAse 1 and then the RNA was purified from the proteins and free nucleotides using Qiagen tip-5 ion exchange columns (Qiagen, Inc.). Following precipitation in ethanol, purified RNAs were resuspended in water and a sample was analyzed by electrophoresis and followed by silver staining of the polyacrylamide gel in order to quantify the yield of RNA.

6.1.4. Influenza Viral Polymerase Reactions

In a 25 $\mu$l total volume, about 30 $\mu$g of nucleoprotein and 200 pg total of the three polymerase proteins were mixed with 10 ng of template RNA and the solution was made up to a final concentration of: 50 mM Hepes pH 7.9, 50 mM NaCl, 5 mM $MgCl_2$, 1 mM dithiothreitol, 0.05% NP-40, 0.4 mM adenylyl-(3'–5')-guanosyl (ApG) dinucleotide (Pharmacia), 0.5 mM ATP, 0.5 mM GTP, 0.5 mM CTP and approximately 0.6 $\mu$M $\alpha$-$^{32}$P-UTP (40 $\mu$Ci at 3000 Ci/mmole, New England Nuclear). Reactions were assembled on ice and then transferred to a 30° C. water bath for 90 minutes. Reactions were terminated by the addition of 0.18 ml ice-cold 0.3M sodium acetate/10 mM EDTA and were then extracted with phenol/chloroform (1:1 volume ratio). Following the first extraction, 15 $\mu$g polyI-polyC RNA was added as carrier, and the sample was extracted again with phenol/ chloroform. The samples were then extracted with ether and precipitated in ethanol. Following centrifugation, the RNA pellet was washed twice with 70% ethanol and then dried under vacuum.

In reactions using the high concentration polymerase, conditions were identical as above except that 20 ng of template RNA were added. In reactions using genomic length RNAs, the amount of polymerase used was doubled, 50 ng of template RNA was used, and the UTP concentration was raised to 2.6 $\mu$M.

The RNA was resuspended in a dye mix containing 78% formamide, 10 mM EDTA, 0.1% xylene cyanol and 0.05% bromophenol blue. Typically, a sample from this RNA was electrophoresed on an 8% polyacrylamide gel in the absence of urea, and the remainder was denatured by heating to 100° C. for 1.5 minutes and an aliquot was loaded on an 8% polyacrylamide gel containing 7.7M urea. Gels were fixed by a two step procedure, first in 10% acetic acid, and then in 25% methanol/8% acetic acid. Gels were dried onto filter paper and then exposed to x-ray film.

When different RNAs were being tested for use as template, the different RNA preparations were always analyzed on polyacrylamide gels and stained with silver in order that equal amounts of each template were used. To quantitate the amount of product, gels were exposed to x-ray film in the absence of an intensifying screen in order to improve the linearity of the densitometer readings. Autoradiographs were analyzed using a FB910 scanning densitometer (Fisher Biotech) and peaks were evaluated using computer software from Fisher Biotech.

6.1.5. Nuclease Analysis of Reaction Products

For ribonuclease T1 analysis of the two principle RNA products, reaction products were analyzed by 8% polyacrylamide gel electrophoresis (without urea) and the gel was not treated with fixative. The wet gel was exposed to an x-ray film and the appropriate gel pieces were located and excised. The gel piece was crushed in 0.3 ml containing 10 mM tris pH 7.5, 1 mM EDTA, 0.1% sodium dodecyl sulfate, and 1 $\mu$g tRNA as carrier. The RNA diffused into this solution for 3 hours and then the gel was pelleted and the supernatant was made 0.3M in sodium acetate. The supernatant was then extracted twice in phenol/chloroform and once in ether and then precipitated in ethanol. The RNA pellet was resuspended in 5 $\mu$l formamide, denatured in boiling water for 1.5 minutes and then diluted by the addition of 0.1 ml 10 mM tris-HCl, pH 7.5, and 1 mM EDTA. Ribonuclease T1 (50 units, Boehringer Mannheim Biochemicals) was added and the samples were incubated for 60 minutes at 37° C. V-wt and M-wt RNAs synthesized with T7 RNA polymerase in the presence of $\alpha$-$^{32}$P- UTP were similarly digested with RNAse T1. Reaction products were extracted in phenol/chloroform and precipitated in ethanol and then were analyzed on 20% polyacrylamide gels containing 7.7M urea.

Nuclease S1 analysis of reaction products was done on transcribed RNA by first terminating the standard polymerase reaction through the addition of SI buffer to a volume of 0.2 ml with 0.26M NaCl, 0.05M sodium acetate, pH 4.6, and 4.5 mM zinc sulfate. The sample was divided into two 0.1 ml volumes and 100 units of S1 nuclease (Sigma Chemical Company) were added to one tube. The samples were incubated for 60 minutes at 37° C. Following the incubation, EDTA (10 mM final concentration) and 15 $\mu$g polyI-polyC RNA was added and the sample was extracted with phenol/chloroform and precipitated in ethanol. The samples were then subjected to polyacrylamide gel electrophoresis.

6.2. Results

6.2. 1. Preparation of Influenza Viral RNA Polymerase and of Template RNA

RNP cores of influenza virus A/Puerto Rico/8/34 were prepared by disruption of virus in lysolecithin and Triton N-101 followed by glycerol gradient centrifugation (Rochavansky, 1976, Virology 73: 327–338). Fractions containing cores were then subjected to a second centrifugation in a CsCl-glycerol step gradient (Honda, et al., 1988, J. Biochem. 104: 1021–1026). Fractions containing the polymerase were identified by gel electrophoresis of samples followed by silver-staining. FIG. 1 shows the polymerase preparation after CsCl centrifugation. Bovine serum albumin (BSA) was added during dialysis to protect against protein loss. Densitometric scanning of lane 4 compared to known quantities of whole virus in lanes 1 and 2 allowed us to estimate that the proteins in lane 4 consist of 150 ng of NP and about 1 ng total of the three polymerase proteins. One fifth of the preparation used for this gel was used per reaction.

The overall design of the plasmids used to prepare template RNAs in this study is depicted in FIG. 2. The entire insert was prepared using oligonucleotides from a DNA synthesizer which were then cloned into the polylinker of pUC19. The insert contained a truncated promoter sequence recognized by the bacteriophage T7 RNA polymerase (Studier and Dunn, 1983, Cold Spring Harbor Symposia on Quantitative Biology, XLVII, 999–1007) so that the first nucleotides synthesized were the terminal 22 nucleotides (nt) of the conserved sequence from the 5' end of the genome RNA. When the plasmid was cut with restriction endonuclease MboII (which cuts 7 bases upstream of its recognition site), the RNA which resulted from T7 RNA polymerase transcription ended with the terminal 3' nucleotides of the influenza viral sequence. Included in the sequence was the poly-U stretch adjacent to the 5'end of the conserved terminus which is thought to comprise at least part of the termination-polyadenylation signal (Robertson, et al., 1981, J. Virol. 38, 157–163). The total length of this model genomic RNA was 53 nt since a 16 nt spacer separated the terminal conserved sequences. The model RNA which contained both termini identical to those of vRNA was named V-wt. The RNA M-wt encoded the exact complementary strand of V-wt so that the termini match those of complementary RNA (cRNA). V-wt and M-wt were constructed to serve as models for influenza virus-specific vRNA and cRNA, respectively.

6.2.2. Viral Polymerase Catalyzes Synthesis of a Full Length Copy of the Template In the reaction using the influenza viral polymerase, V-wt template and ApG primer, a product was obtained which comigrated with a 53 nt RNA on denaturing gels. RNA migrating as a doublet at a position of about 40 to 45 nucleotides (FIG. 3A, lane 2) was also seen. This shorter product is shown below to be RNA which had terminated at a stretch of adenosines present between nucleotides 43–48 in the virion sense template. In addition to the template specific transcripts, a general background of light bands could be seen which correspond to truncated RNA products transcribed from viral genomic RNA not removed during the CsCl-glycerol centrifugation step. When no primer is used, there was no specific transcription product seen (FIG. 3A, lane 3). Additional experiments showed globin mRNA, containing a terminal cap 1 structure, was inactive as primer using initial preparations of polymerase.

When the polymerase reaction was terminated by the addition of excess buffer favorable for nuclease S1 digestion and nuclease was added, the radioactively-labeled product was resistent to digestion (FIG. 3B, lane 2). By contrast these conditions very efficiently digested the V-wt single-stranded RNA radioactively synthesized with T7 RNA polymerase (FIG. 3B, lanes 3 and 4). These nuclease S1 data confirmed that the opposite strand was indeed being synthesized in these reactions. The product of the reaction might be a double stranded RNA, but it could not be ruled out that the product was in fact single stranded and later annealed to the template RNA in the presence of high salt used in the nuclease reaction.

The RNA products were purified by electrophoresis on an 8% gel, excised, eluted from the gel, and then digested by ribonuclease T1. Products were analyzed by electrophoresis and compared to the patterns generated by RNase T1 digestion of internally labeled M-wt and V-wt control probes. As can be seen in FIG. 3C, the full length RNA (lane 1) has the identical pattern as does the plus sense RNA, M-wt (lane 3), and it does not have the pattern of the V-wt RNA (lane 4). The observed patterns were essentially identical to that which is predicted from the sequence of the RNA and thus showed that the polymerase faithfully copied the V-wt template. The smaller RNA product, a doublet with most templates, was also digested with RNase T1. Its pattern was similar to that of the full length RNA product (FIG. 3C, lane 2) except the 14 base oligonucleotide was not present. Instead, a faint 13 base oligonucleotide was seen, thus mapping the termination of the short RNA to position 44, a site where two uridines would be incorporated. Since the amount of smaller RNA product decreased at higher UTP concentrations and disappeared when CTP was used as label, these bands appeared to be an artifact of low UTP concentrations in the polymerase reaction.

6.2.3. Conditions for the Polymerase Reactions Using Model RNA Templates

It was found that protein samples containing about 30 ng of NP protein and about 200 pg total of the three P proteins would react optimally with 5 to 10 ng of RNA. By using cold competitor RNA, polyI-polyC, it was found that excess RNA nonspecifically inhibited transcription, possibly via non-specific binding of the NP protein (Kingsbury, et al., 1987, Virology 156: 396–403; Scholtissek and Becht, 1971, J. Gen. Virol. 10: 11–16). In the absence of nonspecific competitor, variations in the amount of template between 1 and 10 ng produced little change in the efficiency of RNA synthesis. The NP protein and RNA were present at about equal molar concentrations and these were each about a thousand-fold in excess of the moles of the complex (assuming it to be 1:1:1) formed by the three P proteins in the typical reaction.

Since these reconstituted RNPs were able to use ApG but not globin mRNA as primer, we tested these model RNPs for other variables of the transcription reaction. In all other ways tested, the reconstituted RNPs behaved in solution similarly to those RNPs purified from detergent disrupted virus. The optimum temperature for RNA synthesis was 30° C. (FIG. 4A, lane 2) as has been repeatedly found for the viral polymerase (Bishop, et al., 1971, J. Virol. 8: 66–73; Takeuchi, et al., 1987, J. Biochem 101: 837–845; Ulmanen, et al., 1983, J. Virol. 45: 27–35). Also, the most active salt conditions were 60 mM NaCl (FIG. 4B, lane 2), again consistent with conditions used by several groups (Bishop, et al., 1971, J. Virol. 8: 66–73; Honda, et al., 1988, J. Biochem. 104: 1021–1026; Shapiro, and Krug, 1988, J. Virol. 62: 2285–2290). FIG. 4C shows a time-course experiment. The amount of RNA synthesis appeared to increase roughly linearly for the first 90 minutes, as was found for viral RNPs (Takeguchi, et al., 1987, J. Biochem. 101: 837–845).

6.2.4. Specificity of the Elongation Reaction

Various RNAs were tested for suitability as templates for the RNA polymerase of influenza virus. The pV-wt plasmid clone was digested with either EcoRI, PstI or SmaI, and T7 polymerase was used to transcribe RNA. This resulted in RNAs identical to V-wt except for the addition of 5, 13 and 38 nt at the 3' end. In FIG. 5A an overexposure of an autoradiograph is shown in order to demonstrate that no transcripts over background were observed in reactions which contained as template: two of the RNAs identical to V-wt except they contained 13 and 38 nt of extra sequence on the 3' terminus (lanes 1 and 2); a single stranded DNA of identical sequence to that of V-wt (lane 4); and an unrelated 80 nt RNA generated by transcribing the polylinker of pIBI-31 with T3 RNA polymerase (lane 5). However, the V-Eco template, containing five extra nucleotides on the 3' end, could be recognized and faithfully transcribed, although at approximately one-third the efficiency of the wild type V-wt RNA (FIG. 5B, lane 3). It is interesting to note that initiation on the V-Eco RNA by the influenza viral polymerase appeared to occur at the correct base since the transcribed RNA was the same size as the product from the V-wt template.

6.2.5. Analysis of the Promoter Region for the Viral RNA Polymerase

The original construct used for these studies contained the sequences of both RNA termini of genomic RNAs which could base pair and thus form a panhandle. This was done since it was shown that the vRNA in virions and in RNPs in infected cells was in circular conformation via the 15 to 16 nt long panhandle (Honda, et al., 1988, J. Biochem. 104: 1021–1026; Hsu, et al., 1987, Proc. Natl. Acad. Sci. USA 84: 8140–8144). It was further shown that the viral polymerase was bound to the double stranded structure (Honda, et al., 1988, J. Biochem. 104: 1021–1026), thus leading to the suggestion that the promoter for RNA synthesis was the panhandle. In order to test whether the panhandle was an absolute requirement for recognition, the following templates were used: the plasmid pV-wt was digested with DraI prior to transcription by the T7 polymerase (FIG. 2). This should result in an RNA molecule of 32 nt containing only virus-specific sequences from the 5' end of the RNA. When this RNA was used as template, no apparent product was produced (FIG. 5B, lane 2). Therefore the 3' terminus of virion RNA was required for this reaction. This finding was consistent with the fact that the initiation site at the 3' end of V-wt was not present in V-Dra. A second plasmid clone was produced which deleted the 5' terminal sequences but kept intact the 3' terminus. This clone, pV-d5', when digested with MboII and used for transcription by T7 polymerase produced a major transcript of 30 nt and minor species of 29 and 31 nt. Surprisingly, this template was recognized and copied by the influenza viral polymerase. FIG. 7, lane 1, shows that the product of the viral RNA polymerase reaction with V-d5' contains multiple bands reflecting the input RNA. When the products shown in FIG. 7, lane 1, were eluted from gels and subjected to RNase T1 analysis, the pattern expected of the transcription product of V-d5' was observed. Since the V-d5' RNA template was copied, the panhandle was not required for viral polymerase binding and synthesis.

Although the 5' terminus was not required for synthesis by the polymerase, a distinct possibility was that V-wt RNA might be a preferred template as compared to V-d5'. In order to examine this, reactions were done in which the templates were mixed. The V-wt RNA was present at 5 ng in each reaction. The V-d5' was absent (FIG. 6, lane 1) or was present at a 1/5 molar ratio (FIG. 6, lane 2) or a 1/1 molar ratio (FIG. 6, lane 3). The relative intensities of the bands from each RNA were determined by densitometry of the autoradiograph. The values were corrected for the amount of the radioactive nucleotide, UTP, which could be incorporated into each product, and the value was normalized so that the level of synthesis in each lane was set equal to one. The level of copying of V-wt decreased as V-d5' was increased. When V-d5' was present in one fifth molar ratio, its corrected level of synthesis was about one fourth of that from V-wt (FIG. 6, lane 2). When the two templates were present in equimolar amounts, the level of synthesis from V-wt was about 60% of the total (FIG. 6, lane 3) which might be within the expected range of experimental error for equivalent levels of synthesis. Similar results were obtained when V-d5' RNA was kept constant and the V-wt RNA was varied. It was thus concluded that the panhandle-containing V-wt RNA was not greatly favored over the template RNA which only contained the proper 3' terminus.

6.2.6. The Viral Polymerase Does Not Copy RNA Templates Containing Plus-Sense Termini As described earlier, the influenza RNA polymerase performs three distinct activities during the course of an infection. Two activities involve the transcription of genome sense RNA and the third involves copying of the complementary sense RNA into vRNA. We therefore constructed an RNA template which contained the 5' and 3' termini of the complementary sense RNA of segment 8 (M-wt; FIG. 2).

When the M-wt RNA was used as template, little synthesis was observed (FIG. 5B, lane 4). In two experiments used for quantitation, the average level of synthesis from M-wt RNA was 4% that of V-wt. In comparing the V-wt and M-wt RNA promoters, the M-wt has only three transition changes and one point insertion within the 3' 15 nucleotides. These include a G to A change at position 3, a U to C change at position 5, a C to U change at position 8 and an inserted U between the ninth and tenth nucleotides (see Table II, below). In order to determine which of the four point differences in the 3' termini were responsible for the specificity, many combinations of these were prepared and assayed for efficiency as a template (FIG. 7). These templates were derivatives of V-d5' since they did not contain the 5' terminus. The results of densitometry scans of several experiments are outlined in Table II.

TABLE II

QUANTITATIVE COMPARISON OF THE EFFECT OF POINT MUTATIONS IN THE PROMOTER SEQUENCE*

| Template | 3' sequence | Level of RNA Synthesis |
|---|---|---|
| V-d5' | CACCCUGCUUUUGCU-OH | 1 |
| V-A3 | CACCCUGCUUUUACU-OH | 0.4 |
| V-C5 | CACCCUGCUUCUGCU-OH | 1.0 |
| V-dU$_{25}$U$_8$ | CACCCUGUUUUUGCU-OH | 1.0 |
| V-U$_8$A$_3$ | CACCCUGUUUUUACU-OH | 0.08 |
| V-U$_8$C$_5$ | CACCCUGUUUCUGCU-OH | 0.3 |
| V-iU$_{10}$ | CACCCUUGCUUUUGCU-OH | 0.7 |
| V-iU$_{10}$A$_3$ | CACCCUUGCUUUUACU-OH | 0.06 |
| V-iU$_{10}$U$_8$A$_3$ | CACCCUUGUUUUUACU-OH | 0.2 |
| V-iU$_{10}$U$_8$C$_5$A$_3$ | CACCCUUGUUUCUACU-OH | 0.2 |

*Sequences of V-wt, M-wt and V-d5' are shown in FIG. 2. All other RNAs are identical to V-d5' except for the indicated positions. The subscripted number indicates the distance from the 3' end of a change, and d and i refer to deleted or inserted nucleotides.

As shown in Table II, single point changes in V-d5' were equally well copied as compared to V-d5' itself, except for the V-A$_3$ RNA which was copied at 40% efficiency (FIG. 7, lane 10; Table II). When RNAs with two changes were tested, the activity generally dropped to very low levels (FIG. 7, lanes 3, 4, and 5). Therefore, these experiments confirmed that the specificity of the reactions for V-wt over M-wt was the result of the combination of the nucleotide changes present at the 3' terminus of M-wt.

6.2.7. Cap-Endonuclease Primed RNA Synthesis

The method of purifying the viral polymerase was modified in order to decrease loss of protein during dialysis. Rather than using the Amicon centricon-10 dialysis system, the enzyme was dialyzed in standard membranes resulting in higher concentrations of all four viral core proteins. The pattern of the protein gel of this preparation was identical to that shown in FIG. 1, lane 4, except that there is no BSA-derived band. It was found that 5 μl of this preparation, containing 150 ng of NP and 5 ng total of the three polymerase proteins, reacted optimally with 10 to 40 ng of model RNA template. However, the use of higher levels of protein increased the background, possibly due to higher levels of contaminating RNAs (virion RNAs not removed by CsCl centrifugation) yielding products of the size class around 50–75 nt, complicating analysis of RNA templates containing a length of 50 nt.

This high concentration polymerase preparation was now active in cap-endonuclease primed RNA synthesis (FIG. 8A, lane 4) and also in primer-independent replication of the template RNA (FIG. 8A, lane 2). When globin mRNA was used as primer for transcription from the 30 nt V-d5' template, a triplet of bands of size about 42 to 44 nt was apparent as product (FIG. 8A, lane 4), consistent with cleavage of the cap structure at about 12 nt from the 5' end of the mRNA and use of this oligonucleotide to initiate synthesis from the 30 nt model template. Since excess RNA inhibits RNA synthesis, probably via nonspecific binding of NP in vitro as discussed above, the optimal amount of cap donor RNA added to each reaction was found to be 100 ng, which is much lower than is usually used with preformed RNP structures (e.g., Bouloy, et al., 1980, Proc. Natl. Acad. Sci. USA 77: 3952–3956). The most effective primer was ApG (FIG. 8A, lane 5 and lighter exposure in lane 6). The product migrates slower than that of the input template (FIG. 8A, lane 1) or the product in the absence of primer (FIG. 8A, lane 2) probably since the 5' terminus of the ApG product is unphosphorylated. The intensity of the ApG-primed product was about ten-fold higher than that of the cap-primed product, but at 0.4 mM, ApG was at a 60,000-fold molar excess of the concentration of the cap donors. Thus, although the intensity of the product band from cap-priming was about ten-fold lower than that from ApG priming, the cap-primed reaction was about 6000-fold more efficient on a molar basis. This value is similar to the approximately 4000-fold excess efficiency observed previously for the viral polymerase (Bouloy, et al., 1980, Proc. Natl. Acad. Sci. USA 77: 3952–3956). It has been previously shown that cap donor RNAs containing a cap 0 structure, as in BMV RNA, are about ten-fold less active in priming the influenza viral polymerase (Bouloy, et al., 1980, Proc. Natl. Acad. Sci. USA 77: 3952–3956). This unusual cap specificity was shared by the reconstituted RNPs studied here as the specific product from the model RNA was greatly decreased in reactions containing BMV RNA as cap donor. A 30 nt product was observed in lanes 2–4, probably due to primerless replication of the model template.

That the product RNAs were of the opposite sense of the input template V-ds' was shown by nuclease S1 analysis (FIG. 8B). The ApG-primed (FIG. 8B, lanes 1 and 2) and the primerless (FIG. 8B, lanes 3 and 4) RNA products were essentially nuclease resistent. The product of the cap-primed reaction (FIG. 8B, lanes 5 and 6) was partially sensitive to nuclease as about 12 nt were digested from the product. These results were most consistent with the 5' 12 nt being of mRNA origin as has been shown many times for influenza virus- specific mRNA synthesis.

The promoter specificity of this polymerase preparation in reactions primed with ApG was found to be essentially identical to those for the lower concentration enzyme as shown earlier. However, attempts thus far to perform similar analyses of promoter specificity with the primerless and cap-primed reactions have been frustrated by the comparatively high levels of background, thus making quantitation difficult.

6.2.8. Replication of Genomic Length RNA Templates

A full-length 890 nt RNA identical to the sequence of A/WSN/33 segment 8 was prepared by T7 RNA polynierase transcription of plasmid DNA, pHgaNS, which had been digested with restriction endonuclease Hgal. This RNA was copied in ApG-primed reactions containing 10 µl of the high concentration polymerase (FIG. 9, lane 8). That the RNA was in fact a copy of the template was demonstrated by its resistance to nuclease SI (FIG. 9, lane 9). A similar product was observed in the absence of primer (FIG. 9, lanes 2 and 3). Confirmation that these product RNAs were full length copies of the template was done by RNase T1 analysis. Virion RNA purified from phenol-extracted A/PR/8/34 virus was similarly copied in ApG primed reaction (FIG. 9, lanes 10 and 11) and in the absence of primer (FIG. 9, lanes 4 and 5). Interestingly, the product from replication of the HA gene was at greatly reduced levels. The 3' end of this RNA differs from that of segment 8 only at nucleotides 14 and 15, suggesting importance for these nucleotides in the promoter for RNA synthesis. In addition, we found that when whole viral RNA was used in the reconstituted RNPs, the level of acid precipitable counts was about 70% of that observed with native RNPs. The viral polymerase was also able to copy these full length RNAs when globin mRNA was used in cap-primed reaction.

7. EXAMPLE: EXPRESSION AND PACKAGING OF A FOREIGN GENE BY RECOMBINANT INFLUENZA VIRUS

The expression of the chloramphenicol transferase gene (CAT) using rRNPs is described. The rRNPs were prepared using pIVACAT (originally referred to as pCATcNS), a recombinant plasmid containing the CAT gene. The pIVACAT plasmid is a pUC19 plasmid containing in sequence: the T7-promoter; the 5'-(viral-sense) noncoding flanking sequence of the influenza A/PR8/34 RNA segment 8 (encodes the NS proteins); a BgII cloning site; the complete coding sequence of the chloramphenicol transferase (CAT) gene in the reversed and complemented order; the 3'- (viral-sense) noncoding NS RNA sequence;

and several restriction sites allowing run-off transcription of the template. The pIVACAT can be transcribed using T7 polymerase to create an RNA with influenza A viral-sense flanking sequences around a CAT gene in reversed orientation.

The in vivo experiments described in the subsections below utilized the recombinant RNA molecule described containing sequences corresponding to the untranslated 3' and 5' terminal sequences of the NS RNA of influenza virus A/PR/8/34 flanking the antisense-oriented open reading frame of the CAT gene. This RNA was mixed with purified influenza virus polymerase complex and transfected into MDCK (or 293) cells. Following infection with influenza A/WSN/33 virus, CAT activity was measured in the RNP-transfected cells and amplification of the gene was indicated. In addition, the recombinant influenza virus gene was packaged into virus particles, since CAT activity was demonstrated in cells following infection with the recombinant virus preparation.

7.1. Materials and Methods

In order to get the flanking sequences of the NS RNA fused to the coding sequence of the CAT gene, the following strategy was used. Two suitable internal restriction sites were selected, close to the start and stop codon of the CAT gene, that would allow the replacement of the sequences flanking the CAT gene in the pCM7 plasmid with the 3'- and 5'- NS RNA sequences. At the 5' end, a SfaNI site was chosen (which generates a cut 57 nt from the ATG), and at the 3'- end a ScaI site which generates a cut 28 nt from the end of the gene (stop codon included). Next, four synthetic oligonucleotides were made using an Applied Biosystems DNA synthesizer, to generate two double-stranded DNA fragments with correct overhangs for cloning. Around the start codon these oligonucleotides formed a piece of DNA containing a XbaI overhand followed by a HaI site and a PstI site, the 3'- (viral-sense) NS sequence immediately followed by the CAT sequence from start codon up to the SfaNI overhang (underscored). In addition a silent mutation was incorporated to generate an Acci site closer to the start codon to permit future modifications.

```
Xba I
   Hga I    Pst I                                 Acc
   5'-ctagacgccctgcagcaaaagcagggtgacaaagacataatggagaaaaaaatcac
   3'tgcgggacgtcgttttcgtcccactgtttctgtattacctctttttttagtg
I           SfaN I
tgggtataccaccgttgatatatcccaatcgcatcgtaaa-3'             oligo2
acccatatggtggcaactatataggggttagcgtagcatttcttg-5'        oligo1
```

Around the stop codon the two other oligonucleotides generated a piece of DNA as follows: a blunt-ended SCAI site, the CAT sequence from this site up to and including the stop codon (underlined) followed by a BglII site and a Xba I overhang.

```
   Sca I                         Bgl II
   5'-actgcgatgagtggcagggcggggcgtaatagat-3'       oligo3
   3'-tgacgctactcaccgtcccgccccgcattatctagatc-5'   oligo4
                                  Xba I
```

Using a single internal EcoRI site in the CAT sequence, the SfaNI/EcoRI and the EcoRI/ScaI fragment from pCM7 were independently cut out and purified from acrylamide gels. The SfaNI/EcoRI fragment was subsequently ligated with the synthetic DNA fragment obtained by annealing oligonucleotides 1 and 2 into a pUC19 plasmid that was cut with XbaI and EcoRI. The EcoRI/ScaI fragment was similarly cloned into an XbaI and EcoRI-digested pUC19 plasmid using oligonucleotides 3 and 4. The ligated DNA was transformed into competent DH5a bacteria, amplified, isolated and screened by means of restriction analysis using standard techniques.

The recombinants with the SfaNI containing insert were cut with XbaI and EcoRI and the plasmids with the ScaI insert were cut with EcoRI and BglII. The fragments were purified from acrylamide gel and cloned together into the pPHV vector which had been cut with XbaI and BglII. After transformation, white colonies were grown, analyzed by endonuclease digestion and selected clones were sequenced. The final clone, pCATcNS2, was grown in large amounts and sequenced from the flanking pUC sequences up to 300 nt into the CAT gene, revealing no discrepancies with the intended sequence, with the exception of a G to A transition in the CAT gene, which appeared silent.

7.1.1. Viruses and Cells

Influenza A/PR/8/34 and A/WSN/33 viruses were grown in embryonated eggs and MDCK cells, respectively (Ritchey et al. 1976, J. Virol. 18: 736–744; Sugiura et al., 1972, J. Virol. 10: 639–647). RNP-transfections were performed on human 293 cells (Graham et al., 1977, J. Gen. Virol. 36: 59–72) and on Madin-Darby canine kidney (MDCK) cells (Sugiura et al., 1972, supra).

7.1.2. Construction of Plasmids

Plasmid pIVACAT1, derived from pUC19, contains the coding region of the chloramphenicol acetyltransferase (CAT) gene flanked by the noncoding sequences of the influenza A/PR/8/34 RNA segment 8. This construct is placed under the control of the T7 polymerase promoter in such a way that the RNA transcript IVACAT1 contains in 5to 3' order: 22 nucleotides derived from the 5' terminus of the influenza virus NS RNA, an 8 nt linker sequence including a BglII restriction site, the CAT gene in negative polarity, and 26 nt derived form the 3' end of the influenza virus NS RNA (FIG. 11).

pIVACAT1 was constructed in the following way: In order to obtain the correct 5'-end in pIVACAT1, the EcoRI-ScaI fragment of the CAT gene derived from plasmid pCM7 (Pharmacia) was ligated to a DNA fragment formed by two synthetic oligonucleotides. The sequence of these oligonucleotides are:

5'- ACTGCGATGAGTGGCAGGGCGGGGCGTAATA — GAT-3'

(top strand), and

5'- CTAGATCTATTACGCCCCGCCCTGCCAC — TCATCGCAGT-3'

(bottom strand). For the 3'-end of the insert in pIVACAT1 the SfaN 1-EcoRI fragment of the CAT gene was ligated to a DNA fragment made up of the synthetic oligonucleotides:

5'- CTAGACGCCCTGCAGAAAAGCAGGGTGAC — AAAGACA TAATGGAGAAAAAAAATCACTGGGTATACCACCGTTGATAT ATCCCAATCG — CATCGTAAA-3'

(top strand), and

5'- GTTCTTTACGATGCGATTGGGAT — TTTGCTGCAGGGCGT-3'

(bottom strand). Oligonucleotides were synthesized on an Applied Biosystems DNA synthesizer. These 5' and 3' constructs were ligated into pUC19 shuttle vectors digested with XbaI and EcoRI, grown up, cut out with EcoRI/BlII (5' region) and XbaI/EcoRI (3' region) and ligated into BlII/XbaI cut pPHV. The latter plasmid is similar to pV-WT described in Section 6, supra, except that it contains a BglII site which separates the noncoding terminal sequences of the influenza A virus NS RNA segment. The final clone pIVACAT1 (FIG. 1) was grown up and the DNA was partially sequenced starting from the flanking pUC sequences and reaching into the CAT gene. No changes were found as compared to the expected sequences with the exception of a silent G to A transition in the CAT gene at position 106 relative to the start of the IVACAT1 RNA.

7.1.3. T7 RNA Transcription

Plasmid pIVACAT1 was digested with HgaI (FIG. II), to allow run-off transcription. The 5 nt overhang generated by this enzyme was filled in with Klenow enzyme (BRL) and the DNA was purified over a spin column (Boehringer). The T7 polymerase reaction was performed using standard procedures in the presence of Rnasin (Promega). Template DNA was removed from Rnase free Dnase I (Promega). The RNA was purified over Qiagen tip-5 columns (Qiagen, Inc.) and quantitated using 4% polyacrylamide gels which were silver stained. NS RNA was prepared from plasmid pHgaNS in the same way.

7.1.4. Purification of Influenza A Virus Polymerase and In Vitro Transcription

The RNA polymerase complex was purified from influenza A/PR/8/34 as described in Section 6, supra. In vitro transcriptions of cold IVACAT1 or HgaNS RNA template were carried out using the conditions which have been described in Section 6, supra. Radiolabeled transcripts were analyzed on 4% acrylamide gels.

7.1.5. RNP-Transfection of MDCK and 293 Cells 35 mm dishes containing approximately $10^6$ cells were treated with 1 ml of a solution of 300 µg/ml DEAE-dextrin, 0.5% DMSO in PBS/gelatine (0.1 mg/ml gelatine) for 30 minutes at room temperature. After removal of this solution, 200 μg of μl PBS/gelatine containing 1 μg IVACAT 1 RNA (1–2 μl), 20 μl of the purified polymerase preparation and 4 μl of Rnasin was added to the cells and incubated for 1 hour at 37° C. This was followed by the addition of gradient purified influenza A/WSN/33 virus (moi 2–10). After incubation for one hour at 37° C., 2.5 ml of either DMEM+10% FCS media (293 cells) or MEM media (MDCK cells) was added. In some experiments MDCK cells were first infected and subsequently RNP-transfected. Harvesting of cells was done in NET buffer or in media, using a rubber policemen (MDCK cells), or by gentle suspension (293 cells). Cells were spun down and the pellets were resuspended in 100 μl of 0.25 M Tris buffer, pH 7.5. The samples were subsequently freeze-thawed three-times and the cell debris was pelleted. The supernatant was used for CAT assays.

7.1.6. Passaging of Virus from RNP-Transfected Cells

MDCK cells were infected with helper virus and RNP-transfected 2 hours later as described above. After 1 hour cells and media were collected and cells were spun down. 100 μl of the supernatant media, containing virus, was added to 35 mm dishes with MDCK cells. After 12 hours these cells and media were collected and assayed for CAT activity. Virus contained in this supernatant media was used for subsequent rounds of infection of MDCK cells in 35 mm dishes.

7.1.7. CAT Assays

CAT assays were done according to standard procedures, adapted from Gorman et al., 1982, Mol. Cell. Biol. 2: 1044–1051. The assays contained 10 μl of $^{14}$C chloramphenicol (0.5 μCi; 8.3 nM; NEN), 20 μl of 40 mM acetyl CoA (Boehringer) and 50 μl of cell extracts in 0.25M Tris buffer (pH 7.5). Incubation times were 16–18 hours.

7.2. Results rRNA templates were prepared from HgaI digested, end filled linearized pCATcNS using the bacteriophage T7 RNA polymerase as described in Section 6. The rRNA templates were combined with the viral RNA polymerase complex prepared as described in Section 6.1.1., and the resulting rRNPs were used to transfect MDCK and 293 cells lines which were superinfected with influenza A/WSN33. In each cell line transfected with the rRNPs, high levels of expression of CAT was obtained 6 hours post-infection. In addition, virus stocks obtained 24 hours post-infection synthesized high levels of CAT enzyme after subsequent passage in MDCK cells. The CAT-RNP was packaged into virus particles.

7.2.1. Synthesis of IVACAT1 Template RNA

In order to study the transcription and replication signals of influenza A virus RNAs in vivo, we constructed plasmid pIVACAT1 (FIG. II) which directs the synthesis of an NS RNA-like transcript. This RNA shares the 22 5' terminal and the 26 3' terminal nucleotides with the NS RNA of influenza A/PR/8/34 virus and contain—instead of the coding sequences for the NS1 and NS2 proteins—those for a full-length CAT protein. For cloning purposes it also contains eight additional nucleotides including a BglII site between the stop codon of the CAT gene and the stretch of U's in the 5' noncoding region. The 17 promoter adjacent to the 5' noncoding sequences and the HgaI site downstream of the 3' end allow for the exact tailoring of the 5' and 3' ends. Run-off transcription using T7 polymerase generates a 716 nt long RNA: FIG. 12, lanes 2–4 show that this RNA is of discrete length and shorter than the 890 nt long marker NS RNA, which was synthesized by T7 transcription of pHgaNS (lane 1).

7.2.2. The IVACAT1 RNA is Transcribed In Vitro by the Influenza a Virus RNA Polymerase In the examples described in Section 6, it was demonstrated that synthetic RNAs containing at the 3' end the 15 3' terminal nucleotides of influenza virus RNA segment 8 can be transcribed in vitro using purified influenza A virus RNA polymerase. We tested whether unlabeled IVACAT1 RNA could be transcribed in a similar way. FIG. 12 lane 5 shows that the in vitro transcription reaction generated an RNA of discrete length and similar size to the product of the T7 transcription reaction suggesting synthesis of a full length product.

7.2.3. RNP-Transfection and CAT Activity

Since the recombinant CAT RNA could be transcribed in vitro, a system was designed to test whether this RNA can be recognized and replicated in vivo (FIG. 13). Recombinant RNA was mixed with the purified polymerase to allow formation of viral RNP-like particles. To facilitate the association, the RNA/polymerase mixture was incubated in transcription buffer without nucleotides for 30 minutes at 30° C. prior to RNP-transfection. In some experiments, this preincubation step was omitted. RNP-transfections were either preceded or followed by infection with influenza A/WSN/33 virus, since the production of viral polymerase protein was expected to be necessary for efficient amplification of the gene. The cells used were either MDCK cells, which are readily susceptible to influenza A/WSN/33 virus infection, or human 293 cells, which support infection at a slower rate.

In order to determine whether the minus sense IVACAT1 RNA could be amplified and transcribed in vivo, an experiment was performed in 293 cells. Cells were transfected with RNP, virus infected one hour later and harvested at various times post-infection. FIG. 14A shows that at early times post infection only background levels of CAT activity were detected (lanes 5, 7 and 9). However, significant levels of CAT activity appeared seven hours after virus infection (lane 11) A similar level of CAT activity was detected two hours later (lane 13). There were background levels of CAT activity in the mock transfected 5 cells at any time point (lanes 6, 8, 10, 12 and 14), and in control cells not infected with A/WSN/33 virus (lanes 1–4).

Preincubation of RNA and polymerase complex was not necessary for successful RNP-transfection. As can be seen in FIG. 14B, lanes 2 and 3, preincubation might actually cause a decrease in CAT activity, presumably due to RNA degradation during preincubation. In another control experiment, infection by helper virus of RNP-transfected cells was omitted (FIG. 14B, lanes 4 and 5). Since these lanes show no CAT activity we conclude that the IVACAT1 RNA is amplified specifically by the protein machinery supplied by the helper virus. In an additional control experiment, naked RNA was transfected into cells which were subsequently helper-infected or mock-infected. Again, no CAT activity was detected in these samples (FIG. 14B, lanes 6–9). Finally virus-infected cells which were not transfected with recombinate CAT-RNP also did not exhibit endogenous acetylation activity (FIG. 14B, lane 10). It thus appears that addition of the purified polymerase to the recombinant RNA as well as infection of cells by helper virus is important for successful expression of the CAT enzyme.

Experiments were also performed using MDCK cells, the usual tissue culture host cell for influenza virus (FIG. 14C). When the reconstituted recombinant CAT-RNP complex was transfected I hour before virus infection, little CAT activity was observed at 7 hours post virus infection (FIG.

14C, lane 1). When RNP-transfection was accomplished 2 hours after virus infection, expression of CAT was greatly enhanced at 7 hours post-virus infection (FIG. 14C, lane 3). Therefore, MDCK cells are also viable host cells for these experiments.

7.2.4. The CAT-RNP is Packaged into Virus Particles

Since the recombinant CAT RNA can be replicated in vivo via helper virus functions, we examined whether virus produced in RNP-transfected and helper virus infected cells contained the CAT gene. MDCK cells were used in the experiment because they yield higher titers of infectious virus than 293 cells. MDCK cells were infected with A/WSN/33 virus, RNP-transfected 2 hours later and allowed to incubate overnight. At 14 hours post infection, media was harvested and cells were pelleted. Virus supernatant was then used to infect new MDCK cell monolayers. The inoculum was removed after 1 hour and cells were harvested at 12 hours post infection and assayed for CAT activity. FIG. 15 reveals that the virus preparation induces a level of CAT activity (lanes 2 and 3) which is significantly above control (lane 1). In this case, the addition of helper virus to the inoculum did not increase CAT activity (lane 4). Further passaging of supernatant virus on fresh MDCK cells did not result in measurable induction of CAT activity. This is not surprising as there is no selective pressure for retaining the CAT gene in these viral preparations. We excluded the possibility that we were transferring the original RNA/polymerase complex by pretreating the inocula with RNase. This treatment destroys viral RNPs of influenza virus (Pons et al., 1969, Virology 39: 250–259; Scholtissek and Becht, 1971 J. Gen. Virol. 10: 11–16).

8. RESCUE OF INFECTIOUS INFLUENZA VIRUSES USING RNA DERIVED FROM SPECIFIC RECOMBINANT DNAs

The experiments described in the subsections below demonstrate the rescue of infectious influenza viruses using RNA which is derived from specific recombinant DNAs. RNAs corresponding to the neuraminidase (NA) gene of influenza A/WSN/33 virus (WSN virus) were transcribed in vitro from appropriate plasmid DNAs and—following the addition of purified influenza virus polymerase complex (as described in Section 6.1.1. supra)—were transfected into MDBK cells as described in Section 7, supra. Superinfection with helper virus, lacking the WSN NA gene, resulted in the release of viruses containing the WSN NA gene. Thus, this technology allows the engineering of infectious influenza viruses using cDNA clones and site-specific mutagenesis of their genomes. Furthermore, this technology may allow for the construction of infectious chimeric influenza viruses which can be used as efficient vectors for gene expression in tissue culture, animals or man.

The experiments described in Sections 6 and 7 supra, demonstrate that the 15 3' terminal nucleotides of negative strand influenza virus RNAs are sufficient to allow transaction in vitro using purified influenza virus polymerase proteins. In addition, the studies using the reporter gene chloramphenicol acetyltransferase (CAT) show that the 22 5' terminal and the 26 3' terminal nucleotides of the viral RNAs contain all the signals necessary for transcription, replication and packaging of influenza virus RNAs. As an extension of these results, a plasmid, pT3NAv, was constructed which contained the complete NA gene of influenza A/WSN/33 virus downstream of a truncated T3 promoter (FIG. 16). Therefore, runoff transcription of this plasmid, cut at the Ksp632I site, yields an RNA which is identical to the true genomic NA gene of the WSN virus (FIG. 17, lane 3). This RNA was then incubated with purified polymerase (purified as described in Section 6.1.1) and used in a ribonucleoprotein (RNP) transfection experiment to allow the rescue of infectious virus using helper virus which did not contain the WSN virus NA. The choice of WSN-HK helper virus was based on the need for a strong selection system by which to isolate a rescued virus. Previously, it was shown that the WSN-HK virus can only form plaques in MDBK cells when protease is added to the medium. This is in marked contrast to WSN virus (isogenic to WSN-HK virus except for the neuraminidase gene), which in the absence of protease readily replicates in MDBK cells and forms large, easily visible plaques (Schulman et al., 1977, J. Virol. 24: 170–176).

8.1. Materials and Methods

8.1.1. Viruses and Cells

Influenza A/WSN/33 virus and A/WSN-HK virus were grown in Madin-Darby canine kidney (MDCK) cells and embryonated eggs, respectively (Sugiura et al., 1972, J. Virol. 10: 639–647; Schulman et al., 1977, J. Virol. 24: 170–176). Influenza A/PR/8/34 virus was also grown in embryonated eggs. Madin-Darby bovine kidney (MDBK) cells were used for the transfection experiments and for selection of rescued virus (Sugiura et al., 1972, J. Virol. 10: 639–647).

8.1.2. Construction of Plasmids

The pT3NAv, pT3NAv mut 1 and pT3NAv mut 2 plasmids were constructed by PCR-directed mutagenesis using a cloned copy of the WSN NA gene, which was obtained following standard procedures (Buonagurio et al., 1986, Science 232: 980–982). To construct pT3NAv, the following primers were used:

5'-CGGAATTCTCTTCGAGCGAAAGCAGGAGTT-3' and

5'-CCAAGCTTATTAACCCTCACTAAAAGTAGAAACAAGGAGTTT-3'.

After 35 cycles in a thermal cycler (Coy Lab Products, Mich.), the PCR product was digested with EcoRI and HindIII and cloned into pUC19. Plasmid pT3NAv mut 1 was constructed in a similar fashion except that the sequence of the primer was altered (FIG. 16). Plasmid pT3NAv mut 2 was constructed by cassette mutagenesis through the digestion of pT3NAv with PstI and NcoI and religation in the presence of the synthetic oligonucleotides—

5'-CATGGGTGAGTTTCGACCAAAATCTAGATTATAAAATAGGATACATATGCA-3' and 5'-AATGTATCCTATTTTATAATCTAGATTTTGGTCGAAACTCACC-3.

Oligonucleotides were synthesized on an applied Biosystems DNA synthesizer. The final clones pT3NAv, pT3NAv mut 1 and pT3NAv mut 2 were grown up and the DNAs were partially sequenced starting from the flanking pUC 19 sequences and reaching into the coding sequences of the NA gene. The mutations in pT3NAv mut 2 were also confirmed by sequencing.

8.1.3. Purification of Influenza a Virus Polymerase and RNP Transfection in MDBK Cells The RNA polymerase complex was purified from influenza A/PR/8/34 virus as described in Section 6. 1. 1, supra, and was then used for RNP transfection in MDBK cells using the protocol described in Section 7, supra, except that WSN-HK virus was used as helper virus at an moi of 1. RNAs used for RNP transfection were obtained by phenol extraction of purified virus or by transcription (using T3 polymerase) of pT3NAv, pT3NAv mut 1 and pT3NAv mut 2. All plasmids were digested with Ksp632I, end-filled by Klenow enzyme (BRL) and then transcribed in a runoff reaction a described in Section 7, supra.

8.2. Results

8.2.1. Rescue of Infectious Influenza Virus in MDBK Cells Using RNA Derived from Recombinant Plasmid DNA A plasmid, pT3NAv, was constructed to contain the complete NA gene of influenza WSN virus downstream of a truncated T3 promoter (FIG. 16). Runoff transcription of the plasmid, cut at the Ksp632I site, yields an RNA which is identical in length to the true genomic NA gene of the WSN virus (FIG. 17, lane 3). This RNA was then incubated with purified polymerase and used in a ribonucleoprotein (RNP) transfection experiment to allow the rescue of infectious virus using helper virus. The choice of WSN-HK virus as helper virus was based on the need for a strong selection system by which to isolate a rescued virus. Previously, its was shown that the WSN-HN virus can only form plaques in MDBK cells when protease is added to the medium (Schulman et al., 1977, J. Virol. 24: 170–176). This is in marked contrast to WSN virus (isogenic to WSN-HK helper virus except for the neuraminidase gene), which in the absence of protease readily replicates in MDBK cells and forms large, easily visible plaques (Sugiura et al., 1972, J. Virol. 10: 639–647). MDBK cells were first infected with the WSN-HK helper virus and RNP-transfected one hour after virus infection. Following overnight incubation in the presence of 20µg/ml plasminogen, supernatant from these cells was then amplified and plaqued in MDBK cells in the absence of protease in the medium. The appearance of plaques in MDBK cells (Schulman et al., 197, J. Virol. 10: 639–647) indicated the presence of virus which contained the WSN virus NA gene, since supernatant from control experiments of cells infected only with the WSN-HK virus did not produce plaques. In a typical experiment involving the use of a 35 mm dish for the RNP-transfection, $2.5 \times 10^2$ plaques were observed.

In another control experiment, synthetic NA RNA was used which was derived from plasmid pT3NAv mut 1 (FIG. 16). This RNA differs from the wild type NA RNA derived from pT3NAv by a single nucleotide deletion in the non-translated region of the 5' end (FIG. 16). RNP-transfection of MDBK cells with this RNA and superinfection with WSN-HK virus did not result in the formation of rescued virus. This negative result is readily explained since we have shown in Section 6 and 7, supra, that the essential sequences for the recognition of viral RNA by viral polymerases as well as the packaging signals are located within the 3' and 5' terminal sequences of the viral RNAs. However, we cannot exclude the possibility that rescue of virus using this mutated RNA does occur, albeit at an undetected frequency.

8.2.2. RNA Analysis of Rescued Virus

Virus obtained in the rescue experiment was plaque purified, amplified in MDBK cells and RNA was extracted from this preparation. The RNA was then analyzed by electrophoresis on a polyacrylamide gel. FIG. 17 shows the RNA of the helper virus WSN-HK (lane 1) and the synthetic NA RNA (lane 3), which was transcribe by T3 polymerase from plasmid pT3NAv. The migration pattern of the RNAs of the rescued virus (lane 2) is identical to that of control WSN virus (lane 4). Also, the NA RNAs in lanes 2 and 4 migrate at the same position as the NA RNA derived from cDNA (lane 3) and faster than the HK virus NA band in the helper WSN-HK virus (lane 1). These experiments support the conclusion that as a result of the RNP-transfection, infectious virus was formed containing WSN virus NA RNA derived from cDNA.

8.2.3. Rescue of Infectious Influenza Virus Using Virion RNA

In another transfection experiment, RNA extracted from purified WSN virus was employed. When this naked RNA is transfected together with the polymerase proteins into helper virus infected cells, rescue of WSN virus capable of replicating in MDBK cells is observed. RNA isolated from an amplified plaque in this experiment is analyzed in lane 5 of FIG. 17 and shows a pattern indistinguishable from that of the control of WSN virus in lane 4.

8.2.4. Introduction of Site-Specific Mutations into the Viral Genome

The experiments described so far involved the rescue of influenza WSN virus. Since the synthetic RNA used in these experiments is identical to the authentic WSN NA gene, the unlikely possibility of contamination by wild type WSN virus could not be rigorously ruled out. Therefore, we introduced five silent point mutations in the coding region of the NA gene in plasmid pT3NAv. These mutations were introduced by cassette mutagenesis through replacement of the short NcoI/PstI fragment present in the NA gene. The five mutations in the cDNA included a C to T change at position 901 and a C to A change at position 925, creating a new XbaI site and destroying the original PstI site, respectively. In addition, the entire serine codon at position 887–889 of the cDNA clone was replaced with an alternate serine triplet (FIG. 17). RMP-transfection of this mutagenized RNA (pT3NAv mut 2) and helper virus infection of MDBK cells again resulted in the rescue of a WSN-like virus which grew in MDBK cells in the absence of added protease. When the RNA of this virus was examined by sequence analysis, all five point mutations present in the plasmid DNA (FIG. 16) were observed in the viral RNA (FIG. 18). Since it is extremely unlikely that these mutations evolved in the wild type influenza WSN virus, we conclude that successful rescue of infectious influenza virus containing five site-specific mutations was achieved via RNP-transfection of engineered RNA.

9. RESCUE OF INFECTIOUS RESPIRATORY SYNCYTIAL VIRUSES (RSV) USING RNA DERIVED FROM SPECIFIC RECOMBINANT DNAs.

This example describes a process for the rescue of synthetic RNAs of infectious respiratory syncytial virus (RSV), derived from recombinant cDNAs of first portions of and then the entire RSV RNA genome into stable and infectious RSVs, as noted in Section 5 above. This process can be used in the production of chimeric RSV viruses which can express foreign genes, ie, genes non-native to RSV. Another exemplary way to achieve the production of chimeric RSV involves modifying existing, native RSV genes, as is further described. Accordingly, this example also describes the utility of this process in the directed attenuation of RSV pathogenicity, resulting in production of a vaccine with defined, engineered biological properties for use in humans.

The first step of the rescue process involving portions of the RSV genome requires synthesis of double strand DNA representing the 3' and 5'-terminal extracistronic regions of RSV strain A2 (leader and trailer respectively). The assembly of these extracistronic regions is described in more detail in Section 9.1.2. The bacterial CAT gene, the exemplary heterologous gene coding sequence used in this example, is then flanked with the leader and trailer DNAs to form a miniature RSV 'genome' with the leader region positioned closest to the CAT gene AUG (initiation codon for protein synthesis); see FIG. 21. RNA is transcribed in vitro from this DNA construct and transfected into helper virus-infected (RSV strain A2, or RSV strain B9320) 293 cells. The subsequent presence of CAT activity in these cells indicates the encapsidation, transcription and replication of the RSV/CAT RNA. It will be apparent to one skilled in the art that other heterologous sequences, such as for example, other foreign or non-native genes (i.e. genes from organisms or sources other than RSV), additional RSV genes, native RSV genes or regulatory sequences having specific substitutions, additions and/or deletions in the nucleotide sequence and/or gross alterations in the genetic structure of native RSV, that, in effect, result in heterologous sequences due to their alterations or modifications, can be substituted for the CAT sequence exemplified herein to produce a chimeric RSV.

The first step of the rescue process involving the entire RSV RNA genome requires synthesis of a full length copy of the 15 kilobase (kb) genome of RSV strain A2. This is accomplished by splicing together subgenomic double strand cDNAs (using standard procedures for genetic manipulation) ranging in size from 1 kb–3.5 kb, to form the complete genome cDNA. Determination of the nucleotide sequence of the genome cDNA allows identification of errors introduced during the assembly process; errors can be corrected by site directed mutagenesis, or by substitution of the error region with a piece of chemically synthesized double strand DNA. Following assembly, the genome cDNA is positioned adjacent to a transcriptional promoter (e.g., the T7 promoter) at one end and DNA sequence which allows transcriptional termination at the other end, e.g., a specific endonuclease or a ribozyme, to allow synthesis of a plus or minus sense RNA copy of the complete virus genome in vitro or in cultured cells.

The rescue process utilizes the interaction of full length RSV strain A2 genome RNA, which is transcribed from the constructed cDNA, with helper RSV subgroup B virus proteins inside cultured cells. This can be accomplished in a number of ways. For example, full length virus genomic RNA from RSV strain A2 can be transcribed in vitro and transfected into RSV strain B9320 infected cells, such as 293 cells using standard transfection protocols. In addition, in vitro transcribed genomic RNA from RSV strain A2 can be transfected into a cell line expressing the essential RSV strain A2 proteins (in the absence of helper virus) from stably integrated virus genes.

Alternatively, in vitro transcribed virus genome RNA (RSV strain A2) can also be transfected into cells infected with a heterologous virus (e.g. in particular vaccinia virus) expressing the essential helper RSV strain A2 proteins, specifically the N, P and L proteins. In addition the in vitro transcribed genomic RNA may be transfected into cells infected with a heterologous virus, for. example vaccinia virus, expressing T7 polymerase, which enables expression of helper proteins from transfected plasmid DNAs containing the helper N, P and L genes.

As an alternative to transfection of in vitro transcribed genomic RNA, plasmid DNA containing the entire RSV cDNA construct may be transfected into cells infected with a heterologous virus, for example vaccinia virus, expressing the essential helper RSV strain A2 proteins and T7 polymerase, thereby enabling transcription of the entire RSV genomic RNA from the plasmid DNA containing the RSV cDNA construct. The vaccinia virus need not however, supply the helper proteins themselves but only the T7 polymerase; then helper proteins may be expressed from transfected plasmids containing the RSV N, P and L genes, appropriately positioned adjacent to their own T7 promoters.

Where replicating virus is providing the helper function during rescue experiments, the B9320 strain of RSV is used, allowing differentiation of progeny rescued RSV strain A2 and helper virus RSV strain B9320 with neutralizing monoclonal antibodies directed against RSV B9320. Rescued RSV strain A2 is positively identified by the presence of specific nucleotide 'marker' sequences inserted in the cDNA copy of the RSV genome prior to rescue.

The establishment of a rescue system for native, ie, 'wild-type' RSV strain A2 allows modifications to be introduced into the cDNA copy of the RSV genome to construct chimeric RSV containing sequences heterologous in some manner to that of native RSV, such that the resulting rescued virus may be attenuated in pathogenicity to provide a safe and efficacious human vaccine as discussed in Section 5.4 above. The genetic alterations required to cause virus attenuation may be gross (e.g. translocation of whole genes and/or regulatory sequences within the virus genome), or minor (e.g. single or multiple nucleotide substitution(s), addition(s) and/or deletion(s) in key regulatory or functional domains within the virus genome), as further described in detail.

In addition to alteration(s) (including alteration resulting from translocation) of the RSV genetic material to provide heterologous sequence, this process permits the insertion of 'foreign' genes (i.e., genes non-native to RSV) or genetic components thereof exhibiting biological function or antigenicity in such a way as to give expression of these genetic elements; in this way the modified, chimeric RSV can act as an expression system for other heterologous proteins or genetic elements, such as ribozymes, anti-sense RNA, specific oligoribonucleotides, with prophylactic or therapeutic potential.

9.1 Rescue of the Leader and Trailer Sequences of RSV Strain A2 Using RSV Strain B9320 as Helper 9.1.1. Viruses and Cells Although RSV strain A2 and RSV strain B9320 was used in this Example, they are exemplary. It is within the skill in the art to use other strains of RSV subgroup A and RSV subgroup B viruses in accordance with the teachings of this Example. Methods which employ such other strains are encompassed by the invention.

RSV strain A2 and RSV strain B9320 were grown in Hep-2 cells and Vero cells respectively, and 293 cells were used as host during transfection/rescue experiments. All three cell lines were obtained from the ATCC (Rockville, Md.). The RSV strain A2 was also obtained from the ATCC and RSV strain B9320 was a gift from Dr. M. Hendry at the Department of Health Services, Berkeley, Calif.

9.1.2. Construction of Plasmids

Plasmid pRSVA2CAT (FIG. 21) was constructed as described below.

The cDNAs of the 44 nucleotide leader and 155 nucleotide trailer components of RSV strain A2 (see Mink et al., *Virology* 185:615–624 (1991); Collins et al., *Proc. Natl.*

*Acad. Sci.* 88:9663–9667 (1991)), the trailer component also including the promoter consensus sequence of bacteriophage T7 polymerase, were separately assembled by controlled annealing of oligonucleotides with partial overlapping complementarity (see FIG. 21). The oligonucleotides used in the annealing were synthesized on an Applied Biosystems DNA synthesizer (Foster City, Calif.). The separate oligonucleotides and their relative positions in the leader and trailer sequences are indicated in FIG. 21. The oligonucleotides used to construct the leader were:

1. 5' CGA CGC ATA TTA CGC GAA AAA ATG CGT ACA ACA AAC TTG CAT AAA C 2. 5' CAA AAA AAT GGG GCA AAT AAG AAT TTG ATA AGT ACC ACT TAA ATT TAA CT 3. 5' CTA GAG TTA AAT TTA AGT GGT ACT 4. 5' TAT CAA ATT CTT ATT TGC CCC ATT TTT TTG GTT TAT GCA AGT TTG TTG TA 5. 5' CGC ATT TTT TCG CGT AAT ATG CGT CGG TAC

The oligonucleotides used to construct the trailer were:

1. 5' GTA TTC AAT TAT AGT TAT TAA AAA TTA AAA ATC ATA TAA TTT TTT AAA TA 2. 5' ACT TTT AGT GAA CTA ATC CTA AAG TTA TCA TTT TAA TCT TGG AGG AAT AA 3. 5' ATT TAA ACC CTA ATC TAA TTG GTT TAT ATG TGT ATT AAC TAA ATT ACG AG
4. 5' ATA TTA GTT TTT GAC ACT TTT TTT CTC GTT ATA GTG AGT CGT ATT A
5. 5' AGC TTA ATA CGA CTC ACT ATA ACG A
6. 5' GAA AAA AAG TGT CAA AAA CTA ATA TCT CGT AAT TTA GTT AAT ACA CAT AT
7. 5' AAA CCA ATT AGA TTA GGG TTT AAA TTT ATT CCT CCA AGA TTA AAA TGA TA
8. 5' ACT TTA GGA TTA GTT CAC TAA AAG TTA TTT AAA AAA TTA TAT GAT TTT TA
9. 5' ATT TTT AAT AAC TAT AAT TGA ATA CTG CA

The complete leader and trailer cDNAs were then ligated to the CAT reporter gene XbaI and PstI sites respectively to form a linear~1 kb RSV/CAT cDNA construct. This cDNA construct was then ligated into the KpnI and HindIII sites of pUC19. The integrity of the final pRSVA2CAT construct was checked by gel analysis of the size of XbaI/PstI and KpnI/HindIII digestion products.

In vitro transcription of HgaI linearlized pRSVA2CAT with bacteriophage T7 polymerase was performed according to the T7 supplier protocol (Promega Corporation, Madison, Wis.). Confluent 293 cells in six-well dishes (~$1\times10^6$ cells per well) were infected with RSV strain B9320 at 1 pfu $cell^{-1}$ and 1 hour later were transfected with 5–10 $\mu$g of the in vitro transcribed RNA from the pRSVA2CAT construct. The transfection procedure followed the transfection procedure of Collins et al., *Virology* 195:252–256 (1993) and employed Transfect/ACE™ and Optimem reagents according to the manufacturers specifications (Gibco-BRL, Bethesda, Md.). At 24 hours post infection the 293 cells were assayed for CAT activity using a standard protocol (Current Protocols in Molecular Biology, Vol. 1, Chapter 9.6.2; Gorman, et al., (1982) Mol. Cell. Biol. 2:1044–1051). The detection of high levels of CAT activity indicated that in vitro transcribed negative sense RNA containing the 'leader' and 'trailer' regions of the RSV A2 strain genome and the CAT gene can be encapsidated, replicated and expressed using proteins supplied by RSV strain B9320 (See FIG. 22). The level of CAT activity observed in these experiments was at least as high as that observed in similar rescue experiments where homologous RSV strain A2 was used as helper virus. This ability of an antigenically distinct subgroup B RSV strain B9320 to support the encapsidation, replication and transcription of a subgroup A RSV strain A2 RNA has to our knowledge hitherto not been formally reported. In view of the fact that influenza B virus is unable to provide analogous helper activity for similar CAT constructs containing influenza A leader and trailer sequences, these observations are therefore surprising and unexpected.

9.2 Construction and Rescue of a cDNA Representing the Complete Genome of RSV To obtain a template for cDNA synthesis, RSV genomic RNA, comprising 15,222 nucleotides, is purified from infected Hep-2 cells according to the method described by Ward et al., *J. Gen. Virol.* 64:1867–1876 (1983). Based on the published nucleotide sequence of RSV, oligonucleotides are synthesized using an Applied Biosystems DNA synthesizer (Applied Biosystems, Foster City, Calif.) to act as primers for first and second strand cDNA synthesis from the genomic RNA template. The nucleotide sequences and the relative positions of the cDNA primers and key endonuclease sites within the RSV genome are indicated in FIG. 23. The production of cDNAs from virus genomic RNA is carried out according to the reverse transcription/polymerase chain reaction (RT/PCR) protocol of Perkin Elmer Corporation, Norwalk, Conn. (see also Wang et al., (1989) *Proc. Natl. Acad. Sci.* 86:9717–9721); the amplified cDNAs are purified by electro elution of the appropriate DNA band from agarose gels. Purified DNA is ligated directly into the pCRII plasmid vector (Invitrogen Corp. San Diego), and transformed into either 'One Shot' *E. coli* cells (Invitrogen) or 'SURE' *E. coli* cells (Stratagene, San Diego). The resulting, cloned, virus specific, cDNAs are assembled by standard cloning techniques (Sambrook et al., *Molecular Cloning—A Laboratory manual*, Cold Spring Harbor Laboratory Press (Cold Spring Harbor, N.Y., 1989) to produce a cDNA spanning the complete RSV genome. The entire cDNA genome is sequenced, and incorrect sequence replaced by either site-directed mutagenesis or chemically synthesized DNA. Nucleotide substitutions are introduced at bases 7291 and 7294 (with base number 1 being at the start of the genomic RNA 3' end) in the 'F' gene, to produce a novel StuI endonuclease site, and at positions 7423, 7424, and 7425 (also in the F gene) to produce a novel PmeI site. These changes are designed to act as definitive markers for rescue events. The bacteriophage T7 polymerase and the HgaI endonuclease site are placed at opposite ends of the virus genome cDNA such that either negative or positive sense virus genome RNA can be synthesized in vitro. The cDNAs representing the T7 polymerase promoter sequence and the recognition sequence for HgaI were synthesized on an Applied Biosystems DNA synthesizer and are separately ligated to the ends of the virus genome cDNA, or are added as an integral part of PCR primers during amplification of the terminal portion of the genome cDNA, where appropriate; the latter procedure is used when suitable endonuclease sites near the genome cDNA termini are absent, preventing direct ligation of chemically synthesized T7 promoter/HgaI site cDNA to the genome cDNA. This complete construct (genome cDNA and flanking T7 promoter/HgaI recognition sequence) is then cloned into the KpnI/NotI sites of the Bluescript II SK phagemid (Stratagene, San Diego) from which the endogenous T7 promoter has been removed by site-directed mutagenesis. RNA transcribed from this complete genome construct may be rescued using RSV subgroup B helper virus to give infectious RSV in accordance with Example 9.1. This basic rescue system for the complete native, i.e., 'wild-type' RSV A2 strain genomic RNA can be employed to introduce a variety of modifications into the cDNA copy of the genome resulting in the introduction of heterologous sequences into the genome. Such changes can be designed to reduce viral pathogenicity without restricting virus replication to a point where rescue becomes impossible or where virus gene expression is insufficient to stimulate adequate immunity.

These modifications can comprise gross alterations of the genetic structure of RSV, such as gene shuffling. For example, the RSV '$M_1$' gene can be translocated to a position closer to the 5' end of the genome, in order to take advantage of the known 3' to 5' gradient in virus gene expression, resulting in reduced levels of '$M_1$' protein expression in infected cells and thereby reducing the rate of virus assembly and maturation. Other genes and/or regulatory regions may also be translocated appropriately, in some cases from other strains of RSV of human or animal origin. For example, the 'F' gene (and possibly the 'G' gene) of a human subgroup B RSV could be inserted into an otherwise RSV strain A genome (in place of, or in addition to the RSV strain A 'F' and 'G' genes).

In another approach, the RNA sequence of the RSV viruses 'N' protein is translocated from its 3' proximal site to a position closer to the 5' end of the genome, again taking advantage of the 3' to 5' gradient in gene transcription to reduce the level of N protein produced. By reducing the level of N protein produced, there would result a concomitant increase in the relative rates of transcription of genes involved in stimulating host immunity to RSV and a concomitant reduction in the relative rate of genome replication. Thus, by translocating the RSV RNA sequence coding for RSV N protein, a chimeric RSV virus having attenuated pathogenicity relative to native RSV will be produced.

Another exemplary translocation modification resulting in, in effect, the introduction of heterologous sequence as is discussed herein may result in the production of attenuated chimeric RSV comprises the translocation of RSV RNA sequence coding for the 'L' protein of RSV. This sequence of the RSV virus is believed responsible for viral polymerase protein production. By translocating the RSV sequence coding for L protein from its native 5' terminal location in the native RSV genome to a location at or near the 3' terminus of the genome, a chimeric RSV virus exhibiting attenuated pathogenicity will be produced. Yet another exemplary translocation comprises the switching the locations of the RSV RNA sequences coding for the RSV G and F proteins (ie, relative to each other in the genome) to achieve a chimeric RSV having attenuated pathogenicity resulting from the slight modification in the amount of the G and F proteins produced. Such gene shuffling modifications as are exemplified and discussed above are believed to result in a chimeric, modified RSV having attenuated pathogenicity in comparison to the native RSV starting material. The nucleotide sequences for the foregoing encoded proteins are known, as is the nucleotide sequence for the entire RSV genome. See McIntosh, Respiratory Syncytial Virus in Virology, 2d Ed. edited by B. N. Fields, D. M. Knipe et al., Raven Press, Ltd. New York, 1990 Chapter 38, pp1045–1073, and references cited therein.

These modifications can additionally or alternatively comprise localized, site specific, single or multiple, nucleotide substitutions, deletions or additions within genes and/ or regulatory domains of the RSV genome. Such site specific, single or multiple, substitutions, deletions or additions can reduce virus pathogenicity without overly attenuating it, for example, by reducing the number of lysine or arginine residues at the cleavage site in the F protein to reduce efficiency of its cleavage by host cell proteases (where cleavage is believed to be an essential step in functional activation of the 'F' protein), and thereby possibly reduce virulence. Site specific modifications in the 3' or 5' regulatory regions of the RSV genome may also be used to increase transcription at the expense of genome replication. In addition, localized manipulation of domains within the N protein, which is believed to control the switch between transcription and replication can be made to reduce genome replication but still allow high levels of transcription. Further, the cytoplasmic domain(s) of the G and F glycoproteins can be altered in order to reduce their rate of migration through the endoplasmic reticulum and golgi of infected cells, thereby slowing virus maturation. In such cases, it may be sufficient to modify the migration of G protein only, which would then allow additional up-regulation of 'F' production, the main antigen involved in stimulating neutralizing antibody production during RSV infections. Such localized substitutions, deletions or additions within genes and /or regulatory domains of the RSV genome are believed to result in chimeric, modified RSV also having reduced pathogenicity relative to the native RSV genome starting material.

9.3 Use of Monoclonal Antibodies to Differentiate Rescued Virus from Helper Virus In order to neutralize the RSV strain B9320 helper virus and facilitate identification of rescued A2 strain RSV, monoclonal antibodies against RSV strain B9320 were made as follows.

Six BALB/c female mice were infected intranasally (i.n.) with ~$10^5$ plaque forming units (p.f.u.) of RSV B9320, followed 5 weeks later by intraperitoneal (i.p.) inoculation with $10^6$ –$10^7$ pfu of RSV B9320 in a mixture containing 50% complete Freund's adjuvant. Two weeks after i.p. inoculation, a blood sample from each mouse was tested for the presence of RSV specific antibody using a standard neutralization assay (Beeler and Coelingh, *J. Virol.* 63:2941–2950 (1988)). Mice producing the highest level of neutralizing antibody were then further boosted with ~$10^6$ p.f.u. of RSV strain B9320 in phosphate buffered saline (PBS), injected intravenously at the base of the tail. Three days later, the mice were sacrificed and their spleens collected as a source of monoclonal antibody producing B-cells. Spleenocytes (including B-cells) were teased from the mouse spleen through incisions made in the spleen capsule into 5 ml of Dulbecco's Modified Eagle's Medium (DME). Clumps of cells were allowed to settle out, and the remaining suspended cells were separately collected by centrifugation at ~2000×g for 5 minutes at room temperature. These cell pellets were resuspended in 15 ml 0.83% (w/v) $NH_4Cl$, and allowed to stand for 5 minutes to lyse red blood cells. Spleenocytes were then collected by centrifugation as before through a 10 ml cushion of fetal calf serum. The spleenocytes were then rinsed in DME, repelleted and finally resuspended in 20 ml of fresh DME. These spleenocytes were then mixed with Sp2/0 cells (a mouse myeloma cell line used as fusion partners for the immortalization of spleenocytes) in a ratio of ~10:1, spleen cells: Sp2/0 cells. Sp2/0 cells were obtained from the ATCC and maintained in DME supplemented with 10% fetal bovine serum. The cell mixture was then centrifuged for 8 minutes at 2000×g at room temperature. The cell pellet was resuspended in 1 ml of 50% polyethylene glycol 1000 mol. wt. (PEG 1000), followed by addition of equal volumes of DME at 1 minute intervals until a final volume of 25 ml was attained. The fused cells were then pelleted as before and resuspended at 3.5 ×10$^6$ spleen cells ml$^{-1}$ in growth medium (50% conditioned medium from Sp2/0 cells, 50% HAT medium containing 100 ml RPMI 25 ml F.C.S., 100 μgml$^{-1}$ gentamicin, 4 ml 50× Hypoxanthine, Thymidine, Aminopterin (HAT) medium supplied as a prepared mixture by Sigma Chem. Co., St. Louis, Mo.). The cell suspension was distributed over 96 well plates (200 μl well$^{-1}$) and incubated at 37° C., 95% humidity and 5% $CO_2$. Colonies of hybridoma cells (fused spleenocytes and Sp2/0 cells) were then subcultured into 24 well plates and grown until nearly confluent; the supernatant growth medium was then sampled for the presence of RSV strain B9320 neutralizing monoclonal antibody, using a standard neutralization assay (Beeler and Coelingh, J. Virol. 63:2941–50 (1988)). Hybridoma cells from wells with neutralizing activity were resuspended in growth medium and diluted to give a cell density of ~0.5 cells per 100 μl and plated out in 96 well plates, 200 μl per well. This procedure ensured the production of monoclones (i.e. hybridoma cell lines derived from a single cell) which were then reassayed for the production of neutralizing monoclonal antibody. Those hybridoma cell lines which produced monoclonal antibody capable of neutralizing RSV strain B9320 but not RSV strain A2 were subsequently injected into mice, i.p. (10$^6$ cells per mouse). Two weeks after the i.p. injection mouse ascites fluid containing neutralizing monoclonal antibody for RSV strain B9320 was tapped with a 19 gauge needle, and stored at −20° C.

This monoclonal antibody was used to neutralize the RSV strain B9320 helper virus following rescue of RSV strain A2 as described in Section 9.1. This was carried out by diluting neutralizing monoclonal antibody 1 in 50 with molten 0.4% (w/v) agar in Eagle's Minimal Essential Medium (EMEM) containing 1% F.C.S. This mixture was then added to Hep-2 cell monolayers, which had been infected with the progeny of rescue experiments at an m.o.i. of ~0.1–0.01 pfu cell$^{-1}$. The monoclonal antibody in the agar overlay inhibited the growth of RSV strain B9320, but allowed the growth of RSV strain A2, resulting in plaque formation by the A2 strain. These plaques were picked using a pasteur pipette to remove a plug of agar above the plaque and the infected cells within the plaque; the cells and agar plug were resuspended in 2 ml of EMEM, 1 % FCS, and released virus was plaqued again in the presence of monoclonal antibody on a fresh Hep-2 cell monolayer to further purify from helper virus. The twice plaqued virus was then used to infect Hep-2 cells in 24 well plates, and the progeny from that were used to infect 6 well plates at an m.o.i. of ~0.1 pfu cell$^{-1}$. Finally, total infected cell RNA from one well of a 6 well plate was used in an RT/PCR reaction using first and second strand primers on either side of the 'marker sequences' (introduced into the RSV strain A2 genome to act as a means of recognizing rescue events) as described in Section 9.2 above. The DNA produced from the RT/PCR reaction was subsequently digested with StuI and PmeI to positively identify the 'marker sequences' introduced into RSV strain A2 cDNA, and hence to establish the validity of the rescue process.

10. DEPOSIT OF MICROORGANISMS

An *E. coli* cell line containing the plasmid pIVACAT is being deposited with the Agricultural Research Culture Collection (NRRL), Peoria, IL; and has the following accession number

| Strain | Plasmid | Ascension Number |
|---|---|---|
| *E. coli* (DH5a) | pIVACAT | NRRL |

The present investigation is not to be limited in scope by the specific embodiments described which are intended as single illustrations of individual aspects of the invention, and any constructs, viruses or enzymes which are functionally equivalent are within the scope of this invention. Indeed, various modifications of the invention in addition to those shown and described herein will become apparent to those skilled in the art from the foregoing description and accompanying drawings. Such modifications are intended to fall within the scope of the appended claims. 78.

---

What is claimed is:

1. A recombinant RNA molecule comprising a binding site specific for an RNA-directed RNA polymerase derived from a respiratory syncytial virus, operatively linked to a heterologous RNA sequence comprising the reverse complement of an mRNA coding sequence.

2. A recombinant RNA molecule comprising a heterologous RNA sequence comprising the reverse complement of an mRNA coding sequence, operatively linked to a 3'-noncoding viral sense flanking sequence of a respiratory syncytial virus containing the viral polymerase binding site, and to a 540 -noncoding viral sense flanking sequence of respiratory syncytial virus.

3. A recombinant RNP comprising the recombinant RNA molecule of claim 1 mixed with the purified RNA-directed RNA polymerase.

4. A recombinant RNP comprising the recombinant RNA molecule of claim 3 mixed with purified respiratory syncytial viral polymerase.

5. A recombinant RNP comprising the recombinant RNA molecule of claim 2 mixed with purified respiratory syncytial viral polymerase.

6. A chimeric virus comprising a respiratory syncytial virus containing a heterologous RNA sequence comprising the reverse complement of an mRNA coding sequence, operatively linked to a respiratory syncytial viral polymerase binding site.

7. A chimeric virus comprising a respiratory syncytial virus containing a heterologous RNA sequence comprising the reverse complement of an mRNA coding sequence, operatively linked to a polymerase binding site of the respiratory syncytial virus.

8. A method for producing a chimeric respiratory syncytial virus (RSV) comprising:

(a) culturing a host cell transfected with a heterologous RNA sequence comprising the reverse complement of an mRNA coding sequence operatively linked to a RSV polymerase binding site and infected with a parental strain of RSV and, (b) recovering said chimeric virus from the culture.

9. A chimeric RSV produced by the method of claim 8.

* * * * *

SEQUENCE LISTING ( 1 ) GENERAL INFORMATION:

( i i i ) NUMBER OF SEQUENCES: 43

( 2 ) INFORMATION FOR SEQ ID NO:1:

( i ) SEQUENCE CHARACTERISTICS:
        ( A ) LENGTH: 95 bases
        ( B ) TYPE: nucleic acid
        ( C ) STRANDEDNESS: single
        ( D ) TOPOLOGY: linear ( i i ) MOLECULE TYPE: SYNTHETIC DNA ( i x ) SEQUENCE DESCRIPTION: SEQ ID NO:1:

GAAGCTTAAT ACGACTCACT ATAAGTAGAA ACAAGGGTGT TTTTTCATAT CATTTAAACT    60

TCACCCTGCT TTTGCTGAAT TCATTCTTCT GCAGG    95

( 2 ) INFORMATION FOR SEQ ID NO:2:

( i ) SEQUENCE CHARACTERISTICS:
        ( A ) LENGTH: 15 bases
        ( B ) TYPE: nucleic acid
        ( C ) STRANDEDNESS: single
        ( D ) TOPOLOGY: linear ( i i ) MOLECULE TYPE: SYNTHETIC DNA ( x i ) SEQUENCE DESCRIPTION: SEQ ID NO:2:

CCTGCAGAAG AATGA    15

( 2 ) INFORMATION FOR SEQ ID NO:3:

( i ) SEQUENCE CHARACTERISTICS:
        ( A ) LENGTH: 95 bases
        ( B ) TYPE: nucleic acid
        ( C ) STRANDEDNESS: single
        ( D ) TOPOLOGY: linear ( i i ) MOLECULE TYPE: SYNTHETIC DNA ( x i ) SEQUENCE DESCRIPTION: SEQ ID NO:3:

GAAGCTTAAT ACGACTCACT ATAAGCAAAA GCAGGGTGAA GTTTAAATGA TATGAAAAAA    60

CACCCTTGTT TCTACTGAAT TCATTCTTCT GCAGG    95

( 2 ) INFORMATION FOR SEQ ID NO:4:

( i ) SEQUENCE CHARACTERISTICS:
        ( A ) LENGTH: 68 bases
        ( B ) TYPE: nucleic acid
        ( C ) STRANDEDNESS: single
        ( D ) TOPOLOGY: linear ( i i ) MOLECULE TYPE: SYNTHETIC DNA ( x i ) SEQUENCE DESCRIPTION: SEQ ID NO:4:

AGCTTAATAC GACTCACTAT AAGATCTATT AAACTTCACC CTGCTTTTGC TGAATTCATT    60

CTTCTGCA    68

( 2 ) INFORMATION FOR SEQ ID NO:5:

( i ) SEQUENCE CHARACTERISTICS:
        ( A ) LENGTH: 60 bases
        ( B ) TYPE: nucleic acid
        ( C ) STRANDEDNESS: single
        ( D ) TOPOLOGY: linear ( i i ) MOLECULE TYPE: SYNTHETIC DNA ( x i ) SEQUENCE DESCRIPTION: SEQ ID NO:5:

GAAGAATGAA TTCAGCAAAA GCAGGGTGAA GTTTAATAGA TCTTATAGTG AGTCGTATTA    60

( 2 ) INFORMATION FOR SEQ ID NO:6:

( i ) SEQUENCE CHARACTERISTICS:
        ( A ) LENGTH: 42 bases
        ( B ) TYPE: nucleic acid
        ( C ) STRANDEDNESS: single
        ( D ) TOPOLOGY: linear ( i i ) MOLECULE TYPE: SYNTHETIC DNA ( x i ) SEQUENCE DESCRIPTION: SEQ ID NO:6:

CCGAATTCTT AATACGACTC ACTATAAGTA GAAACAAGGG TG 42

(2) INFORMATION FOR SEQ ID NO:7:

(i) SEQUENCE CHARACTERISTICS:
        (A) LENGTH: 30 bases
        (B) TYPE: nucleic acid
        (C) STRANDEDNESS: single
        (D) TOPOLOGY: linear (ii) MOLECULE TYPE: SYNTHETIC DNA (xi) SEQUENCE DESCRIPTION: SEQ ID NO:7:

CCTCTAGACG CTCGAGAGCA AAAGCAGGTG 30

(2) INFORMATION FOR SEQ ID NO:8:

(i) SEQUENCE CHARACTERISTICS:
        (A) LENGTH: 15 bases
        (B) TYPE: nucleic acid
        (C) STRANDEDNESS: single
        (D) TOPOLOGY: linear (ii) MOLECULE TYPE: SYNTHETIC DNA (xi) SEQUENCE DESCRIPTION: SEQ ID NO:8:

CACCCUGCUU UUGCU 15

(2) INFORMATION FOR SEQ ID NO:9:

(i) SEQUENCE CHARACTERISTICS:
        (A) LENGTH: 15 bases
        (B) TYPE: nucleic acid
        (C) STRANDEDNESS: single
        (D) TOPOLOGY: linear (ii) MOLECULE TYPE: SYNTHETIC RNA (xi) SEQUENCE DESCRIPTION: SEQ ID NO:9:

CACCCUGCUU UUACU 15

(2) INFORMATION FOR SEQ ID NO:10:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: SYNTHETIC RNA (xi) SEQUENCE DESCRIPTION: SEQ ID NO:10:

CACCCUGCUU CUGCU 15

(2) INFORMATION FOR SEQ ID NO:11:

(i) SEQUENCE CHARACTERISTICS:
        (A) LENGTH: 15 bases
        (B) TYPE: nucleic acid
        (C) STRANDEDNESS: single
        (D) TOPOLOGY: linear (ii) MOLECULE TYPE: SYNTHETIC RNA (xi) SEQUENCE DESCRIPTION: SEQ ID NO:11:

CACCCUGUUU UUGCU 15

(2) INFORMATION FOR SEQ ID NO:12:

( i ) SEQUENCE CHARACTERISTICS:
( A ) LENGTH: 15 bases
( B ) TYPE: nucleic acid
( C ) STRANDEDNESS: single
( D ) TOPOLOGY: linear ( i i ) MOLECULE TYPE: SYNTHETIC RNA ( x i ) SEQUENCE DESCRIPTION: SEQ ID NO:12:

CACCCUGUUU UUACU 15

( 2 ) INFORMATION FOR SEQ ID NO:13:

( i ) SEQUENCE CHARACTERISTICS:
( A ) LENGTH: 15 bases
( B ) TYPE: nucleic acid
( C ) STRANDEDNESS: single
( D ) TOPOLOGY: linear ( i i ) MOLECULE TYPE: SYNTHETIC RNA ( x i ) SEQUENCE DESCRIPTION: SEQ ID NO:13:

CACCCUGUUU CUGCU 15

( 2 ) INFORMATION FOR SEQ ID NO:14:

( i ) SEQUENCE CHARACTERISTICS:
( A ) LENGTH: 16 bases
( B ) TYPE: nucleic acid
( C ) STRANDEDNESS: single
( D ) TOPOLOGY: linear ( i i ) MOLECULE TYPE: SYNTHETIC RNA ( x i ) SEQUENCE DESCRIPTION: SEQ ID NO:14:

CACCCUUGCU UUUGCU 16

( 2 ) INFORMATION FOR SEQ ID NO:15:

( i ) SEQUENCE CHARACTERISTICS:
( A ) LENGTH: 16 bases
( B ) TYPE: nucleic acid
( C ) STRANDEDNESS: single
( D ) TOPOLOGY: linear ( i i ) MOLECULE TYPE: SYNTHETIC RNA ( x i ) SEQUENCE DESCRIPTION: SEQ ID NO:15:

CACCCUUGCU UUUACU 16

( 2 ) INFORMATION FOR SEQ ID NO:16:

( i ) SEQUENCE CHARACTERISTICS:
( A ) LENGTH: 16 bases
( B ) TYPE: nucleic acid
( C ) STRANDEDNESS: single
( D ) TOPOLOGY: linear ( i i ) MOLECULE TYPE: SYNTHETIC RNA ( x i ) SEQUENCE DESCRIPTION: SEQ ID NO:16:

CACCCUUGUU UUUACU 16

( 2 ) INFORMATION FOR SEQ ID NO:17:

( i ) SEQUENCE CHARACTERISTICS:
( A ) LENGTH: 16 bases
( B ) TYPE: nucleic acid
( C ) STRANDEDNESS: single ( D ) TOPOLOGY: linear ( i i ) MOLECULE TYPE: SYNTHETIC RNA ( x i ) SEQUENCE DESCRIPTION: SEQ ID NO:17:

CACCCUUGUU UCUACU        16

( 2 ) INFORMATION FOR SEQ ID NO:18:

( i ) SEQUENCE CHARACTERISTICS:
            ( A ) LENGTH: 96 base pairs
            ( B ) TYPE: nucleic acid
            ( C ) STRANDEDNESS: double
            ( D ) TOPOLOGY: linear ( i i ) MOLECULE TYPE: SYNTHETIC DNA ( x i ) SEQUENCE DESCRIPTION: SEQ ID NO:18:

CTAGACGCCC TGCAGCAAAA GCAGGGTGAC AAAGACATAA TGGAGAAAAA AATCACTGGG        60

TATACCACCG TTGATATATC CCAATCGCAT CGTAAA        96

( 2 ) INFORMATION FOR SEQ ID NO:19:

( i ) SEQUENCE CHARACTERISTICS:
            ( A ) LENGTH: 96 base pairs
            ( B ) TYPE: nucleic acid
            ( C ) STRANDEDNESS: double
            ( D ) TOPOLOGY: linear ( i i ) MOLECULE TYPE: SYNTHETIC DNA ( x i ) SEQUENCE DESCRIPTION: SEQ ID NO:19:

TGCGGGACGT CGTTTTCGTC CCACTGTTTC TGTATTACCT CTTTTTTTAG TGACCCATAT        60

GGTGGCAACT ATATAGGGTT AGCGTAGCAT TTCTTG        96

( 2 ) INFORMATION FOR SEQ ID NO:20:

( i ) SEQUENCE CHARACTERISTICS:
            ( A ) LENGTH: 34 bases
            ( B ) TYPE: nucleic acid
            ( C ) STRANDEDNESS: single
            ( D ) TOPOLOGY: linear ( i i ) MOLECULE TYPE: SYNTHETIC DNA ( x i ) SEQUENCE DESCRIPTION: SEQ ID NO:20:

actgcgatga gtggcagggc ggggcgtaat agat        34

( 2 ) INFORMATION FOR SEQ ID NO:21:

( i ) SEQUENCE CHARACTERISTICS:
            ( A ) LENGTH: 38 bases
            ( B ) TYPE: nucleic acid
            ( C ) STRANDEDNESS: single
            ( D ) TOPOLOGY: linear ( i i ) MOLECULE TYPE: SYNTHETIC DNA ( x i ) SEQUENCE DESCRIPTION: SEQ ID NO:21:

tgacgctact caccgtcccg ccccgcatta tctagatc        38

( 2 ) INFORMATION FOR SEQ ID NO:22:

( i ) SEQUENCE CHARACTERISTICS:
            ( A ) LENGTH: 34 bases
            ( B ) TYPE: nucleic acid
            ( C ) STRANDEDNESS: single
            ( D ) TOPOLOGY: linear (i i) MOLECULE TYPE: SYNTHETIC DNA (x i) SEQUENCE DESCRIPTION: SEQ ID NO:22:

ACTGCGATGA GTGGCAGGGC GGGGCGTAAT AGAT    34

(2) INFORMATION FOR SEQ ID NO:23:

(i) SEQUENCE CHARACTERISTICS:
        (A) LENGTH: 38 bases
        (B) TYPE: nucleic acid
        (C) STRANDEDNESS: single
        (D) TOPOLOGY: linear (i i) MOLECULE TYPE: SYNTHETIC DNA (x i) SEQUENCE DESCRIPTION: SEQ ID NO:23:

CTAGATCTAT TACGCCCCGC CCTGCCACTC ATCGCAGT    38

(2) INFORMATION FOR SEQ ID NO:24:

(i) SEQUENCE CHARACTERISTICS:
        (A) LENGTH: 97 bases
        (B) TYPE: nucleic acid
        (C) STRANDEDNESS: single
        (D) TOPOLOGY: linear (i i) MOLECULE TYPE: SYNTHETIC DNA (x i) SEQUENCE DESCRIPTION: SEQ ID NO:24:

CTAGACGCCC TGCAGCAAAA GCAGGGTGAC AAAGACATAA TGGAGAAAAA AAATCACTGG    60

GTATACCACC GTTGATATAT CCCAATCGCA TCGTAAA    97

(2) INFORMATION FOR SEQ ID NO:25:

(i) SEQUENCE CHARACTERISTICS:
        (A) LENGTH: 38 bases
        (B) TYPE: nucleic acid
        (C) STRANDEDNESS: single
        (D) TOPOLOGY: linear (i i) MOLECULE TYPE: SYNTHETIC DNA (x i) SEQUENCE DESCRIPTION: SEQ ID NO:25:

GTTCTTTACG ATGCGATTGG GATTTGCTG CAGGGCGT    38

(2) INFORMATION FOR SEQ ID NO:26:

(i) SEQUENCE CHARACTERISTICS:
        (A) LENGTH: 30 bases
        (B) TYPE: nucleic acid
        (C) STRANDEDNESS: single
        (D) TOPOLOGY: linear (i i) MOLECULE TYPE: SYNTHETIC DNA (x i) SEQUENCE DESCRIPTION: SEQ ID NO:26:

CGGAATTCTC TTCGAGCGAA AGCAGGAGTT    30

(2) INFORMATION FOR SEQ ID NO:27:

(i) SEQUENCE CHARACTERISTICS:
        (A) LENGTH: 42 bases
        (B) TYPE: nucleic acid
        (C) STRANDEDNESS: single
        (D) TOPOLOGY: linear (i i) MOLECULE TYPE: SYNTHETIC DNA ( x i ) SEQUENCE DESCRIPTION: SEQ ID NO:27:

CCAAGCTTAT TAACCCTCAC TAAAAGTAGA AACAAGGAGT TT                      42

( 2 ) INFORMATION FOR SEQ ID NO:28:

( i ) SEQUENCE CHARACTERISTICS:
        ( A ) LENGTH: 51 bases
        ( B ) TYPE: nucleic acid
        ( C ) STRANDEDNESS: single
        ( D ) TOPOLOGY: linear ( i i ) MOLECULE TYPE: SYNTHETIC DNA ( x i ) SEQUENCE DESCRIPTION: SEQ ID NO:28:

CATGGGTGAG TTTCGACCAA AATCTAGATT ATAAATAGG ATACATATGC A            51

( 2 ) INFORMATION FOR SEQ ID NO:29:

( i ) SEQUENCE CHARACTERISTICS:
        ( A ) LENGTH: 43 bases
        ( B ) TYPE: nucleic acid
        ( C ) STRANDEDNESS: single
        ( D ) TOPOLOGY: linear ( i i ) MOLECULE TYPE: SYNTHETIC DNA ( x i ) SEQUENCE DESCRIPTION: SEQ ID NO:29:

AATGTATCCT ATTTATAAT CTAGATTTTG GTCGAAACTC ACC                      43

( 2 ) INFORMATION FOR SEQ ID NO:30:

( i ) SEQUENCE CHARACTERISTICS:
        ( A ) LENGTH: 46 bases
        ( B ) TYPE: nucleic acid
        ( C ) STRANDEDNESS: single
        ( D ) TOPOLOGY: linear ( i i ) MOLECULE TYPE: SYNTHETIC DNA ( x i ) SEQUENCE DESCRIPTION: SEQ ID NO:30:

CGACGCATAT TACGCGAAAA AATGCGTACA ACAAACTTGC ATAAAC                  46

( 2 ) INFORMATION FOR SEQ ID NO:31:

( i ) SEQUENCE CHARACTERISTICS:
        ( A ) LENGTH: 50 bases
        ( B ) TYPE: nucleic acid
        ( C ) STRANDEDNESS: single
        ( D ) TOPOLOGY: linear ( i i ) MOLECULE TYPE: SYNTHETIC DNA ( x i ) SEQUENCE DESCRIPTION: SEQ ID NO:31:

CAAAAAATG GGGCAAATAA GAATTTGATA AGTACCACTT AAATTTAACT              50

( 2 ) INFORMATION FOR SEQ ID NO:32:

( i ) SEQUENCE CHARACTERISTICS:
        ( A ) LENGTH: 24 bases
        ( B ) TYPE: nucleic acid
        ( C ) STRANDEDNESS: single
        ( D ) TOPOLOGY: linear ( i i ) MOLECULE TYPE: SYNTHETIC DNA ( x i ) SEQUENCE DESCRIPTION: SEQ ID NO:32:

CTAGAGTTAA ATTTAAGTGG TACT                                          24

( 2 ) INFORMATION FOR SEQ ID NO:33:

( i ) SEQUENCE CHARACTERISTICS:
        ( A ) LENGTH: 50 bases
        ( B ) TYPE: nucleic acid
        ( C ) STRANDEDNESS: single
        ( D ) TOPOLOGY: linear ( i i ) MOLECULE TYPE: SYNTHETIC DNA ( x i ) SEQUENCE DESCRIPTION: SEQ ID NO:33:

TATCAAATTC TTATTTGCCC CATTTTTTG GTTTATGCAA GTTTGTTGTA 50

( 2 ) INFORMATION FOR SEQ ID NO:34:

( i ) SEQUENCE CHARACTERISTICS:
        ( A ) LENGTH: 30 bases
        ( B ) TYPE: nucleic acid
        ( C ) STRANDEDNESS: single
        ( D ) TOPOLOGY: linear ( i i ) MOLECULE TYPE: SYNTHETIC DNA ( x i ) SEQUENCE DESCRIPTION: SEQ ID NO:34:

CGCATTTTTT CGCGTAATAT GCGTCGGTAC 30

( 2 ) INFORMATION FOR SEQ ID NO:35:

( i ) SEQUENCE CHARACTERISTICS:
        ( A ) LENGTH: 50 bases
        ( B ) TYPE: nucleic acid
        ( C ) STRANDEDNESS: single
        ( D ) TOPOLOGY: linear ( i i ) MOLECULE TYPE: SYNTHETIC DNA ( x i ) SEQUENCE DESCRIPTION: SEQ ID NO:35:

GTATTCAATT ATAGTTATTA AAAATTAAAA ATCATATAAT TTTTTAAATA 50

( 2 ) INFORMATION FOR SEQ ID NO:36:

( i ) SEQUENCE CHARACTERISTICS:
        ( A ) LENGTH: 50 bases
        ( B ) TYPE: nucleic acid
        ( C ) STRANDEDNESS: single
        ( D ) TOPOLOGY: linear ( i i ) MOLECULE TYPE: SYNTHETIC DNA ( x i ) SEQUENCE DESCRIPTION: SEQ ID NO:36:

ACTTTTAGTG AACTAATCCT AAAGTTATCA TTTTAATCTT GGAGGAATAA 50

( 2 ) INFORMATION FOR SEQ ID NO:37:

( i ) SEQUENCE CHARACTERISTICS:
        ( A ) LENGTH: 50 bases
        ( B ) TYPE: nucleic acid
        ( C ) STRANDEDNESS: single
        ( D ) TOPOLOGY: linear ( i i ) MOLECULE TYPE: SYNTHETIC DNA ( x i ) SEQUENCE DESCRIPTION: SEQ ID NO:37:

ATTTAAACCC TAATCTAATT GGTTTATATG TGTATTAACT AAATTACGAG 50

( 2 ) INFORMATION FOR SEQ ID NO:38:

( i ) SEQUENCE CHARACTERISTICS:
        ( A ) LENGTH: 46 bases
        ( B ) TYPE: nucleic acid ( C ) STRANDEDNESS: single
( D ) TOPOLOGY: linear ( i i ) MOLECULE TYPE: SYNTHETIC DNA ( x i ) SEQUENCE DESCRIPTION: SEQ ID NO:38:

ATATTAGTTT TTGACACTTT TTTTCTCGTT ATAGTGAGTC GTATTA 46

( 2 ) INFORMATION FOR SEQ ID NO:39:

( i ) SEQUENCE CHARACTERISTICS:
( A ) LENGTH: 25 bases
( B ) TYPE: nucleic acid
( C ) STRANDEDNESS: single
( D ) TOPOLOGY: linear ( i i ) MOLECULE TYPE: SYNTHETIC DNA ( x i ) SEQUENCE DESCRIPTION: SEQ ID NO:39:

AGCTTAATAC GACTCACTAT AACGA 25

( 2 ) INFORMATION FOR SEQ ID NO:40:

( i ) SEQUENCE CHARACTERISTICS:
( A ) LENGTH: 50 bases
( B ) TYPE: nucleic acid
( C ) STRANDEDNESS: single
( D ) TOPOLOGY: linear ( i i ) MOLECULE TYPE: SYNTHETIC DNA ( x i ) SEQUENCE DESCRIPTION: SEQ ID NO:40:

GAAAAAAGT GTCAAAAACT AATATCTCGT AATTTAGTTA ATACACATAT 50

( 2 ) INFORMATION FOR SEQ ID NO:41:

( i ) SEQUENCE CHARACTERISTICS:
( A ) LENGTH: 50 bases
( B ) TYPE: nucleic acid
( C ) STRANDEDNESS: single
( D ) TOPOLOGY: linear ( i i ) MOLECULE TYPE: SYNTHETIC DNA ( x i ) SEQUENCE DESCRIPTION: SEQ ID NO:41:

AAACCAATTA GATTAGGGTT TAAATTTATT CCTCCAAGAT TAAAATGATA 50

( 2 ) INFORMATION FOR SEQ ID NO:42:

( i ) SEQUENCE CHARACTERISTICS:
( A ) LENGTH: 50 bases
( B ) TYPE: nucleic acid
( C ) STRANDEDNESS: single
( D ) TOPOLOGY: linear ( i i ) MOLECULE TYPE: SYNTHETIC DNA ( x i ) SEQUENCE DESCRIPTION: SEQ ID NO:42:

ACTTTAGGAT TAGTTCACTA AAAGTTATTT AAAAAATTAT ATGATTTTA 50

( 2 ) INFORMATION FOR SEQ ID NO:43:

( i ) SEQUENCE CHARACTERISTICS:
( A ) LENGTH: 29 bases
( B ) TYPE: nucleic acid
( C ) STRANDEDNESS: single
( D ) TOPOLOGY: linear ( i i ) MOLECULE TYPE: SYNTHETIC DNA ( x i ) SEQUENCE DESCRIPTION: SEQ ID NO:43:

ATTTTTAATA ACTATAATTG AATACTGCA 29